(12) United States Patent
Gore et al.

(10) Patent No.: US 7,884,114 B2
(45) Date of Patent: Feb. 8, 2011

(54) COMPOUNDS

(75) Inventors: Paul Martin Gore, Stevenage (GB);
Ashley Paul Hancock, Stevenage (GB);
Simon Teanby Hodgson, Stevenage
(GB); **Panayiotis Alexandrou
Procopiou, Stevenage (GB); Sadie Vile**,
Stevenage (GB)

(73) Assignee: Glaxo Group Limited, Greenford,
Middlesex (GB)

( * ) Notice: Subject to any disclaimer, the term of this
patent is extended or adjusted under 35
U.S.C. 154(b) by 255 days.

(21) Appl. No.: 12/190,868

(22) Filed: Aug. 13, 2008

(65) Prior Publication Data

US 2009/0270355 A1 Oct. 29, 2009

Related U.S. Application Data

(60) Provisional application No. 60/955,941, filed on Aug. 15, 2007, provisional application No. 61/082,585, filed on Jul. 22, 2008.

(51) Int. Cl.
*C07D 215/38* (2006.01)
*A61K 31/04* (2006.01)
(52) U.S. Cl. ...................... 514/314; 546/167
(58) Field of Classification Search ............ 514/314; 546/167
See application file for complete search history.

(56) References Cited

U.S. PATENT DOCUMENTS

| 5,093,340 A * | 3/1992 | Mohrs et al. ............. 514/311 |
| 2006/0094767 A1 | 5/2006 | Tsubouchi et al. |
| 2006/0205719 A1 | 9/2006 | Hubschwerlen et al. |
| 2007/0021424 A1 | 1/2007 | Abouabdellah et al. |

FOREIGN PATENT DOCUMENTS

| EP | 0261539 A2 | 3/1986 |
| WO | 01/57021 A2 | 8/2001 |
| WO | 03/008409 A1 | 1/2003 |
| WO | 03/047582 A1 | 6/2003 |
| WO | 03/047583 A1 | 6/2003 |
| WO | 03/047584 A1 | 6/2003 |
| WO | 03/047585 A1 | 6/2003 |
| WO | 03/048159 A1 | 6/2003 |
| WO | 03/105850 A1 | 12/2003 |
| WO | 2004/005284 A1 | 1/2004 |
| WO | 2004/009121 A1 | 1/2004 |
| WO | 2004/078748 A2 | 9/2004 |
| WO | 2005/030140 A2 | 4/2005 |
| WO | 2005/051302 A1 | 6/2005 |
| WO | 2005/095346 A1 | 10/2005 |
| WO | 2006/046552 A1 | 5/2006 |
| WO | 2006/108059 A1 | 10/2006 |
| WO | 2006/110516 A1 | 10/2006 |

OTHER PUBLICATIONS

Battaglia et al.; "Indole Amide Derivatives: Synthesis, Structure-Activity Relationships and Molecular Modeling Studies of a New Series of Histamine H1-Receptor Antagonists"; European Journal of Medicinal Chemistry: 1999; vol. 34; pp. 93-105.
Simons et al.; "Clinical Pharmacology of New Histamine H1 Receptor Antagonists"; Clinical Pharmokinetics; 1999; vol. 36, No. 5; pp. 329-352.
Souers et al.; "Synthesis and Evaluation of 2-Amino-8-Alkoxy Quinolines as MCHr1 Antagonists, Part 3"; Bioorganic and Medicinal Chemistry Letters; 2004; vol. 14, No. 19, pp. 4883-4886.
Colin A Leach, Thomas H Brown, Robert J Ife, David J Keeling, Michael E Parsons, Colin J Theobald, Kenneth J Wiggall; Reversible Inhibitors of the Gastric (H+/K+)-ATPase 4. Indentification of an Inhibitor with an Intermediate Duration of Action; Journal of Medicinal Chemistry; 1995; 38; 2748-2762; ACS.

* cited by examiner

*Primary Examiner*—D. Margaret Seaman
(74) *Attorney, Agent, or Firm*—James P. Riek

(57) ABSTRACT

The present invention relates to a compound which is N-(4-{4-[(6-butyl-8-quinolinyl)oxy]-1-piperidinyl}butyl)ethanesulfonamide

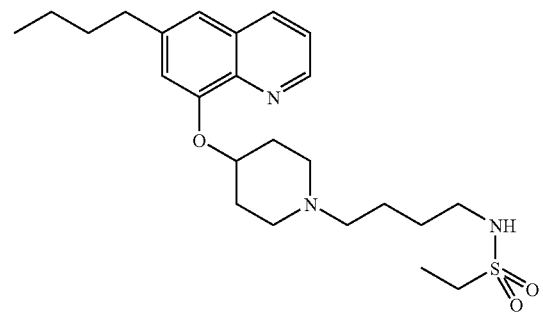

and salts thereof, processes for its preparation, to compositions containing it and to its use in the treatment of various diseases, such as allergic rhinitis.

18 Claims, 3 Drawing Sheets

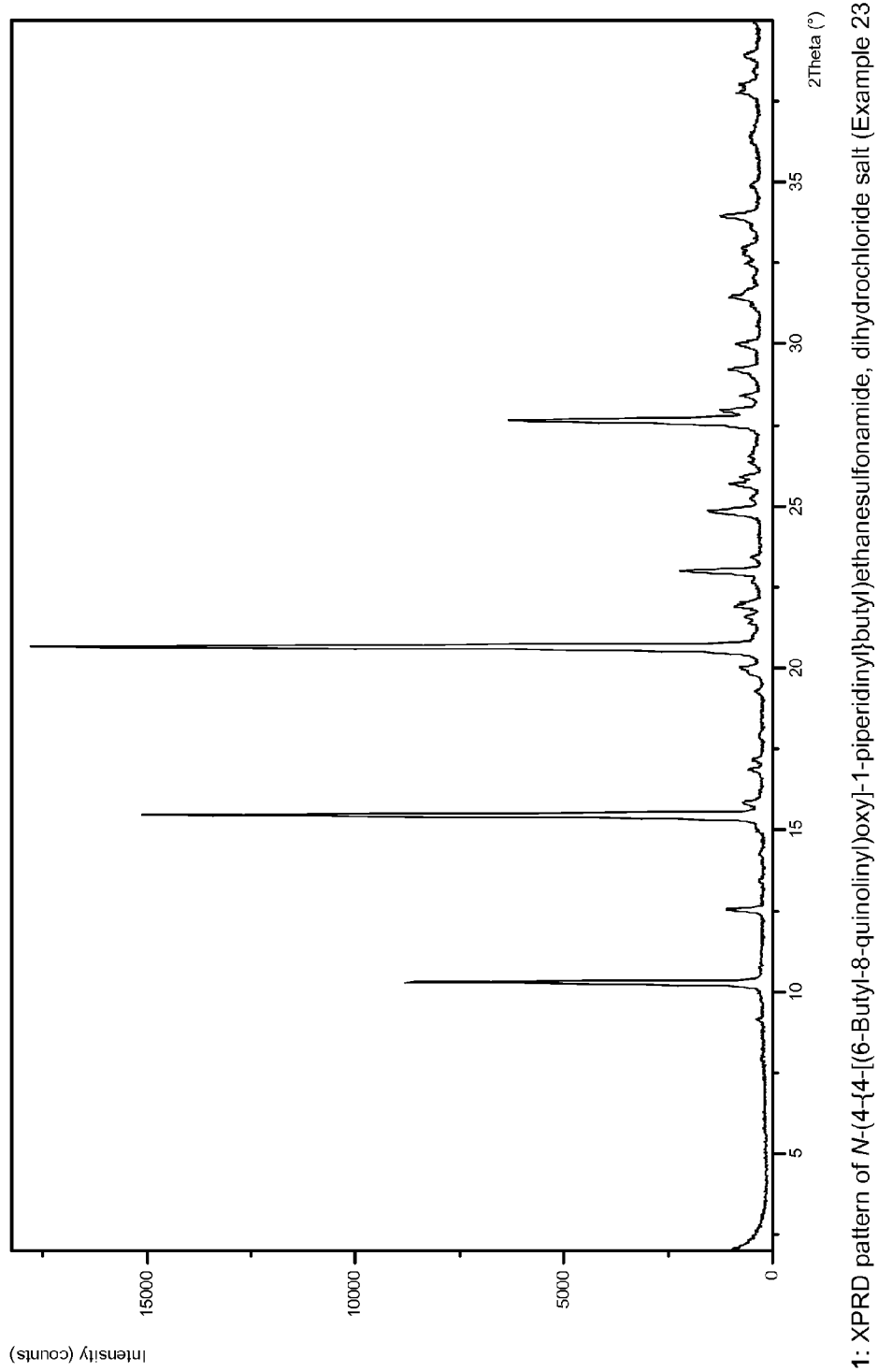
Figure 1: XPRD pattern of N-(4-{4-[(6-Butyl-8-quinolinyl)oxy]-1-piperidinyl}butyl)ethanesulfonamide, dihydrochloride salt (Example 23B) with linear scale on intensity axis (y-axis)

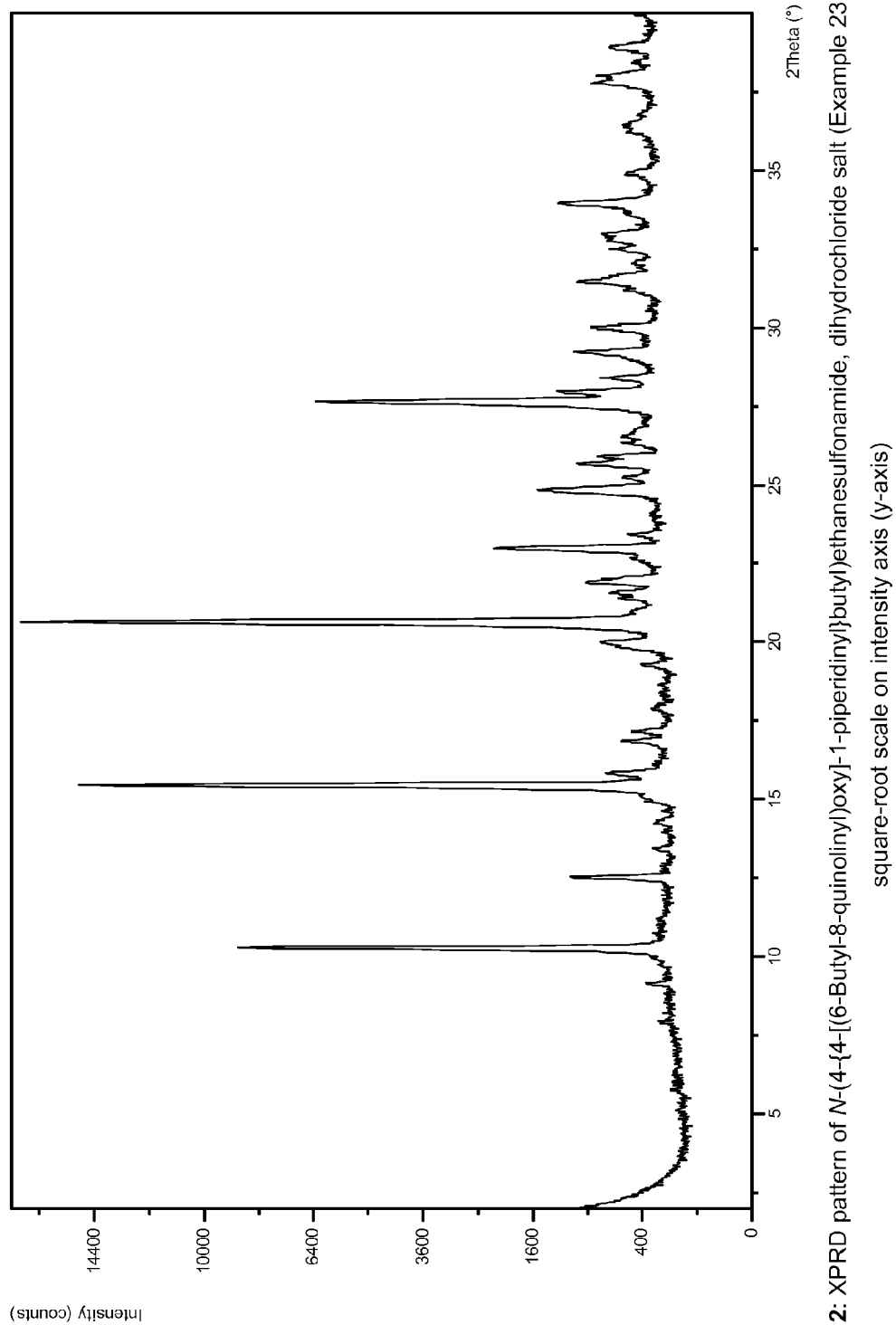
Figure 2: XPRD pattern of N-(4-{4-[(6-Butyl-8-quinolinyl)oxy]-1-piperidinyl}butyl)ethanesulfonamide, dihydrochloride salt (Example 23B) with square-root scale on intensity axis (y-axis)

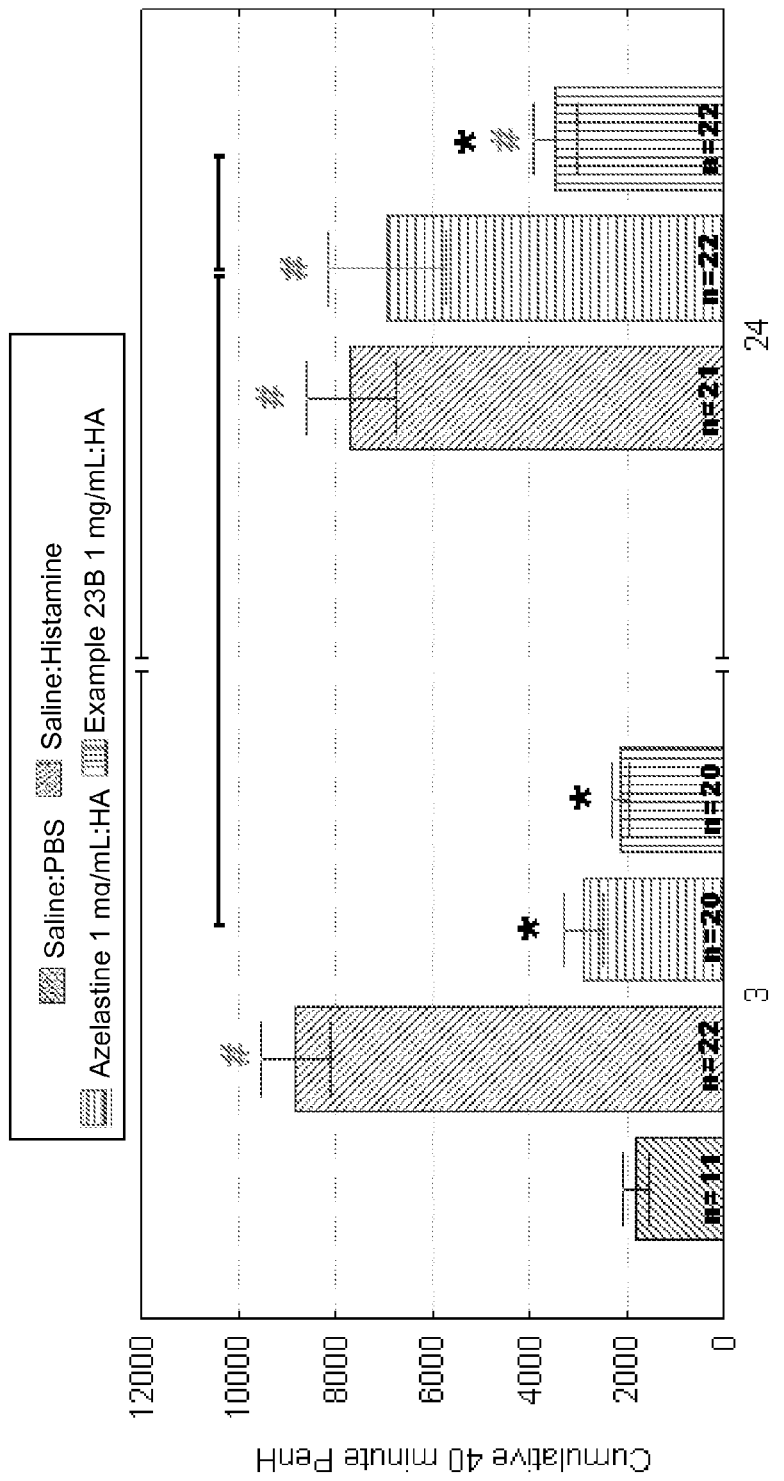

Figure 3: Duration of action of N-(4-{4-[((6-butyl-8-quinolinyl)oxy]-1-piperidinyl}butyl)ethanesulfonamide, dihydrochloride salt (Example 23B) and azelastine in a conscious guinea-pig model of histamine-induced nasal congestion. Animals were exposed to histamine at the time indicated after an intranasal dose of 1mg/ml Example 23B or azelastine. Mean ± s.e.mean (n = 11-22 per group as indicated).

(*$p<0.05$ compared to time-matched histamine control group; # $p<0.05$ compared to vehicle/PBS control group. Bar indicates $p<0.05$ individual comparison as indicated. ANOVA with post-Hochberg analysis)

COMPOUNDS

CROSS REFERENCES TO RELATED APPLICATIONS

This application claims priority, pursuant to 35 USC 120, to U.S. Provisional Application No. 60/955,941 filed 15 Aug. 2007, and U.S. Provisional Application No. 61/082,585 filed 22 Jul. 2008.

The present invention relates to a class of compounds which are quinolinyloxypiperidine and pyrrolidine derivatives, processes for their preparation, pharmaceutical compositions containing them and to their use in the treatment of various diseases, in particular inflammatory and/or allergic diseases of the respiratory tract.

Allergic rhinitis (seasonal and perennial), pulmonary inflammation and congestion are medical conditions that are often associated with other conditions such as asthma and chronic obstructive pulmonary disease (COPD). In general, these conditions are mediated, at least in part, by inflammation associated with the release of histamine from various cells, in particular mast cells.

Allergic rhinitis, also known as 'hay fever' affects a large proportion of the population worldwide. There are two types of allergic rhinitis, seasonal and perennial. The clinical symptoms of seasonal allergic rhinitis typically include nasal itching and irritation, sneezing and watery rhinorrhea, which is often accompanied by nasal congestion. The clinical symptoms of perennial allergic rhinitis are similar, except that nasal blockage may be more pronounced. Either type of allergic rhinitis may also cause other symptoms, such as itching of the throat and/or eyes, epiphora and oedema around the eyes. The symptoms of allergic rhinitis may vary in intensity from the nuisance level to debilitating.

Allergic rhinitis and other allergic conditions are associated with the release of histamine from various cell types, but particularly mast cells. The physiological effects of histamine are classically mediated by three receptor subtypes, termed H1, H2 and H3. H1 receptors are widely distributed throughout the CNS and periphery, and are involved in wakefulness and acute inflammation. H2 receptors mediate gastric acid secretion in response to histamine. H3 receptors are present on the nerve endings in both the CNS and periphery and mediate inhibition of neurotransmitter release [Hill et al., *Pharmacol. Rev.*, 49:253-278, (1997)]. A fourth member of the histamine receptor family has been identified, termed the H4 receptor [Hough, *Mol. Pharmacol.*, 59:415-419, (2001)]. Whilst the distribution of the H4 receptor appears to be restricted to cells of the immune and inflammatory systems, a physiological role for this receptor remains to be identified.

The activation of H1 receptors in blood vessels and nerve endings are responsible for many of the symptoms of allergic rhinitis, which include itching, sneezing, and the production of watery rhinorrhea. Oral antihistamine compounds which are selective H1 receptor antagonists, such as chlorphenyramine, cetirizine, desloratidine and fexofenadine are effective in treating the itching, sneezing and rhinorrhea associated with allergic rhinitis. Intranasal antihistamines which are selective H1 receptor antagonists, such as azelastine and levocabastine, are thought to have similar therapeutic effects to their oral counterparts. However, such compounds generally require twice daily administration and may still cause sedatation despite their local application.

A class of compounds have been identified as H1 receptor antagonists.

Thus the present invention provides a compound of formula (I)

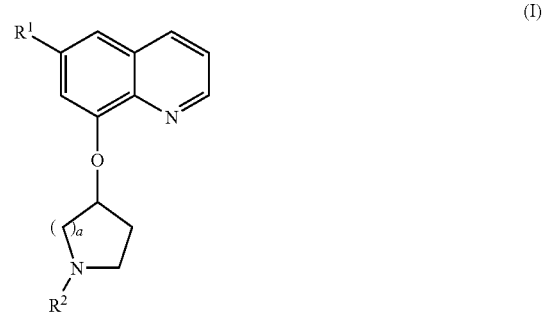

wherein $R^1$ represents straight chain $C_{1-6}$alkyl;

a represents 1 or 2;

$R^2$ represents —$C_{1-6}$alkylene-$R^3$-$R^4$, in which the alkylene is straight chain and is optionally substituted by one $C_{1-3}$alkyl group, or $R^2$ represents a saturated 5 to 7 membered ring containing one $SO_2$ group;

$R^3$ represents —$SO_2$—, —$N(R^5)SO_2$—, —$SO_2N(R^6)$— or —$N(R^7)C(O)N(R^8)$—;

$R^4$ represents —$C_{1-6}$alkyl, —$C_{5-7}$cycloalkyl optionally substituted by one or two $C_{1-3}$alkyl groups, —$C_{1-3}$alkylene$C_{5-7}$cycloalkyl in which the $C_{5-7}$cycloalkyl is optionally substituted by one or two $C_{1-3}$alkyl groups, -aryl optionally substituted by one or two substituents independently selected from halogen, $C_{1-3}$alkyl, trifluoromethyl, or cyano groups, or —$C_{1-3}$alkylene-aryl optionally substituted by one or two substituents independently selected from halogen, $C_{1-3}$alkyl, trifluoromethyl, or cyano groups;

$R^5$, $R^6$, $R^7$ and $R^8$ each independently represent hydrogen or $C_{1-6}$alkyl;

or together $R^6$ and $R^4$ represent a saturated 5 to 7 membered ring, optionally containing one —O—, —S—, —NH—, or —$N(CH_3)$— group;

or together $R^3$ and $R^4$ represent a saturated 5 to 7 membered ring, optionally containing one —O—, —S—, —NH—, or —$N(CH_3)$— group;

or a salt thereof.

The compounds of the invention may be expected to be useful in the treatment of various diseases in particular inflammatory and/or allergic diseases, such as inflammatory and/or allergic diseases of the respiratory tract (for example allergic rhinitis) that are associated with the release of histamine from cells such as mast cells. Further, preferred compounds show an improved profile, in that they possess one or more of the following properties:

(i) greater selectivity over the H3 receptor;

(ii) lower CNS penetration;

(iii) prolonged duration of action;

(iv) lower bioavailability/oral absorption.

Compounds having such a profile may be particularly suitable for intranasal delivery, and/or capable of once daily administration and/or further may have an improved side effect profile compared with other existing therapies.

By 'selectivity' it is meant that the compounds may be more potent at the H1 receptor than at other receptors, particularly the H3 receptor and/or the hERG receptor. The activity at the H1 receptor may be at least about 10 fold greater (e.g. about 100 fold greater) than activity at the H3 receptor.

In one embodiment, $R^4$ represents —$C_{1-6}$alkyl, —$C_{5-7}$cycloalkyl optionally substituted by one or two $C_{1-3}$alkyl groups, —$C_{1-3}$alkylene$C_{5-7}$cycloalkyl in which the $C_{5-7}$cycloalkyl is optionally substituted by one or two $C_{1-3}$alkyl groups, -aryl optionally substituted by one or two substituents independently selected from halogen, $C_{1-3}$alkyl, trifluoromethyl, or cyano groups, or —$C_{1-3}$alkylene-aryl optionally substituted on aryl by one or two substituents independently selected from halogen, $C_{1-3}$alkyl, trifluoromethyl, or cyano groups.

In one embodiment, $R^1$ represents straight chain $C_{1-6}$alkyl;

a represents 1 or 2;

$R^2$ represents —$C_{1-6}$alkylene-$R^3$-$R^4$, in which the alkylene is straight chain and is optionally substituted by one $C_{1-3}$alkyl group, or $R^2$ represents a saturated 5 to 7 membered ring containing one $SO_2$ group;

$R^3$ represents —$SO_2$—, —$N(R^5)SO_2$—, —$SO_2N(R^6)$— or —$N(R^7)C(O)N(R^8)$—;

$R^4$ represents —$C_{1-6}$alkyl, —$C_{5-7}$cycloalkyl optionally substituted by one or two $C_{1-3}$alkyl groups, —$C_{1-3}$alkylene$C_{5-7}$cycloalkyl in which the $C_{5-7}$cycloalkyl is optionally substituted by one or two $C_{1-3}$alkyl groups, -aryl optionally substituted by one or two substituents independently selected from halogen, $C_{1-3}$alkyl, trifluoromethyl, or cyano groups, or —$C_{1-3}$alkylene-aryl optionally substituted by one or two substituents independently selected from halogen, $C_{1-3}$alkyl, trifluoromethyl, or cyano groups;

$R^5$, $R^6$, $R^7$ and $R^8$ each independently represent hydrogen or $C_{1-6}$alkyl; or a salt thereof.

In another embodiment, $R^1$ represents $C_{2-5}$alkyl;

a represents 1 or 2;

$R^2$ represents —$C_{2-5}$alkylene-$R^3$-$R^4$, in which the alkylene is straight chain and is optionally substituted by one $C_{1-3}$alkyl (e.g. methyl) group, or $R^2$ represents a saturated 5 membered ring containing one $SO_2$ group;

$R^3$ represents —$SO_2$—, —$N(R^5)SO_2$—, —$SO_2N(R^6)$— or —$N(R^7)C(O)N(R^8)$—;

$R^4$ represents —$C_{1-4}$alkyl, —$C_{5-6}$cycloalkyl, —$C_1$alkylene$C_{5-6}$cycloalkyl, -aryl (e.g. phenyl) optionally substituted by one or two (e.g. one) substituent(s) independently selected from halogen, $C_{1-3}$alkyl (e.g. methyl), trifluoromethyl, or cyano groups, or —$C_1$alkylene-aryl (e.g. methylphenyl) optionally substituted by one or two (e.g. one) substituent(s) independently selected from halogen, $C_{1-3}$alkyl (e.g. methyl), trifluoromethyl, or cyano groups;

$R^5$, $R^6$, $R^7$ and $R^8$ each independently represent hydrogen or $C_{1-3}$alkyl; or a salt thereof.

In another embodiment $R^1$ represents $C_{2-5}$alkyl (e.g. n-butyl or n-pentyl).

In another embodiment, a represents 2.

In another embodiment, $R^2$ represents —$C_{2-5}$alkylene-$R^3$-$R^4$, in which the alkylene is straight chain and is optionally substituted by one $C_{1-3}$alkyl (e.g. methyl) group, or $R^2$ represents a saturated five membered ring containing one $SO_2$ group.

In another embodiment, $R^2$ represents —$C_{2-5}$alkylene-$R^3$-$R^4$ (e.g. —$C_{2-4}$alkylene-$R^3$-$R^4$), in which the alkylene is straight chain and is optionally substituted by one $C_{1-3}$alkyl (e.g. methyl) group.

In another embodiment, $R^3$ represents —$SO_2$—, —$N(R^5)SO_2$— or —$SO_2N(R^6)$—.

In another embodiment, $R^3$ represents —$N(R^5)SO_2$— or —$SO_2N(R^6)$—.

In another embodiment, $R^3$ represents —$SO_2$—.

In another embodiment, $R^3$ represents —$N(R^5)SO_2$—.

In another embodiment, $R^3$ represents —$SO_2N(R^6)$—.

In another embodiment, $R^4$ represents —$C_{1-6}$alkyl, —$C_{5-7}$cycloalkyl, —$C_{1-3}$alkylene$C_{5-7}$cycloalkyl, -aryl (e.g. phenyl) optionally substituted by one or two (e.g. one) substituent(s) independently selected from halogen, $C_{1-3}$alkyl (e.g. methyl), trifluoromethyl, or cyano groups, or —$C_{1-3}$alkylene-aryl (e.g. $C_{1-3}$alkylene-phenyl) optionally substituted by one or two (e.g. one) substituent(s) independently selected from halogen, $C_{1-3}$alkyl (e.g. methyl), trifluoromethyl, or cyano groups.

In another embodiment, $R^4$ represents —$C_{1-4}$alkyl, —$C_{5-6}$cycloalkyl, —$C_1$alkylene$C_{5-6}$cycloalkyl, -aryl (e.g. phenyl) optionally substituted by one or two (e.g. one) substituent(s) independently selected from halogen, $C_{1-3}$alkyl (e.g. methyl), trifluoromethyl, or cyano groups, or —$C_1$alkylene-aryl (e.g. methylphenyl) optionally substituted by one or two (e.g. one) substituent(s) independently selected from halogen, $C_{1-3}$alkyl (e.g. methyl), trifluoromethyl, or cyano groups.

In another embodiment, $R^4$ represents —$C_{1-4}$alkyl, —$C_{5-6}$cycloalkyl, —$C_1$alkylene$C_{5-6}$cycloalkyl or -aryl (e.g. phenyl) optionally substituted by one or two (e.g. one) substituent(s) independently selected from halogen, $C_{1-3}$alkyl (e.g. methyl), trifluoromethyl, or cyano groups.

In another embodiment, $R^4$ represents —$C_{1-4}$alkyl, —$C_{5-6}$cycloalkyl, —$C_1$alkylene$C_{5-6}$cycloalkyl or unsubstituted aryl (e.g. phenyl).

In another embodiment, $R^5$, $R^6$, $R^7$ and $R^8$ each independently represent hydrogen or $C_{1-3}$alkyl (e.g. methyl).

In another embodiment, when $R^3$ represents —$SO_2$—, $R^4$ represents —$C_{1-6}$alkyl (e.g. methyl, ethyl, propyl, iso-propyl, butyl, or tert-butyl) or $C_{5-7}$cycloalkyl (e.g. cyclopentyl).

In another embodiment, when $R^3$ represents —$N(R^5)SO_2$—, $R^4$ represents —$C_{1-6}$alkyl (e.g. methyl, ethyl, propyl, iso-propyl or iso-butyl), —$C_{5-7}$cycloalkyl (e.g. cyclohexyl), —$C_{1-3}$alkylene$C_{5-7}$cycloalkyl (e.g. methylcyclohexyl) or unsubstituted aryl (e.g. phenyl) and $R^5$ represents hydrogen or $C_{1-3}$alkyl (e.g. methyl).

In another embodiment, when $R^3$ represents —$SO_2N(R^6)$—, $R^4$ represents —$C_{1-6}$alkyl (e.g. propyl or tert-butyl) and $R^6$ represents hydrogen.

In another embodiment, when $R^3$ represents —$N(R^7)C(O)N(R^8)$—, $R^4$ represents —$C_{1-6}$alkyl (e.g. propyl) and $R^7$ and $R^8$ both represent hydrogen.

In another embodiment, there is provided a compound which is 6-butyl-8-({1-[3-(ethylsulfonyl)propyl]-4-piperidinyl}oxy)quinoline, or a salt thereof, such as a pharmaceutically acceptable salt thereof.

In another embodiment, there is provided a compound which is N-(4-{4-[(6-butyl-8-quinolinyl)oxy]-1-piperidinyl}butyl)ethanesulfonamide, or a salt thereof, such as a pharmaceutically acceptable salt thereof.

In another embodiment, there is provided a compound which is N-(4-{4-[(6-butyl-8-quinolinyl)oxy]-1-piperidinyl}butyl)ethanesulfonamide, in the form of the free base.

In another embodiment, there is provided a compound which is N-(4-{4-[(6-butyl-8-quinolinyl)oxy]-1-piperidinyl}butyl)ethanesulfonamide, in the form of a dihydrochloride salt.

In another embodiment, there is provided a compound which is N-(4-{4-[(6-butyl-8-quinolinyl)oxy]-1-piperidinyl}butyl)ethanesulfonamide, dihydrochloride salt, polymorphic form 1.

In another embodiment, there is provided a compound of formula (I) as defined above with the proviso that the compound is not 6-butyl-8-({1-[3-(ethylsulfonyl)propyl]-4-piperidinyl}oxy)quinoline, or a salt thereof, such as a pharmaceutically acceptable salt thereof.

In another embodiment, there is provided a compound of formula (I) as defined above with the proviso that the compound is not N-(4-{4-[(6-butyl-8-quinolinyl)oxy]-1-piperidinyl}butyl)ethanesulfonamide, or a salt thereof, such as a pharmaceutically acceptable salt thereof.

In another embodiment, there is provided a compound of formula (I) as defined above with the proviso that the compound is not 6-butyl-8-({1-[3-(ethylsulfonyl)propyl]-4-piperidinyl}oxy)quinoline or N-(4-{4-[(6-butyl-8-quinolinyl)oxy]-1-piperidinyl}butyl)ethane sulfonamide, or salts thereof, such as pharmaceutically acceptable salts thereof.

Representative compounds of formula (I) include the compounds of Examples 1 to 36 and individual isomers thereof, in the form of a free base, or as salts thereof, such as pharmaceutically acceptable salts thereof.

It is to be understood that the invention includes all possible combinations of groups and substituents described herein.

$C_{1-6}$alkyl, whether alone or as part of another group, and unless otherwise stated, may be straight chain or branched. $C_{1-3}$alkyl shall be interpreted similarly. Representative examples include, but are not limited to methyl, ethyl, n-propyl, iso-propyl, n-butyl, sec-butyl, iso-butyl, t-butyl, n-pentyl, neo-pentyl and n-hexyl.

$C_{1-6}$alkylene, unless otherwise stated, may be straight chain or branched. $C_{1-3}$alkylene shall be interpreted similarly. Representative examples of straight chain $C_{1-6}$alkylene include methlyene[—$(CH_2)$—], ethylene[—$(CH_2)_2$—], propylene, [—$(CH_2)_3$—], butylene[—$(CH_2)_4$—], pentylene[—$(CH_2)_5$—] and hexylene[—$(CH_2)_6$—].

As defined herein, the term "aryl" includes single and fused aromatic rings. Representative examples of aryl groups include, but are not limited to phenyl, indenyl, anthrancenyl and naphthyl. Aryl is intended to denote all isomers thereof (i.e. all possible points of attachment to the aryl ring). A representative aryl group is phenyl.

As defined herein, the term "$C_{5-7}$cycloalkyl" refers to a non-aromatic cyclic hydrocarbon ring having from five to seven carbon atoms. Examples of such ring systems include cyclopentyl, cyclohexyl and cycloheptyl.

The term "halogen" is used herein to describe, unless otherwise stated, a group selected from fluorine, chlorine, bromine or iodine, particularly fluorine and chlorine.

It is to be understood that the present invention covers compounds of formula (I) as the free base and as salts thereof, for example as a pharmaceutically acceptable salt.

It is to be further understood that references hereinafter to compounds of the invention or to compounds of formula (I) mean a compound of formula (I) as the free base, or as a salt.

The compounds of formula (I) may be in the form of and/or may be administered as a pharmaceutically acceptable salt. For a review on suitable salts see Berge et al., J. Pharm. Sci., 1977, 66, 1-19. Suitable pharmaceutically acceptable salts include acid addition salts. As used herein, the term "pharmaceutically acceptable salt", means any pharmaceutically acceptable salt of a compound of formula (I), which upon administration to the recipient is capable of providing (directly or indirectly) a compound of formula (I), or an active metabolite or residue thereof.

Typically, a pharmaceutically acceptable salt may be readily prepared by using a desired acid as appropriate. The salt may precipitate from solution and be collected by filtration or may be recovered by evaporation of the solvent.

A pharmaceutically acceptable acid addition salt can be formed by reaction of a compound of formula (I) with a suitable inorganic or organic acid (such as hydrobromic, hydrochloric, sulphuric, nitric, phosphoric, succinic, maleic, formic, acetic, propionic, fumaric, citric, tartaric, lactic, benzoic, salicylic, glutamic, aspartic, p-toluenesulfonic, benzenesulfonic, methanesulfonic, ethanesulfonic, naphthalenesulfonic (e.g. 2-naphthalenesulfonic), naphthalene disulfonic (e.g. 1,5-naphthalene disulfonic), naphthoic, 1-hydroxy-2-naphthoic, biphenylsulfonic, xinfanoic or hexanoic acid), optionally in a suitable solvent such as an organic solvent, to give the salt which is usually isolated for example by crystallisation and filtration. A pharmaceutically acceptable acid addition salt of a compound of formula (I) can comprise or be for example a hydrobromide, hydrochloride, sulfate, nitrate, phosphate, succinate, maleate, formate, acetate, propionate, fumarate, citrate, tartrate, lactate, benzoate, salicylate, glutamate, aspartate, p-toluenesulfonate, benzenesulfonate, methanesulfonate, ethanesulfonate, naphthalenesulfonate (e.g. 2-naphthalenesulfonate), naphthalene disulfonate (e.g. 1,5-naphthalene disulfonate), naphthoate, 1-hydroxy-2-naphthoate, biphenylsulfonate, xinfanoate or hexanoate salt. Particular salts are the hydrochloride salt or dihydrochloride salt of compounds of formula (I).

Compounds of formula (I) in which $R^3$ represents —$NR^5SO_2$— or —$SO_2NR^6$— may form base addition salts. Suitable pharmaceutically acceptable base salts include ammonium salts, alkali metal salts such as those of sodium and potassium, alkaline earth metal salts such as those of calcium and magnesium, and salts with organic bases whose $pK_a$ is >13.

Other non-pharmaceutically acceptable salts, e.g. oxalates or trifluoroacetates, may be used, for example in the isolation of the compounds of formula (I), and are included within the scope of this invention.

Particular salts of N-(4-{4-[(6-butyl-8-quinolinyl)oxy]-1-piperidinyl}butyl)ethanesulfonamide include naphthalene disulfonate salts, such as a 2,6- or a 1,5-naphthalene disulfonate salt, e.g. a 1,5-naphthalene disulfonate salt. Another particular salt is the dihydrochloride salt.

The invention includes within its scope all possible stoichiometric and non-stoichiometric forms of the salts of the compounds of formula (I).

It will be appreciated that many organic compounds can form complexes with solvents in which they are reacted or from which they are precipitated or crystallized. These complexes are known as "solvates". For example, a complex with water is known as a "hydrate". Solvents with high boiling points and/or solvents which are capable of forming hydrogen bonds such as water, xylene, N-methylpyrrolidinone, methanol and ethanol may be used to form solvates. Methods for identification of solvates include, but are not limited to, NMR and microanalysis. Solvates of the compounds of formula (I) are within the scope of the invention.

The compounds of formula (I) may be in a crystalline or amorphous state, which are included in the scope of the present invention. Furthermore, if crystalline, the compounds of formula (I) may exist in one or more polymorphic forms, which are included in the scope of the present invention. The most thermodynamically stable polymorphic form, at room temperature, of compounds of formula (I) is of particular interest.

Polymorphic forms of compounds of formula (I) may be characterized and differentiated using a number of conventional analytical techniques, including, but not limited to, X-ray powder diffraction (XRPD), infrared spectroscopy (IR), Raman spectroscopy, differential scanning calorimetry (DSC), thermogravimetric analysis (TGA) and solid state nuclear magnetic resonance (ssNMR).

It will be appreciated that the compounds of formula (I) may possess one or more asymmetric carbon atoms so that optical isomers e.g. enantiomers or diastereoisomers may be formed. The present invention encompasses optical isomers of the compounds of formula (I) whether as individual isomers isolated such as to be substantially free of the other isomer (i.e. pure) or as mixtures thereof (e.g. racemates and racemic mixtures). An individual isomer isolated such as to be substantially free of the other isomer (i.e. pure) may be isolated such that less than about 10%, particularly less than about 1%, for example less than about 0.1% of the other isomer is present.

Further, it will be appreciated that the R and S enantiomers may be isolated from the racemate by conventional resolution methods such as preparative HPLC involving a chiral stationary phase, by resolution using fractional crystallisation of a salt of the free base with a chiral acid, by chemical conversion to a diastereoisomer using a chiral auxiliary followed by chromatographic separation of the isomers and then removal of the chiral auxiliary and regeneration of the pure enantiomer, or by asymmetric synthesis.

Certain compounds of formula (I) may exist in one of several tautomeric forms. It will be understood that the present invention encompasses tautomers of the compounds of formula (I) whether as individual tautomers or as mixtures thereof.

It will be appreciated from the foregoing that included within the scope of the invention are solvates, hydrates, optical isomers, tautomers and polymorphic forms of the compounds of formula (I) and salts thereof.

There is also provided processes for the preparation of compounds of formula (I) or salts thereof.

For the avoidance of doubt, throughout the process section, unless otherwise stated, $(CH_2)_n$ corresponds to the $C_{1-6}$alkylene defined in $R^2$ in the compounds of formula (I), and thus may be optionally substituted by one $C_{1-3}$alkyl group.

According to a first process, A, a compound of formula (I) in which $R^3$ represents —$SO_2$— may be prepared by reacting a compound of formula (II)

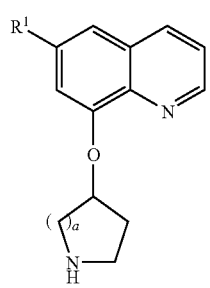

(II)

with a compound of formula (III)

(III)

wherein $R^1$, a and $R^4$ are as defined hereinabove, n represents 1 to 6, $(CH_2)_n$ may be optionally substituted by one $C_{1-3}$alkyl group, and X represents a suitable leaving group such as chlorine, bromine, tosylate or mesylate.

The reaction may typically be carried out in a suitable solvent, such as N,N'-dimethylformamide (DMF), optionally using an appropriate activating agent, e.g. sodium iodide, with a suitable base, such as sodium bicarbonate (sodium hydrogen carbonate) or potassium carbonate. The reaction is typically heated, for example using a microwave oven at a temperature of about 100 to 150° C. for an appropriate time, such as about 15 to 30 min. Alternatively, the reaction may be heated using conventional methods for longer periods of time, such as for several hours or overnight, as appropriate.

Compounds of formula (II) may be prepared according to Scheme 1 below.

Compounds of formula (III) in which X represents chlorine or bromine may be prepared according to Scheme 3 and/or are commercially available. Examples of such compounds which are commercially available, for example from Apollo and/or Aldrich and/or Chemical Blocks and/or TCI Europe, include 1-[(2-chloroethyl)sulfonyl]pentane, 2-chloroethyl phenyl sulfone, p-toluenesulfonyl methyl chloride, 1-[(2-chloroethyl)sulfonyl]-4-methylbenzene, 2-chloroethyl 3-[(trifluoromethyl)phenyl]sulfone, 2-chloroethyl 4-fluorophenyl sulfone, 2-chloroethyl 4-chlorophenyl sulfone and 1-{[(2-chloroethyl)sulfonyl]methyl}benzene, bromomethylphenyl sulfone and 3,5-bis(trifluoromethyl)phenyl chloromethyl sulfone.

Compounds of formula (III) in which X represents tosylate or mesylate may be prepared according to Scheme 4.

Scheme 1 - Synthesis of compounds of formula (II)

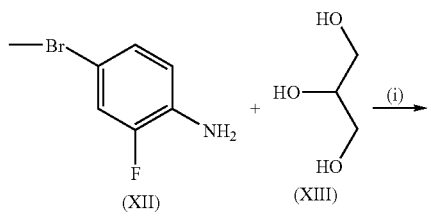

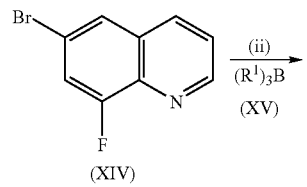

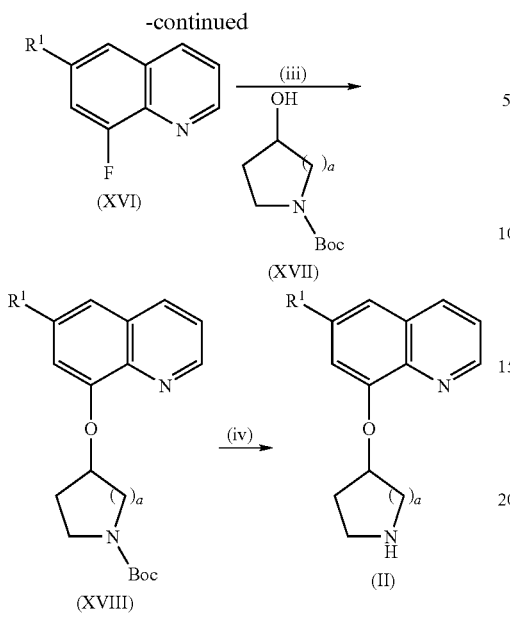

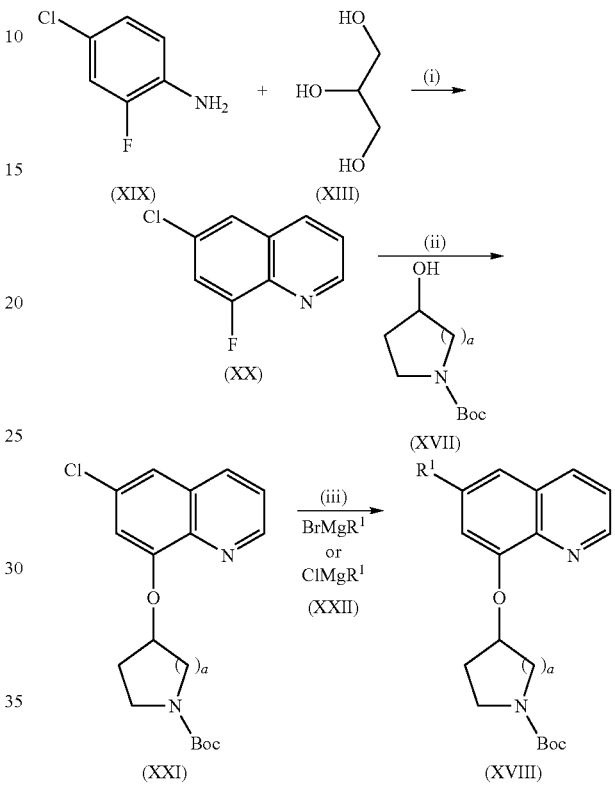

wherein R¹ and a are as defined hereinabove, and Boc represents tert-butoxycarbonyl.

Reagents and Conditions: i) suitable acid e.g. concentrated sulphuric acid, appropriate solvent such as water, sodium 3-nitrobenzenesulfonate (commercially available, for example, from Aldrich), appropriate elevated temperature such as from about 110 to 140° C.; ii) Suzuki reaction using a suitable solvent such as DMF and/or tetrahydrofuran (THF), suitable base e.g. potassium carbonate, appropriate catalyst for example [1,1'-bis(diphenylphosphino) ferrocene palladium (II)]chloride, at an elevated temperature such as from about 70 to 80° C. (for example using microwave radiation); iii) suitable solvent such as N-methylpyrrolidinone (NMP), appropriate base e.g. sodium tert-butoxide, at an elevated temperature for example from about 130 to 150° C.; iv) deprotection using a suitable acid e.g. trifluoroacetic acid (TFA) or hydrogen chloride in a suitable solvent such as dichloromethane (DCM), dioxane, iso-propylalcohol or toluene at room temperature.

Alternatively, step ii) in Scheme 1 may be carried out using 9-borabicyclo[3.3.1]nonane and an appropriate olefin to make a boron compound (equivalent to compound (XV)) in situ. The reaction is typically carried out in a suitable solvent such as THF with an appropriate catalyst e.g. 1,1'-bis(diphenylphosphino)ferrocene]dichloropalladium(II). The reaction is carried out in a manner similar to that described by S. Potuzak and D. S. Tan, *Tetrahedron Lett.*, 45:1797-1801, (2004). Olefins are commercially available, for example, from Aldrich and include ethene, 1-propene, 1-butene, 1-pentene and 1-hexene.

The compound of formula (XII), 4-bromo-2-fluoroaniline is commercially available, for example, from Aldrich.

The compound of formula (XIII), glycerol, is commercially available, for example, from Fluka and/or Aldrich.

The compounds of formula (XV) are commercially available, for example from Aldrich, and include trimethylboron, triethylborane and tributylborane.

Compounds of formula (XVII) are commercially available, for example from Aldrich and include N-tert-butoxycarbonyl-(R)-(−)-3-pyrrolidinol, N-tert-butoxycarbonyl-(S)-(+)-3-pyrrolidinol and tert-butyl 4-hydroxy-1-piperidinecarboxylate.

Compounds of formula (XVIII) may also be prepared according to Scheme 2 below.

wherein R¹ and a are as defined hereinabove and Boc represents tert-butoxycarbonyl.

Reagents and Conditions: i) suitable acid e.g. concentrated sulphuric acid, appropriate solvent such as water, sodium 3-nitrobenzenesulfonate (commercially available, for example, from Aldrich), appropriate elevated temperature such as from about 110 to 140° C.; ii) suitable solvent such as NMP, appropriate base e.g. sodium tert-butoxide, at an appropriate elevated temperature for example from about 130 to 150° C.; iii) suitable solvent such as THF:NMP (10:1) at an appropriate lowered temperature e.g. from about 0 to 5° C., using a suitable catalyst for example iron (III) acetylacetonate, preferably in an inert, water-free atmosphere.

Alternatively, step (iii) of Scheme 2 may be performed before step (ii) of Scheme 2, thereby first forming a compound of formula (XVI), and subsequently a compound of formula (XVIII).

The compound of formula (XIX), 4-chloro-2-fluoroaniline, is commercially available, for example, from Aldrich.

Compounds of formula (XVII) and (XIII) are commercially available, see above (after Scheme 1).

Compounds of formula (XXII) are commercially available, for example, from Aldrich and/or TCI-Europe and include methylmagnesium bromide, ethylmagnesium bromide, n-propylmagnesium bromide, n-butylmagnesium bromide, n-pentylmagnesium bromide and n-hexylmagnesium bromide.

Scheme 3: Synthesis of compounds of formula (III) in which X represents chlorine or bromine

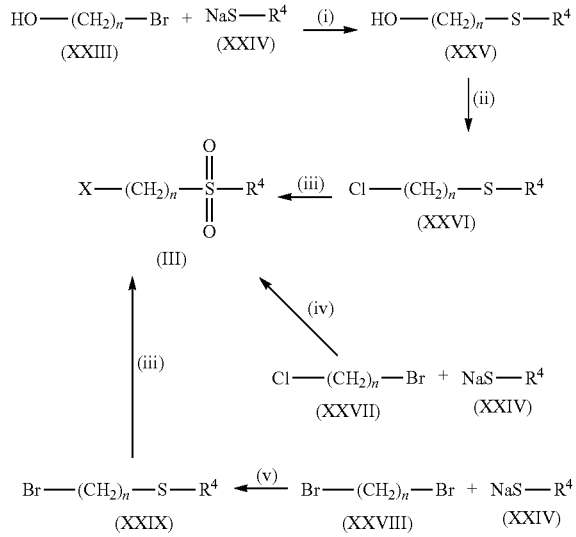

wherein $R^4$ is as defined hereinabove, n represents 1 to 6 and $(CH_2)_n$ may be optionally substituted by one $C_{1-3}$alkyl group.

Reagents and Conditions: i) suitable solvent such as DMF, at an elevated temperature such as from about 60 to 90° C.; ii) appropriate base e.g. triethylamine, in a suitable solvent for example DCM, methanesulfonylchloride (commercially available, for example, from Aldrich) and optionally in the presence of additional chloride ions e.g. lithium chloride or n-butylammonium chloride; iii) suitable solvent such as DCM, appropriate oxidising agent e.g. m-chloroperbenzoic acid (commercially available, for example, from Aldrich); iv) appropriate solvent such as ethanol or DMF, optionally at an appropriate elevated temperature e.g. from about 60 to 80° C., followed by treatment with an appropriate oxidising agent e.g. m-chloroperbenzoic acid in a suitable solvent e.g. DCM; v) suitable solvent such as DMF at an appropriate elevated temperature e.g. from about 60 to 80° C.

Compounds of formula (XXIII) are commercially available, for example, from Aldrich and/or Apollo and/or TCI-Europe, and include 2-bromoethanol, 3-bromopropanol, 4-bromobutanol, 5-bromopentanol, 6-bromohexanol, 1-bromo-2-propanol, (R)-(−)-3-bromo-2-methyl-1-propanol, (S)-(−)-3-bromo-2-methyl-1-propanol and 1-bromo-2-butanol.

Compounds of formula (XXIV) are commercially available, for example, from Aldrich, and include sodium ethanethiolate, sodium 1-propanethiolate, sodium 2-propanethiolate, sodium 1-butanethiolate, sodium 2-methyl-2-propanethiolate, sodium thiophenoxide and sodium 4-methylbenzenethiolate.

Compounds of formula (XXIV) may also be prepared in situ, by the addition of a suitable base, such as sodium hydride to a solution of the corresponding thiol in a suitable solvent, such as DMF. The suspension may be left for an appropriate amount of time, e.g. about 15 min, before continuing with the reactions described in Scheme 3.

Thiol compounds corresponding to compounds of formula (XXIV) are commercially available, for example, from Aldrich and/or TCI-Europe and/or Apollo, and include methanemercaptan, 2-methyl-2-butanethiol, 3-methyl-1-butanethiol, 1-pentanethiol, hexylmercaptan, cyclopentanethiol, cyclohexanethiol, 2-naphthalenethiol, thiophenol, 2-bromothiophenol, 4-fluorothiophenol, 2,5-dichlorothiophenol, 3-methylbenzenethiol, 2-ethylthiophenol, 2-iso-propylthiophenol, 2,4-dimethylthiophenol, benzyl mercaptan, phenylethylmercaptan, 2-chlorobenzyl mercaptan, 3-methylbenzyl mercaptan and 3,5-bis(trifluoromethyl)thiophenol.

Compounds of formula (XXV) may be prepared as described in Scheme 3, or may also be commercially available, for example, from TCI-Europe and/or Alfa Aesar and/or Aldrich, and include 2-(ethylthio)ethanol, 2-(iso-butylthio)ethanol, 4-(methylthio)-1-butanol, 3-(methylthio)-1-hexanol, 2-hydroxyethyl benzyl sulphide, 2-hydroxyethyl n-pentyl sulphide, 4-chlorobenzyl 2-hydroxyethyl sulphide and 3-(methylthio)-1-propanol.

Compounds of formula (XXVI) are also commercially available, for example, from Acros and/or Aldrich, and include 2-chloroethyl ethyl sulphide and 1-{[(2-chloroethyl)sulfonyl]methyl}benzene.

Compounds of formula (XXVII) are commercially available, for example, from TCI-Europe and/or Aldrich and/or Alfa Aesar, and include 1-bromo-2-chloroethane, 2-bromo-1-chloropropane, 1-bromo-3-chloropropane, 1-bromo-4-chlorobutane, 1-bromo-3-chloro-2-methylpropane, 1-bromo-5-chloropentane and 1-bromo-6-chlorohexane.

Compounds of formula (XXVIII) are commercially available, for example, from Aldrich, and/or Alfa Aesar and include dibromomethane, 1,2-dibromoethane, 1,2-dibromopropane, 1,2-dibromobutane, 1,3-dibromopropane, 1,3-dibromobutane, 1,4-dibromobutane, 1,4-dibromopentane, 1,5-dibromopentane, 1,5-dibromo-3-methylpentane and 1,6-dibromohexane.

Scheme 4: Synthesis of compounds of formula (III) in which X represents mesylate or tosylate

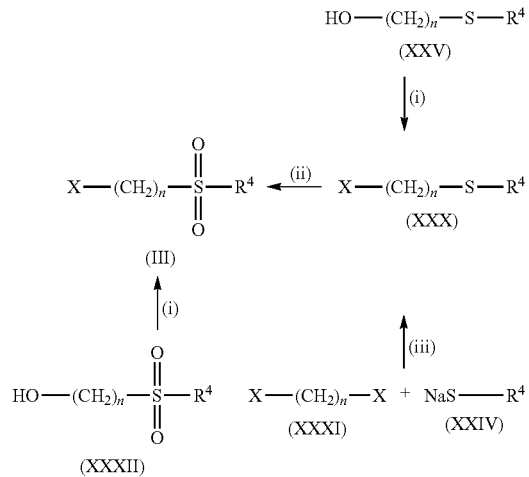

wherein $R^4$ is as defined hereinabove, n represents 1 to 6, $(CH_2)_n$ may be optionally substituted by one $C_{1-3}$alkyl group, and X represents mesylate or tosylate.

Reagents and Conditions: i) suitable activating agent for example methylsulfonyl chloride or p-toluenesulfonyl chloride (both commercially available, for example, from Aldrich), suitable solvent such as pyridine or DCM, optionally at a suitable lowered temperature e.g. from about 0 to 5° C.; ii) suitable solvent such as DCM, appropriate oxidising agent e.g. m-chloroperbenzoic acid; iii) suitable solvent such as DMF, optionally at an appropriate elevated temperature for example from about 70 to 80° C.

Compounds of formula (XXIV) and (XXV) are commercially available, see above (after Scheme 3).

Compounds of formula (XXIV) may also be prepared in situ, by the addition of a suitable base, such as sodium hydride to a solution of the corresponding thiol in a suitable solvent, such as DMF. The suspension may be left for an appropriate amount of time, e.g. about 15 min, before continuing with the reactions described in Scheme 4.

Compounds of formula (XXXI) are commercially available, for example, from Aldrich, and include ethylene di(p-toluenesulfonate), (S)-(−)-1,2-propanediol di-p-tosylate, 1,3-propanediol di-p-tosylate and 1,4-butanediol dimethanesulfonate. Alternatively, compounds of formula (XXXI) may be prepared by methods well known to those skilled in the art, by activation of the corresponding diol. The reaction may typically be carried out using a suitable activating agent such as methanesulfonyl chloride, or p-toluenesulfonyl chloride in a suitable solvent such as DCM or pyridine. Diols corresponding to compounds of formula (XXXI) are commercially available, for example, from Aldrich, and include ethylene glycol, 1,2-butanediol, 1,3-propanediol, 1,3-butanediol, 1,4-butanediol, 1,4-pentanediol, 1,5-pentanediol, 1,5-hexanediol, 3-methyl-1,5-pentanediol and 1,6-hexanediol.

Compounds of formula (XXXII) are commercially available, for example, from Aldrich and/or Alfa Aesar, and include 2-(methylsulfonyl)ethanol and 2-(ethanesulfonyl)ethanol.

In an alternative preparation, the compounds of formula (XXV) which are HO—$(CH_2)_2CH(Y)SR^4$ may be prepared according to Scheme 5 below:

Scheme 5: Synthesis of compounds of formula (XXV), which are HO—$(CH_2)_2CH(Y)SR^4$

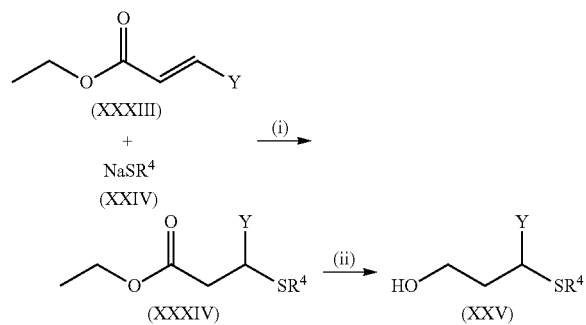

wherein $R^4$ is as defined hereinabove and Y represents hydrogen or $C_{1-3}$alkyl.

Reagents and Conditions: i) suitable solvent such as DMF; ii) suitable solvent such as THF, appropriate reducing agent e.g. lithium aluminium hydride solution in ether, suitable lowered temperature such as from about 0 to 5° C.

The compounds of formula (XXXIII) are commercially available, for example from Aldrich and/or Alfa Aesar and/or Rarechem, and include ethyl acrylate, ethyl crotonate, ethyl trans-2-pentenoate, ethyl 4-methyl-trans-2-pentenoate and ethyl trans-2-hexenoate.

Compounds of formula (XXIV) are commercially available, see above (after Scheme 3).

According to a second process, B, a compound of formula (I) in which $R^2$ represents a saturated 5 to 7 membered ring containing one $SO_2$ group or $R^2$ represents ethylene-$SO_2$—$R^4$ may be prepared by reacting a compound of formula (II)

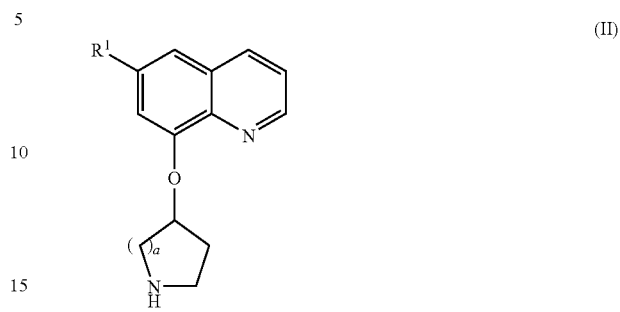

with a compound of formula (IV) or (IVa)

wherein $R^1$, a and $R^4$ are as defined hereinabove and m represents 1 to 3.

The reaction may typically be carried out in a suitable solvent, such as THF or DMF. Optionally, an appropriate base may be added, for example sodium bicarbonate. The reaction is typically heated for example using a microwave oven at a suitable temperature from about 100 to 150° C. for an appropriate time, such as about 15 to 30 min. Alternatively, the heating may be conducted using conventional methods at a suitable elevated temperature, such as from about 70 to 90° C. for longer periods of time, e.g. about 2 to 3 hours or overnight.

Compounds of formula (II) may be prepared according to Scheme 1 above.

Compounds of formula (IV) may be commercially available or may be prepared according to methods disclosed herein. 2,3-dihydrothiophene 1,1-dioxide is commercially available, for example, from AKOS. 3,4-dihydro-2H-thiopyran 1,1-dioxide may be prepared according to the methods disclosed by X-F. Ren, E. Turos, C. H. Lake and M. R. Churchill, J. Org. Chem., 60:6468-6483, (1995), see page 6483. 2,3,4,5-tetrahydrothiepin 1,1-dioxide may be prepared according to the methods disclosed by B. F. Bonini, M. Comes-Franchini, M. Fochi, G. Mazzanti, A. Ricci, Tetrahedron, 52:4803-4816, (1996), see compound 12.

Compounds of formula (IVa) are commercially available, for example, from Aldrich, and include methyl vinyl sulfone, ethyl vinyl sulfone and phenyl vinyl sulfone.

According to a third process, C, a compound of formula (I) in which $R^3$ represents —$N(R^5)SO_2$— may be prepared by reacting a compound of formula (V)

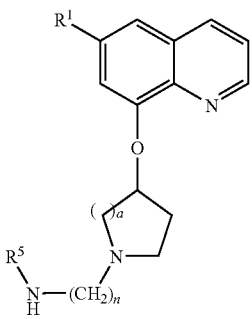

(V)

with a compound of formula (VI)

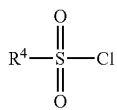

(VI)

wherein $R^1$, a, $R^4$ and $R^5$ are as defined hereinabove, n represents 1 to 6 and $(CH_2)_n$ may be optionally substituted by one $C_{1-3}$alkyl group.

The reaction may typically be carried out using a suitable solvent such as DCM with a suitable base e.g. triethylamine.

Compounds of formula (V) may be prepared according to the following reaction schemes (Schemes 6, 6a and 7).

Compounds of formula (VI) are commercially available, for example, from Aldrich and/or TCI Europe and/or Apollo International and/or Fluorochem, and include methanesulfonyl chloride, ethanesulfonylchloride, 1-propanesulfonyl chloride, iso-propylsulfonyl chloride, 2-methyl-1-propylsulfonyl chloride, 1-butanesulfonyl chloride, sec-butylsulfonyl chloride, n-pentylsulfonyl chloride, 2-pentylsulfonyl chloride, 1-hexanesulfonyl chloride, cyclopentanesulfonyl chloride, cyclohexanesulfonyl chloride, cyclopentylmethanesulfonyl chloride cyclohexylmethanesulfonyl chloride, benzenesulfonyl chloride, 1-naphthalenesulfonyl chloride, 2-naphthalenesulfonyl chloride, 2-anthracenesulfonyl chloride, 4-ethylbenzenesulfonyl chloride, 4-n-propylbenzenesulfonyl chloride, 4-iso-propylbenzenesulfonyl chloride, 4-bromobenzenesulfonyl chloride, 4-iodobenzenesulfonyl chloride, 3-(trifluoromethyl)benzenesulfonyl chloride, 4-cyanobenzenesulfonylchloride, 2,5-dichlorobenzenesulfonyl chloride, 2-chloro-4-cyanobenzenesulfonyl chloride, benzylsulfonyl chloride, 2-(1-naphthyl)ethanesulfonyl chloride, 2-phenyl-ethanesulfonyl chloride, 4-chlorobenzylsulfonyl chloride, 4-methylbenzylsulfonyl chloride, 2-trifluoromethylbenzylsulfonyl chloride and 2-(4-chlorophenyl)-ethanesulfonyl chloride.

Scheme 6: Synthesis of compounds of formula (V) in which n represents 2

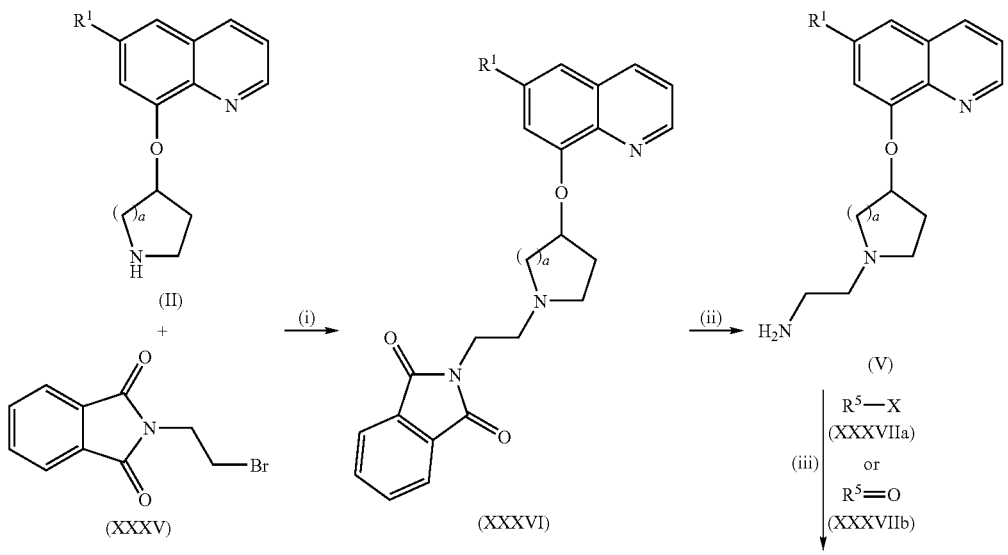

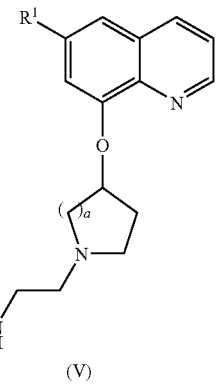

(V)

wherein $R^1$, a and $R^5$ are as defined hereinabove, and X represents a suitable leaving group such as chlorine, broming or iodine.

Reagents and Conditions: i) suitable solvent such as 2-butanone, appropriate base e.g. potassium carbonate, at an elevated temperature such as from about 70 to 90° C.; ii) suitable solvent such as ethanol, hydrazine or hydrazine monohydrate, at an elevated temperature such as from about 70 to 90° C.; iii) 1 equivalent of $R^5$—X (XXXVIIa), in an appropriate solvent such as DMF, suitable base such as triethylamine or sodium hydride, optionally with an activating agent such as sodium iodide; or reductive amination using $R^5$=O (XXXVIIb), in a suitable solvent e.g. DMF, suitable reducing agent such as sodium triacetoxyborohydride.

The compound of formula (XXXV), 2-(2-bromoethyl)-1H-isoindole-1,3(2H)-dione is commercially available, for example from Acros and/or Aldrich.

Compounds of formula (XXXVIIa) are commercially available, for example from Aldrich, and include methyl iodide, iodoethane, 1-iodopropane, 1-iodobutane, 1-iodopentane and 1-iodohexane.

Compounds of formula (XXXVIIb) are commercially available, for example, from Aldrich, and include formaldehyde, acetaldehyde, propionaldehyde, methyl ethyl ketone, butyraldehyde, valeraldehyde, 3-pentanone, hexanal, 3-hexanone and 3-methyl-3-pentanone.

Scheme 6a: Synthesis of compounds of formula (V) in which n represents 2 to 6

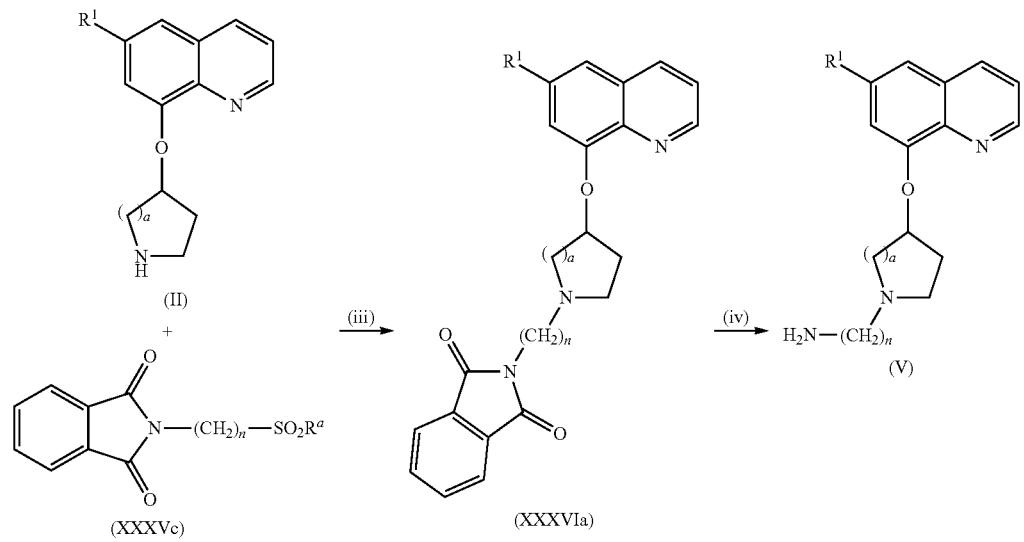

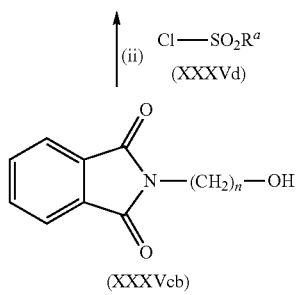

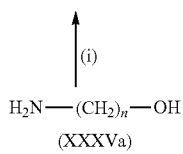

wherein $R^1$ and a are as defined hereinabove, n represents 2 to 6 and $R^a$ represents $C_{1-6}$alkyl.

Reagents and Conditions: i) 2-benzofuran-1,3-dione (commercially available, for example, from Aldrich) in a suitable solvent such as toluene; ii) suitable solvent such as toluene, appropriate base e.g. triethylamine; iii) suitable solvent such as DMF, appropriate base e.g. DIPEA and/or tributylammonium iodide, optionally with an appropriate activating agent e.g. sodium iodide, optionally at an elevated temperature such as from about 70 to 90° C.; iv) suitable solvent such as ethanol, hydrazine or hydrazine monohydrate, at an elevated temperature such as from about 70 to 90° C.

The compounds of formula (XXXVa), are commercially available, for example from Aldrich.

The compounds of formula (XXXVd) are commercially available, for example from Aldrich and/or Fluka.

Scheme 7: Synthesis of compounds of formula (V) in which n represents 3 to 6

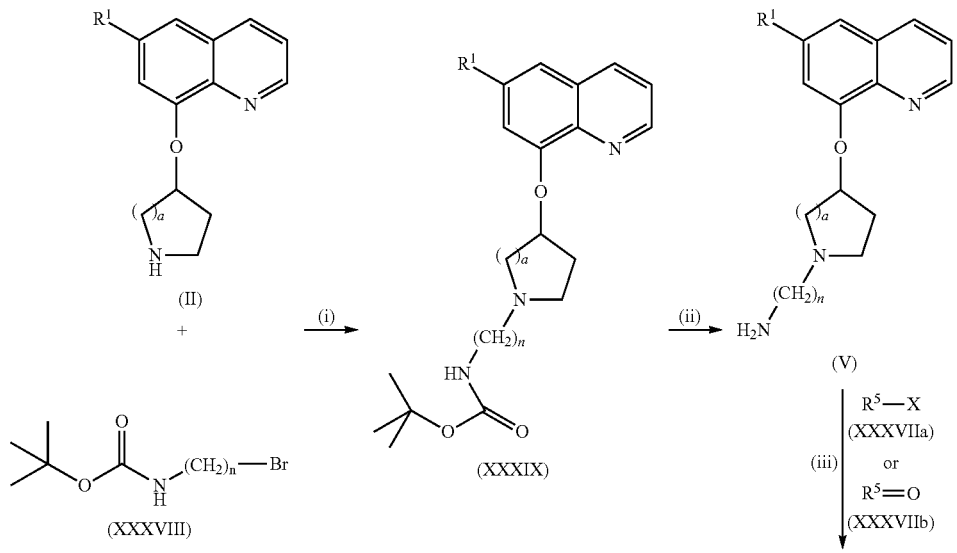

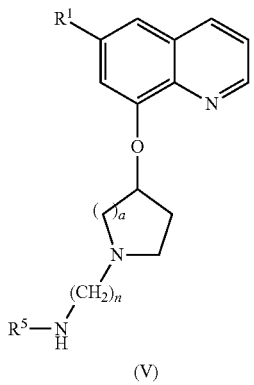

(V)

wherein $R^1$, a and $R^5$ are as defined hereinabove, X represents a suitable leaving group such as chlorine, bromine or iodine, n represents 1 to 6 and $(CH_2)_n$ may be optionally substituted by one $C_{1-3}$alkyl group.

Reagents and Conditions: i) suitable solvent such as 2-butanone, appropriate base e.g. potassium carbonate, at an elevated temperature such as from about 70 to 90° C.; ii) deprotection using a suitable acid such as hydrogen chloride or TFA in a suitable solvent e.g. dioxane or DCM; iii) 1 equivalent of $R^5$—X (XXXVIIa), in an appropriate solvent such as DMF, suitable base such as triethylamine or sodium hydride, optionally with an activating agent such as sodium iodide; or reductive amination using $R^5$=O (XXXVIIb), in a suitable solvent e.g. DMF, suitable reducing agent such as sodium triacetoxyborohydride.

Compounds of formula (XXXVIII) are commercially available, for example, from Aldrich and/or Toronto Chemicals, and include 2-(Boc-amino)ethyl bromide, 3-(Boc-amino)propyl bromide, 4-(Boc-amino)butyl bromide, 5-(Boc-amino)pentyl bromide and 6-(Boc-amino)hexyl bromide.

Compounds of formula (XXXVIIa) and (XXXVIIb) are commercially available, see above (after Scheme 6).

According to a fourth process, D, a compound of formula (I) in which $R^3$ represents —$N(R^5)SO_2$— may be prepared by reacting a compound of formula (II)

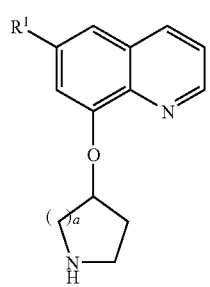

(II)

with a compound of formula (VII)

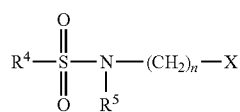

(VII)

wherein $R^1$, a, $R^4$ and $R^5$ are as defined hereinabove, n represents 1 to 6, $(CH_2)_n$ may be optionally substituted by one $C_{1-3}$alkyl group, and X represents a suitable leaving group such as chlorine, bromine, tosylate or mesylate.

The reaction may typically be carried out using a suitable base such as sodium hydrogen carbonate, with an appropriate activating agent e.g. sodium iodide, in a suitable solvent such as DMF. The reaction is typically heated for example, using a microwave oven at an appropriate elevated temperature for example from about 140 to 160° C., for about 10 to 30 minutes, as appropriate. Alternatively, heating may be with conventional apparatus, at elevated temperatures for example from about 50 to 70° C., for about 3 hours to overnight, as appropriate.

Compounds of formula (II) may be prepared according to Scheme 1 above.

Compounds of formula (VII) in which X represents chlorine or bromine are commercially available, for example, from Apollo, and include N-(2-bromoethyl)-4-chlorobenzene-1-sulfonamide, N-(2-bromoethyl)-4-fluorobenzene-1-sulphonamide, N-(2-bromoethyl)-3-(trifluoromethyl)benzene-1-sulphonamide, N-(2-bromoethyl)-2,4-dichlorobenzene sulfonamide and 4-Bromo-N-(3-chloropropyl)benzene sulphonamide.

Compounds of formula (VII) in which X represents mesylate or tosylate may be prepared according to Scheme 8 below.

Scheme 8: Synthesis of compounds of formula (VII) in which X represents mesylate or tosylate

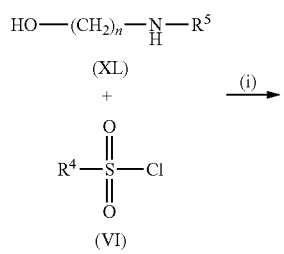

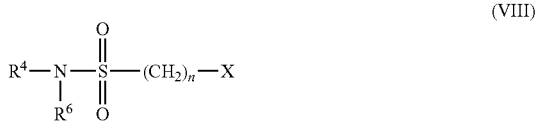

(VII)

wherein $R^4$ and $R^5$ are as defined hereinabove, n represents 1 to 6 and $(CH_2)_n$ may be optionally substituted by one $C_{1-3}$alkyl group.

Reagents and Conditions: i) suitable solvent such as DCM, appropriate base e.g. triethylamine, at a lowered temperature such as from about 0° C. to room temperature.

Compounds of formula (VI) are commercially available, see above (described after process C).

Compounds of formula (XL) are commercially available, for example, from Aldrich and/or TCI Europe, and include 2-aminoethanol, 2-(methylamino)ethanol, 2-(ethylamino) ethanol, 2-(propylamino)ethanol, 2-(butylamino)ethanol, 2-(n-pentylamino)ethanol, 3-amino-1-propanol, 3-(methylamino)-1-propanol, 4-amino-1-butanol, (R)-4-amino-2-methyl-1-butanol, 4-ethylamino-1-butanol, 4-(n-butylamino)-1-butanol, 5-amino-1-pentanol and 6-amino-1-hexanol.

According to a fifth process, E, a compound of formula (I) in which $R^3$ represents —$SO_2N(R^6)$— may be prepared by reacting a compound of formula (II)

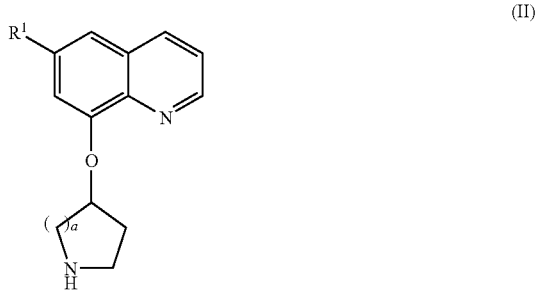

(II)

with a compound of formula (VIII)

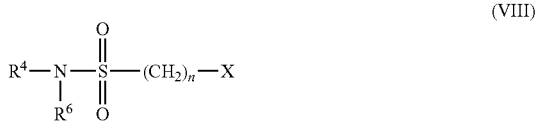

(VIII)

wherein $R^1$, a, $R^4$ and $R^6$ are as defined hereinabove, n represents 1 to 6, $(CH_2)_n$ may be optionally substituted by one $C_{1-3}$alkyl group, and X represents a suitable leaving group such as chlorine or bromine.

The reaction may typically be carried out using a suitable solvent such as DMF with an appropriate activating agent for example, sodium iodide, with a suitable base, e.g. potassium carbonate. The reaction is usually heated using conventional apparatus, at an appropriate elevated temperature for example from about 50 to 70° C., for about 3 hours to overnight, as appropriate.

Compounds of formula (II) may be prepared according to Scheme 1 above.

Compounds of formula (VIII) may be prepared according to Scheme 9 below.

Scheme 9: Synthesis of compounds of formula (VIII) in which X represents chlorine or bromine

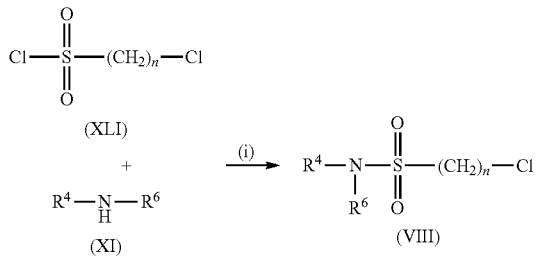

wherein $R^4$ and $R^6$ are as defined hereinabove, n represents 1 to 6 and $(CH_2)_n$ may be optionally substituted by one $C_{1-3}$alkyl group.

Reagents and Conditions: i) suitable solvent such as DCM, at a lowered temperature e.g. from about 0° C. to room temperature.

Compounds of formula (XLI) are commercially available, for example, from Aldrich and/or TCI Europe, and include 2-chloroethanesulfonyl chloride and 3-chloropropanesulfonyl chloride.

Compounds of formula (XI) are commercially available, for example, from Aldrich and/or ABCR and/or Enamine and/or Chembridge, and include methylamine, ethylamine, propylamine, butylamine, (R)-(−)-2-aminobutane, (S)-(+)-2-aminobutanepentylamine, tert-butylamine, 1,1-dimethylpropylamine, hexylamine, dimethylamine, N-ethylmethylamine, N-methylpropylamine, diethylamine, dipropylamine, N-ethylbutylamine, dibutylamine, dipentylamine, dihexylamine, cyclopentylamine, cyclohexylamine, 2-methylcyclohexylamine, cycloheptylamine, N-methylcyclohexylamine, N-isopropylcyclohexyamine, N-cycloheptyl-N-methylamine, N-(sec-butyl)cycloheptanamine, N-(1-ethylpropyl)cycloheptanamine, N-isopropylcycloheptanamine, cyclohexanemethylamine, cycloheptanemethylamine, 2-cyclohexylethylamine, aniline, 9-aminophenanthrene, 1-aminoanthracene, 2-aminobenzonitrile, 2-fluoroaniline, 4-chloroaniline, 3-bromoaniline, 3-iodoaniline, 1-amino-2-methylnaphthalene, 2-methylaniline, 3-ethylaniline, 4-propylaniline, 2-isopropylaniline, 2-aminobenzotrifluoride, 3,5-bis(trifluoromethyl)aniline, 3-amino-4-fluorobenzotrifluoride, 5-fluoro-2-methylaniline, N-ethyl-1-naphthalene, N-methylaniline, N-ethylaniline, N-butylaniline, N-hexylaniline, N-ethyl-3-methylaniline, benzylamine, 2-phenylethylamine, 2-(3-chlorophenyl)ethylamine, 3-phenylpropylamine, (3-phenylpropyl)methylamine, N-methylphenethylamine, (2-phenylethyl)propylamine, cyclopentylamine, cyclohexylamine, cycloheptylamine, morpholine, thiomorphline, piperazine and N-methylpiperazine.

According to a sixth process, F, a compound of formula (I) in which $R^3$ represents —$N(R^7)C(O)N(R^8)$—, and $R^3$ represents hydrogen, may be prepared by reacting a compound of formula (Va)

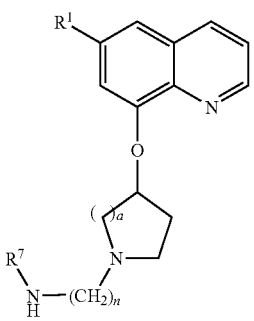

(Va)

with a compound of formula (IX)

$$R^4\text{—}N\text{=}C\text{=}O \qquad (IX)$$

wherein $R^1$, a, $R^4$ and $R^7$ are as defined hereinabove, n represents 1 to 6 and $(CH_2)_n$ may be optionally substituted by one $C_{1-3}$alkyl group.

The reaction may typically be carried out using a suitable solvent, such as DCM. The reaction is usually carried out at ambient temperature for an appropriate length of time such as overnight, for example.

Compounds of formula (Va) may be prepared according to Schemes 6 and 7 above, in which $R^5$ is $R^7$.

Compounds of formula (IX) are commercially available, for example, from Aldrich, and include ethyl isocyanate, isopropyl isocyanate, propyl isocyanate, butyl isocyanate, sec-butyl isocyanate, tert-butyl isocyanate, pentyl isocyanate, hexyl isocyanate, cyclopentyl isocyanate, cyclohexyl isocyanate, cycloheptyl isocyanate, cyclohexanemethyl isocyanate, (R)-(−)-1-cyclohexylethyl isocyanate, phenyl isocyanate, 3-chlorophenyl isocyanate, 2-fluoro-phenyl isocyanate, 2-bromophenyl isocyanate, 4-iodophenyl isocyanate, 4-methylphenyl isocyanate, 2-ethylphenyl isocyanate, 2-isopropylphenyl isocyanate, 2-(trifluoromethyl)phenyl isocyanate, 3-cyanophenyl isocyanate, 2,3-dimethylphenyl isocyanate, 3-chloro-4-methylphenyl isocyanate, 4-bromo-2-(trifluoromethyl)phenyl isocyanate, 2-isopropyl-6-methylphenyl isocyanate, benzyl isocyanate, phenethyl isocyanate, 3-phenylpropyl isocyanate, (S)-(−)-1-phenylpropyl isocyanate, 3-methylbenzyl isocyanate, 4-fluorobenzyl isocyanate, 2,4-dichlorobenzyl isocyanate and 4-ethylphenethyl isocyanate.

According to a seventh process, G, a compound of formula (I) in which $R^3$ represents —N($R^7$)C(O)N($R^8$)— may be prepared by reacting a compound of formula (X)

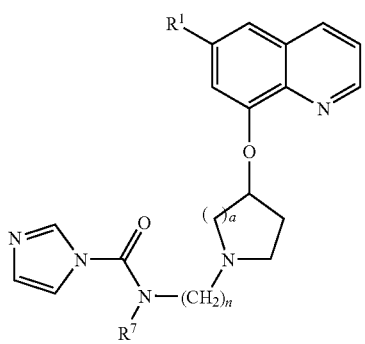

(X)

with a compound of formula (XIa)

$$R^4\text{—}\underset{H}{N}\text{—}R^8 \qquad (XIa)$$

wherein $R^1$, a, $R^4$, $R^7$ and $R^8$ are as defined hereinabove, n represents 1 to 6 and $(CH_2)_n$ may be optionally substituted by one $C_{1-3}$alkyl group.

The reaction may typically be carried out in a suitable solvent such as THF or DCM, usually at an elevated temperature for example at reflux.

Compounds of formula (X) may be prepared according to Scheme 10 below.

Compounds of formula (XIa) are commercially available, for which see compounds of formula (XI) in which $R^6$ is $R^3$ (see after Scheme 9, above).

Scheme 10: Synthesis of compounds of formula (X)

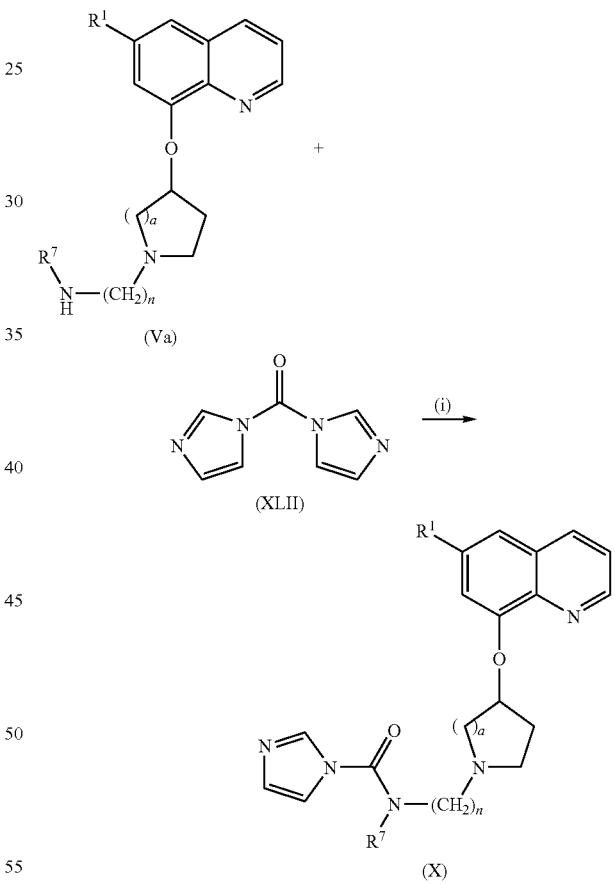

wherein $R^1$, a and $R^7$ are as defined hereinabove, n represents 1 to 6 and $(CH_2)_n$ may be optionally substituted by one $C_{1-3}$alkyl group.

Reagents and Conditions: i) 1 equivalent 1,1'-carbonyldiimidazole, in an appropriate solvent such as THF or DCM.

Compounds of formula (Va) may be prepared according to Schemes 6 and 7 above, in which $R^5$ is $R^7$.

The compound of formula (XLII), 1,1'-carbonyldiimidazole, is commercially available, for example, from Aldrich.

According to an eighth process, H, a compound of formula (I), may be prepared by interconversion from other compounds of formula (I).

Interconversions include, but are not limited to alkylation and deprotection, under standard conditions well known to those skilled in the art.

Thus, typically, an alkylation reaction may be carried out between a compound of formula (I) and a $C_{1-6}$alkyl, activated to substitution by means of a leaving group such as halogen, such as chlorine or bromine, or an activated hydroxyl group, such as mesylate or tosylate. The reaction usually takes place in the presence of a suitable base such as triethylamine, N,N'-diisopropylethylamine or sodium hydride, in an appropriate solvent such as 2-butanone or DMF, optionally at an appropriate elevated temperature such as at about 80° C.

According to a ninth process, I, a salt of a compound of formula (I) may be prepared by exchange of counterions, or precipitation of said salt from the free base.

Compounds of formula (I) may be further purified by methods well-known to those skilled in the art, for example by recrystallisation, column chromatography (which may be manual or automated, for example mass-directed), preparative TLC and the like. A suitable solvent system for recrystallisation of compounds of formula (I) in which $R^3$ represents —$N(R^5)SO_2$— and $R^4$ represents $C_{1-6}$alkyl is methanol/ethyl acetate.

Examples of protecting groups that may be employed in the synthetic routes described and the means for their removal can be found in T. W. Greene et al. 'Protective Groups in Organic Synthesis' (3rd edition, J. Wiley and Sons, 1999). Suitable amine protecting groups include sulfonyl (e.g. tosyl), acyl (e.g. acetyl, 2',2',2'-trichloroethoxycarbonyl, benzyloxycarbonyl or t-butoxycarbonyl) and arylalkyl (e.g. benzyl), which may be removed by hydrolysis (e.g. using an acid such as hydrogen chloride in dioxane or trifluoroacetic acid in dichloromethane) or reductively (e.g. hydrogenolysis of a benzyl group or reductive removal of a 2',2',2'-trichloroethoxycarbonyl group using zinc in acetic acid) as appropriate. Other suitable amine protecting groups include trifluoroacetyl (—$COCF_3$), which may be removed by base catalysed hydrolysis or a solid phase resin bound benzyl group, such as a Merrifield resin bound 2,6-dimethoxybenzyl group (Ellman linker), which may be removed by acid cleavage, for example with trifluoroacetic acid.

It will be appreciated that novel intermediates described herein form another embodiment of the present invention.

Examples of disease states in which a compound of formula (I), or a pharmaceutically acceptable salt thereof potentially may have beneficial anti-inflammatory and/or anti-allergic effects include inflammatory and/or allergic diseases of the respiratory tract, such as allergic rhinitis (seasonal and perennial) or other diseases such as bronchitis (including chronic bronchitis), asthma (including allergen-induced asthmatic reactions), chronic obstructive pulmonary disease (COPD) and sinusitis.

Furthermore, the compounds of formula (I) may be of use in the treatment of nephritis, skin diseases such as psoriasis, eczema, allergic dermatitis and hypersensitivity reactions. Also, the compounds of formula (I) may be useful in the treatment of insect bites and stings.

The compounds of formula (I) may also be of use in the treatment of nasal polyposis, conjunctivitis (e.g allergic conjunctivitis) or pruritus.

A disease of particular interest is allergic rhinitis.

Other diseases in which histamine may have a pathophysiological role include non-allegic rhinitis, and also diseases of the gastrointestinal tract such as intestinal inflammatory diseases including inflammatory bowel disease (e.g. Crohn's disease or ulcerative colitis) and intestinal inflammatory diseases secondary to radiation exposure or allergen exposure.

It will be appreciated by those skilled in the art that references herein to treatment or therapy may extend to prophylaxis as well as the treatment of established conditions.

As mentioned above, compounds of formula (I) may be useful as therapeutic agents. There is thus provided a compound of formula (I) or a pharmaceutically acceptable salt thereof for use in therapy.

In another embodiment, there is provided a compound which is 6-butyl-8-({1-[3-(ethylsulfonyl)propyl]-4-piperidinyl}oxy)quinoline, or a pharmaceutically acceptable salt thereof for use in therapy.

In another embodiment, there is provided a compound which is N-(4-{4-[(6-butyl-8-quinolinyl)oxy]-1-piperidinyl}butyl)ethanesulfonamide, or a pharmaceutically acceptable salt (such as the dihydrochloride salt) thereof for use in therapy.

In another embodiment, there is provided a compound of formula (I) or a pharmaceutically acceptable salt thereof for use in the treatment of any of the above diseases (e.g. allergic rhinitis).

In another embodiment, there is provided a compound which is 6-butyl-8-({1-[3-(ethylsulfonyl)propyl]-4-piperidinyl}oxy)quinoline, or a pharmaceutically acceptable salt thereof for use in the treatment of any of the above diseases (e.g. allergic rhinitis).

In another embodiment, there is provided a compound which is N-(4-{4-[(6-butyl-8-quinolinyl)oxy]-1-piperidinyl}butyl)ethanesulfonamide, or a pharmaceutically acceptable salt (such as the dihydrochloride salt) thereof for use in the treatment of any of the above diseases (e.g. allergic rhinitis).

In another embodiment, there is provided the use of a compound of formula (I) or a pharmaceutically acceptable salt thereof for the manufacture of a medicament for the treatment of any of the above diseases (e.g. allergic rhinitis).

In another embodiment, there is provided the use of a compound which is 6-butyl-8-({1-[3-(ethylsulfonyl)propyl]-4-piperidinyl}oxy)quinoline, or a pharmaceutically acceptable salt thereof for the manufacture of a medicament for the treatment of any of the above diseases (e.g. allergic rhinitis).

In another embodiment, there is provided the use of a compound which is N-(4-{4-[(6-butyl-8-quinolinyl)oxy]-1-piperidinyl}butyl)ethanesulfonamide, or a pharmaceutically acceptable salt (such as the dihydrochloride salt) thereof for the manufacture of a medicament for the treatment of any of the above diseases (e.g. allergic rhinitis).

In another embodiment, there is provided a method for the treatment (or prophylaxis) of any of the above diseases (for example inflammatory and/or allergic diseases of the respiratory tract, e.g. allergic rhinitis), in a patient in need thereof, which method comprises administering an effective amount of a compound of formula (I) or a pharmaceutically acceptable salt thereof.

In another embodiment, there is provided a method for the treatment (or prophylaxis) of any of the above diseases (for example inflammatory and/or allergic diseases of the respiratory tract, e.g. allergic rhinitis), in a patient in need thereof, which method comprises administering an effective amount of a compound which is 6-butyl-8-({1-[3-(ethylsulfonyl)propyl]-4-piperidinyl}oxy)quinoline, or a pharmaceutically acceptable salt thereof.

In another embodiment, there is provided a method for the treatment (or prophylaxis) of any of the above diseases (for example inflammatory and/or allergic diseases of the respiratory tract, e.g. allergic rhinitis), in a patient in need thereof, which method comprises administering an effective amount of a compound which is N-(4-{4-[(6-butyl-8-quinolinyl) oxy]-1-piperidinyl}butyl)ethanesulfonamide, or a pharmaceutically acceptable salt (such as the dihydrochloride salt) thereof.

When used in therapy, the compounds of formula (I) or pharmaceutically acceptable salts thereof may typically be formulated in a suitable pharmaceutical composition. Such pharmaceutical compositions may be prepared using standard procedures.

Thus, there is provided a composition which comprises a compound of formula (I) or a pharmaceutically acceptable salt thereof and one or more (e.g. 10 or fewer) pharmaceutically acceptable carriers and/or excipients.

In another embodiment, there is provided a composition which comprises a compound which is 6-butyl-8-({1-[3-(ethylsulfonyl)propyl]-4-piperidinyl}oxy)quinoline, or a pharmaceutically acceptable salt thereof and one or more pharmaceutically acceptable carriers and/or excipients.

In another embodiment, there is provided a composition which comprises a compound which is N-(4-{4-[(6-butyl-8-quinolinyl)oxy]-1-piperidinyl}butyl)ethanesulfonamide, or a pharmaceutically acceptable salt (such as the dihydrochloride salt) thereof and one or more pharmaceutically acceptable carriers and/or excipients.

A composition comprising a compound of formula (I) or a pharmaceutically acceptable salt thereof, which may be prepared by admixture, suitably at ambient temperature and atmospheric pressure, may be suitable for topical administration (which includes epicutaneous, inhaled, intranasal or ocular administration), enteral administration (which includes oral or rectal administration) or parenteral administration (such as by injection or infusion). Of interest are compositions comprising a compound of formula (I) or a pharmaceutically acceptable salt thereof, suitable for topical administration, particularly suitable for intranasal administration.

Generally, compositions may be in the form of solutions or suspensions (aqueous or non-aqueous), tablets, capsules, oral liquid preparations, powders, granules, lozenges, lotions, creams, ointments, gels, foams, reconstitutable powders or suppositories as required by the route of administration.

Generally, the compositions comprising a compound of formula (I) or a pharmaceutically acceptable salt thereof may contain from about 0.001 to 99% (w/w), or about 0.1 to 99% (w/w), such as from about 0.1 to 60% (w/w), or about 10 to 60% (w/w), or about 0.01% to 2% (w/w) (based on the total weight of the composition), of the compound of formula (I) or the pharmaceutically acceptable salt thereof, depending on the route of administration. The dose of the compound used in the treatment of the aforementioned diseases will vary in the usual way with the seriousness of the diseases, the weight of the sufferer, and other similar factors. However, as a general guide, suitable unit doses may be about 0.05 to 1000 mg, for example about 0.05 to 200 mg, for example about 0.05 to 2 mg, or about 0.05 to 1 mg and such unit doses may be administered more than once a day, for example two or three times a day or as desired. Such therapy may extend for a number of weeks or months.

The proportion of the compound of formula (I) or a pharmaceutically acceptable salt thereof in a topical composition will depend on the precise type of composition to be prepared and the particular route of administration, but will generally be within the range of from about 0.001 to 10% (w/w), based on the total weight of the composition. Generally, however for most types of preparations the proportion used will be within the range of from about 0.005 to 1% (w/w), such as about 0.01 to 1% (w/w), or about 0.025 to 0.9% (w/w) (based on the total weight of the composition). However, in powders for inhalation the proportion used will generally be within the range of from about 0.1 to 5% (w/w), based on the total weight of the composition.

Generally, compositions suitable for intranasal or inhaled administration may conveniently be formulated as aerosols, solutions, suspensions, drops, gels or dry powders, optionally with one or more pharmaceutically acceptable carriers and/or excipients such as aqueous or non-aqueous vehicles, thickening agents, isotonicity adjusting agents, antioxidants, preservatives and/or co-solvents.

For compositions suitable for intranasal or inhaled administration, the compound of formula (I) or a pharmaceutically acceptable salt thereof may typically be in a particle-size-reduced form, which may be prepared by conventional techniques, for example, micronisation, milling and/or microfluidisation. Generally, the size-reduced (e.g. micronised) compound of formula (I) or a pharmaceutically acceptable salt thereof can be defined by a $D_{50}$ value of about 0.5 to 10 microns, for example of about 1 to 10 microns, such as of about 2 to 4 microns (for example as measured using laser diffraction).

In one embodiment, compositions comprising a compound of formula (I) or a pharmaceutically acceptable salt thereof are suitable for intranasal administration. Intranasal compositions comprising a compound of formula (I) or a pharmaceutically acceptable salt thereof may permit the compound(s) to be delivered to all areas of the nasal cavities (the target tissue) and further, may permit the compound(s) to remain in contact with the target tissue for longer periods of time. A suitable dosing regime for intranasal compositions would be for the patient to inhale slowly through the nose subsequent to the nasal cavity being cleared. During inhalation the composition would be administered to one nostril while the other is manually compressed. This procedure would then be repeated for the other nostril. Typically, one or two administrations per nostril would be administered by the above procedure up to two or three times each day, ideally once daily. Of particular interest are intranasal compositions suitable for once daily administration.

The intranasal compositions containing a compound of formula (I) or a pharmaceutically acceptable salt thereof may be in the form of an aqueous suspension and/or an aqueous solution. Partial suspensions and/or partial solutions are encompassed within the scope of the present invention. Compositions comprising one compound which is in solution and another compound which is in suspension are also included within the scope of the present invention.

Intranasal compositions may optionally contain one or more suspending/thickening agents, one or more preservatives, one or more wetting agents, one or more isotonicity adjusting agents and/or one or more co-solvents as desired. Compositions suitable for intranasal administration may optionally further contain other excipients, such as antioxidants (for example sodium metabisulphite), taste-masking agents (such as menthol) and sweetening agents (for example dextrose, glycerol, saccharin and/or sorbitol).

The skilled person would readily appreciate that some excipients may perform more than one function, depending on the nature and number of excipients used in the composition and the particular properties of the therapeutic compound(s) and other carriers and/or excipients contained therein.

The suspending/thickening agent(s), if included, will typically be present in the intranasal composition in an amount of between about 0.1 and 5% (w/w), such as between about 1.5% and 2.4% (w/w), particularly about 2.4% (w/w) based on the total weight of the composition. Examples of suspending agents include, but are not limited to Avicel® (microcrystalline cellulose and carboxymethylcellulose sodium), carboxymethylcellulose sodium, veegum, tragacanth, bentonite, methylcellulose, xanthan gum, carbopol and polyethylene glycols. In one embodiment, an intranasal composition containing a compound of formula (I) or a pharmaceutically acceptable salt thereof comprises a suspending/thickening agent which is microcrystalline cellulose and carboxymethylcellulose sodium. Suspending agents may also be included in compositions suitable for inhaled, ocular and oral administration as appropriate.

For stability purposes, intranasal compositions comprising a compound of formula (I) or a pharmaceutically acceptable salt thereof may be protected from microbial or fungal contamination and growth by inclusion of a preservative. Examples of pharmaceutically acceptable anti-microbial agents or preservatives include, but are not limited to quaternary ammonium compounds (e.g. benzethonium chloride, cetrimide, cetylpyridinium chloride, myristal picolinium chloride and lauralkonium chloride. Another anti-microbial agent is benzalkonium chloride), mercurial agents (e.g. phenylmercuric nitrate, phenylmercuric acetate and thimerosal), alcoholic agents (e.g. chlorobutanol, phenylethyl alcohol and benzyl alcohol), antibacterial esters (e.g. esters of para-hydroxybenzoic acid), chelating agents such as disodium ethylenediaminetetraacetate (EDTA) and other anti-microbial agents such as chlorhexidine, chlorocresol, sorbic acid and its salts (such as potassium sorbate) and polymyxin. Examples of pharmaceutically acceptable anti-fungal agents or preservatives may include, but are not limited to, sodium benzoate, sorbic acid, sodium propionate, methyl paraben, ethyl paraben, propyl paraben and butyl paraben. The preservative, if included, may be present in an amount of between about 0.001 and 1% (w/w), such as about 0.015% (w/w), and for example between about 0.015% to 0.5% (w/w) or between about 0.015 to 0.3% (w/w), based on the total weight of the composition. In one embodiment, an intranasal composition containing a compound of formula (I) or a pharmaceutically acceptable salt thereof comprises a preservative which is selected from EDTA and/or potassium sorbate. Preservatives may be included in compositions suitable for other routes of administration as appropriate.

Compositions which contain a suspended medicament may include a pharmaceutically acceptable wetting agent which functions to wet the particles of medicament to facilitate dispersion thereof in the aqueous phase of the composition. Typically, the amount of wetting agent used will not cause foaming of the dispersion during mixing. Examples of wetting agents include, but are not limited to fatty alcohols, esters and ethers, such as polyoxyethylene (20) sorbitan monooleate (Polysorbate 80), macrogol ethers and poloxamers. The wetting agent may be present in intranasal compositions in an amount of between about 0.005 to 0.05% (w/w), such as between about 0.001 and 0.05% (w/w), for example about 0.025% (w/w), based on the total weight of the composition. In one embodiment, an intranasal composition containing a compound of formula (I) or a pharmaceutically acceptable salt thereof comprises a wetting agent which is polyoxyethylene (20) sorbitan monooleate (Polysorbate 80). Wetting agents may be included in compositions suitable for other routes of administration, e.g. for inhaled and/or ocular administration, as appropriate.

An isotonicity adjusting agent may be included to achieve isotonicity with body fluids e.g. fluids of the nasal cavity, resulting in reduced levels of irritancy. Examples of isotonicity adjusting agents include, but are not limited to sodium chloride, dextrose, xylitol and calcium chloride. An isotonicity adjusting agent may be included in intranasal compositions in an amount of between about 0.1 and 10% (w/w), for example between about 4.5 to 5.5% (w/w), such as about 5.0% (w/w), or between about 0.5 to 1% (w/w), or about 0.75% (w/w), based on the total weight of the composition. In one embodiment, an intranasal composition containing a compound of formula (I) or a pharmaceutically acceptable salt thereof comprises an isotonicity adjusting agent which is xylitol. In another embodiment, the intranasal composition does not contain an isotonicity adjusting agent. Isotonicity adjusting agents may also be included in compositions suitable for other routes of administration, for example in compositions suitable for inhaled, ocular, oral liquid and parenteral administration, as appropriate.

One or more co-solvent(s) may be included to aid solubility of the active compound(s) and/or other excipients. Examples of pharmaceutically acceptable co-solvents include, but are not limited to, propylene glycol, dipropylene glycol, ethylene glycol, glycerol, ethanol, polyethylene glycols (for example PEG300 or PEG400) and methanol. The co-solvent(s), if present, may be included in an amount of from about 0.05 to 20% (w/w), such as from about 1.5 to 17.5% (w/w), or from about 1.5 to 7.5% (w/w), or from about 0.05% to 0.5% (w/w) based on the total weight of the composition. In one embodiment, an intranasal composition containing a compound of formula (I) or a pharmaceutically acceptable salt thereof comprises a co-solvent which is propylene glycol. Co-solvents may also be included in compositions suitable for other routes of administration, as appropriate.

Further, the intranasal compositions comprising a compound of formula (I) or a pharmaceutically acceptable salt thereof may be buffered by the addition of suitable buffering agents such as sodium citrate, citric acid, trometarol, phosphates such as disodium phosphate (for example the dodecahydrate, heptahydrate, dihydrate and anhydrous forms) or sodium phosphate and mixtures thereof. In one embodiment, an intranasal composition containing a compound of formula (I) or a pharmaceutically acceptable salt thereof comprises buffering agents which are sodium citrate and/or citric acid. Buffering agents may also be included in compositions suitable for other routes of administration as appropriate.

In one embodiment, there is provided an intranasal aqueous composition containing a compound of formula (I) or a pharmaceutically acceptable salt thereof and further comprising
a) a suspending/thickening agent;
b) a preservative;
c) a wetting agent;
d) a co-solvent; and optionally
e) an isotonicity adjusting agent.

Compositions for administration topically to the nose (for example, for the treatment of rhinitis) or to the lung, include pressurised aerosol compositions and aqueous compositions delivered to the nasal cavities by pressurised pump. Compositions which are non-pressurised and are suitable for administration topically to the nasal cavity are of particular interest. Suitable compositions contain water as the diluent or carrier for this purpose. Aqueous compositions for administration to the lung or nose may be provided with conventional excipients such as buffering agents, tonicity modifying agents and the like. Aqueous compositions may also be administered to the nose by nebulisation.

A fluid dispenser may typically be used to deliver a fluid composition to the nasal cavities. The fluid composition may be aqueous or non-aqueous, but typically aqueous. Such a fluid dispenser may have a dispensing nozzle or dispensing orifice through which a metered dose of the fluid composition is dispensed upon the application of a user-applied force to a pump mechanism of the fluid dispenser. Such fluid dispensers are generally provided with a reservoir of multiple metered doses of the fluid composition, the doses being dispensable upon sequential pump actuations. The dispensing nozzle or orifice may be configured for insertion into the nostrils of the user for spray dispensing of the fluid composition into the nasal cavity. A fluid dispenser of the aforementioned type is described and illustrated in WO05/044354 the entire content of which is hereby incorporated herein by reference. The dispenser has a housing which houses a fluid discharge device having a compression pump mounted on a container for containing a fluid composition. The housing has at least one finger-operable side lever which is movable inwardly with respect to the housing to cam the container upwardly in the housing to cause the pump to compress and pump a metered dose of the composition out of a pump stem through a nasal nozzle of the housing. In one embodiment, the fluid dispenser is of the general type illustrated in FIGS. 30-40 of WO05/044354.

Aqueous compositions containing a compound of formula (I) or a pharmaceutically acceptable salt thereof may also be delivered by a pump as disclosed in WO2007/138084, for example as disclosed with reference to FIGS. 22-46 thereof, or as disclosed in GB0723418.0, for example as disclosed with reference to FIGS. 7-32 thereof, both of which prior patent applications are incorporated herein by reference in their entirety. The pump may be actuated by an actuator as disclosed in FIGS. 1-6 of said GB0723418.0.

In one embodiment, there is provided an intranasal composition comprising a compound of formula (I) or a pharmaceutically acceptable salt thereof. In another embodiment, such an intranasal composition is benzalkonium chloride-free.

In another embodiment, there is provided an intranasal composition comprising a compound which is N-(4-{4-[(6-butyl-8-quinolinyl)oxy]-1-piperidinyl}butyl)ethanesulfonamide, or a pharmaceutically acceptable salt (such as a dihydrochloride salt) thereof. In another embodiment, such an intranasal composition is benzalkonium chloride-free.

Inhaled administration involves topical administration to the lung, such as by aerosol or dry powder composition.

Aerosol compositions suitable for inhaled administration may comprise a solution or fine suspension of the compound in a pharmaceutically acceptable aqueous or non-aqueous solvent. Aerosol compositions suitable for inhalation can be either a suspension or a solution and generally contain a compound of formula (I) or a pharmaceutically acceptable salt thereof and a suitable propellant such as a fluorocarbon or hydrogen-containing chlorofluorocarbon or mixtures thereof, such as hydrofluoroalkanes, e.g. 1,1,1,2-tetrafluoroethane, 1,1,1,2,3,3,3-heptafluoro-n-propane or a mixture thereof. The aerosol composition may optionally contain additional excipients well known in the art such as surfactants or co-solvents. Examples of surfactants include, but are not limited to oleic acid, lecithin, an oligolactic acid or derivative e.g. as described in WO94/21229 and WO98/34596. An example of a co-solvent includes, but is not limited to ethanol. Aerosol compositions may be presented in single or multi-dose quantities in sterile form in a sealed container, which may take the form of a cartridge or refill for use with an atomising device or inhaler. Alternatively, the sealed container may be a unitary dispensing device such as a single dose nasal inhaler or an aerosol dispenser fitted with a metering valve (metered dose inhaler), which is intended for disposal once the contents of the container have been exhausted.

Dry powder inhalable compositions may take the form of capsules and cartridges of, for example, gelatine, or blisters of, for example, laminated aluminium foil, for use in an inhaler or insufflator. Such compositions may be formulated comprising a powder mix of a compound of formula (I) or a pharmaceutically acceptable salt thereof and a suitable powder base such as lactose or starch.

Optionally, for dry powder inhalable compositions, a composition suitable for inhaled administration may be incorporated into a plurality of sealed dose containers (e.g. comprising the dry powder composition) mounted longitudinally in a strip or ribbon inside a suitable inhalation device. The container is rupturable or peel-openable on demand and the dose of e.g. the dry powder composition may be administered by inhalation via the device such as the DISKUS™ device, marketed by GlaxoSmithKline. The DISKUS™ inhalation device is for example described in GB 2242134 A, and in such a device, at least one container for the composition in powder form (the container or containers may, for example, be a plurality of sealed dose containers mounted longitudinally in a strip or ribbon) is defined between two members peelably secured to one another; the device comprises: a means of defining an opening station for the said container or containers; a means for peeling the members apart at the opening station to open the container; and an outlet, communicating with the opened container, through which a user can inhale the composition in powder form from the opened container.

Aerosol compositions are typically arranged so that each metered dose or "puff" of aerosol contains about 20 µg-2000 µg, particularly about 20 µg-500 µg of a compound of formula (I) or a pharmaceutically acceptable salt thereof. Administration may be once daily or several times daily, for example 2, 3, 4 or 8 times, giving for example 1, 2 or 3 doses each time. The overall daily dose with an aerosol will be within the range of about 100 µg-10 mg, such as between about 200 µg-2000 µg. The overall daily dose and the metered dose delivered by capsules and cartridges in an inhaler or insufflator will generally be double those with aerosol compositions.

In another embodiment, there is provided a composition comprising a compound of formula (I) or a pharmaceutically acceptable salt thereof which is suitable for epicutaneous administration. An epicutaneous composition to be applied to the affected area e.g. the skin, by one or more application per day, may be in the form of, for example, an ointment, a cream, an emulsion, a lotion, a foam, a spray, an aqueous gel, or a microemulsion. Such compositions may optionally contain one or more solubilising agents, skin-penetration-enhancing agents, surfactants, fragrances, preservatives or emulsifying agents.

Ointments, creams and gels, may, for example, be formulated with an aqueous or oily base with the addition of suitable thickening and/or gelling agent and/or solvents. Such bases may thus, for example, include water and/or an oil such as liquid paraffin or a vegetable oil such as arachis oil or castor oil, or a solvent such as polyethylene glycol. Thickening agents and gelling agents which may be used according to the nature of the base include soft paraffin, aluminium stearate, cetostearyl alcohol, polyethylene glycols, woolfat, beeswax, carboxypolymethylene and cellulose derivatives, and/or glyceryl monostearate and/or non-ionic emulsifying agents. Lotions may be formulated with an aqueous or oily base and will in general also contain one or more emulsifying agents, stabilising agents, dispersing agents, suspending agents or thickening agents.

In another embodiment, there is provided a composition comprising a compound of formula (I) or a pharmaceutically acceptable salt thereof which is suitable for ocular administration. Such compositions may optionally contain one or more suspending agents, one or more preservatives, one or more wetting/lubricating agents and/or one or more isotonicity adjusting agents. Examples of ophthalmic wetting/lubricating agents may include cellulose derivatives, dextran 70, gelatin, liquid polyols, polyvinyl alcohol and povidone such as cellulose derivatives and polyols.

In another embodiment, there is provided a composition comprising a compound which is N-(4-{4-[(6-butyl-8-quinolinyl)oxy]-1-piperidinyl}butyl)ethanesulfonamide, or a pharmaceutically acceptable salt (such as a dihydrochloride salt) thereof which is suitable for ocular administration.

In another embodiment, there is provided a composition comprising a compound of formula (I) or a pharmaceutically acceptable salt thereof which is suitable for oral administration. Tablets and capsules for oral administration may be in unit dose form, and may contain conventional excipients, such as binding agents, fillers, tabletting lubricants, disintegrants and acceptable wetting agents. The tablets may be coated according to methods well known in normal pharmaceutical practice.

Oral liquid preparations may be in the form of, for example, aqueous or oily suspension, solutions, emulsions, syrups or elixirs, or may be in the form of a dry product for reconstitution with water or other suitable vehicle before use. Such liquid preparations may contain conventional additives such as suspending agents, emulsifying agents, non-aqueous vehicles (which may include edible oils), preservatives, and, if desired, conventional flavourings or colorants.

In another embodiment, there is provided a composition comprising a compound of formula (I) or a pharmaceutically acceptable salt thereof which is suitable for parenteral administration. Fluid unit dosage forms suitable for parenteral administration may be prepared utilising a compound of formula (I) or pharmaceutically acceptable salt thereof and a sterile vehicle which may be aqueous or oil based. The compound, depending on the vehicle and concentration used, may be either suspended or dissolved in the vehicle. In preparing solutions, the compound may be dissolved for injection and filter sterilised before filling into a suitable vial or ampoule and sealing. Optionally, adjuvants such as a local anaesthetic, preservatives and buffering agents may be dissolved in the vehicle. To enhance the stability, the composition may be frozen after filling into the vial and the water removed under vacuum. The lyophilised parenteral composition may be reconstituted with a suitable solvent just prior to administration. Parenteral suspensions may be prepared in substantially the same manner, except that the compound is suspended in the vehicle instead of being dissolved, and sterilisation cannot be accomplished by filtration. The compound may be sterilised by exposure to ethylene oxide before suspension in a sterile vehicle. A surfactant or wetting agent may be included in the composition to facilitate uniform distribution of the compound.

The compounds and pharmaceutical compositions according to the invention may also be used in combination with or include one or more (e.g. one or two) other therapeutic agents, for example other antihistaminic agents for example H4 or H3 receptor antagonists, anticholinergic agents, anti-inflammatory agents such as corticosteroids (e.g. fluticasone propionate, fluticasone furoate, beclomethasone dipropionate, mometasone furoate, triamcinolone acetonide, budesonide and the steroid disclosed in WO02/12265), non-steroidal anti-inflammatory drugs (NSAIDs) (e.g. sodium cromoglycate, nedocromil sodium), PDE-4 inhibitors, leukotriene antagonists, lipoxygenase inhibitors, chemokine antagonists (e.g. CCR3, CCR1, CCR2, CCR4, CCR8, CXCR1, CXCR2), IKK antagonists, iNOS inhibitors, tryptase and elastase inhibitors, beta-2 integrin antagonists and adenosine 2a agonists; or beta adrenergic agents (e.g. salmeterol, salbutamol, formoterol, fenoterol, terbutaline, and the beta agonists described in WO 02/66422, WO 02/270490, WO02/076933, WO03/024439 and WO03/072539 and salts thereof); or anti-infective agents e.g. antibiotic agents and antiviral agents.

It will be clear to a person skilled in the art that, where appropriate, the other therapeutic agent(s) may be used in the form of salts, (e.g. as alkali metal or amine salts or as acid addition salts), or prodrugs, or as esters (e.g. lower alkyl esters), or as solvates (e.g. hydrates) to optimise the activity and/or stability and/or physical characteristics (e.g. solubility) of the therapeutic agent. It will be clear also that where appropriate, the therapeutic agents may be used in optically pure form.

There is provided, in another embodiment, a combination comprising a compound of formula (I) or a pharmaceutically acceptable salt thereof together with one or more (such as one or two, e.g. one) other therapeutically active agents, optionally with one or more pharmaceutically acceptable carriers and/or excipients.

In another embodiment, there is provided a combination comprising a compound which is 6-butyl-8-({1-[3-(ethylsulfonyl)propyl]-4-piperidinyl}oxy)quinoline, or a pharmaceutically acceptable salt thereof, together with one or more (such as one or two, e.g. one) other therapeutically active agents (such as those described herein), optionally with one or more pharmaceutically acceptable carriers and/or excipients.

In another embodiment, there is provided a combination comprising a compound which is N-(4-{4-[(6-butyl-8-quinolinyl)oxy]-1-piperidinyl}butyl)ethanesulfonamide, or a pharmaceutically acceptable salt (such as a dihydrochloride salt) thereof together with one or more (such as one or two, e.g. one) other therapeutically active agents (such as those described herein), optionally with one or more pharmaceutically acceptable carriers and/or excipients.

In another embodiment, there is provided a combination comprising a compound of formula (I) or a pharmaceutically acceptable salt thereof and an H3 and/or H4 antagonist.

Other histamine receptor antagonists which may be used alone, or in combination with an H1 receptor antagonist include antagonists (and/or inverse agonists) of the H4 receptor, for example, the compounds disclosed in Jablonowski et al., *J. Med. Chem.* 46:3957-3960 (2003), and antagonists (and/or inverse agonists) of the H3 receptor, for example the compounds described in WO2004/035556, the compounds described in WO2006/125665 and the compounds described in WO2006/090142.

In another embodiment, there is provided a combination comprising a compound of formula (I) or a pharmaceutically acceptable salt thereof and a $\beta_2$-adrenoreceptor agonist.

Examples of $\beta_2$-adrenoreceptor agonists include salmeterol (which may be a racemate or a single enantiomer, such as the R-enantiomer), salbutamol (which may be a racemate or a single enantiomer such as the R-enantiomer), formoterol (which may be a racemate or a single diastereomer such as the R,R-diastereomer), salmefamol, fenoterol, carmoterol, etanterol, naminterol, clenbuterol, pirbuterol, flerbuterol, reproterol, bambuterol, indacaterol, terbutaline and salts thereof, for example the xinafoate (1-hydroxy-2-naphthalenecarboxylate) salt of salmeterol, the sulfate salt or free base of salbutamol or the fumarate salt of formoterol. In one embodiment, combinations containing a compound of formula (I) may include longer-acting $\beta_2$-adrenoreceptor agonists, for example, compounds which provide effective bronchodilation for about 12 h or longer.

Other $\beta_2$-adrenoreceptor agonists include those described in WO 02/066422, WO 02/070490, WO 02/076933, WO 03/024439, WO 03/072539, WO 03/091204, WO 04/016578, WO 2004/022547, WO 2004/037807, WO 2004/037773, WO 2004/037768, WO 2004/039762, WO 2004/039766, WO01/42193 and WO03/042160.

Examples of $\beta_2$-adrenoreceptor agonists include:

3-(4-{[6-({(2R)-2-hydroxy-2-[4-hydroxy-3-(hydroxymethyl)phenyl]ethyl}amino)hexyl]oxy}butyl)benzenesulfonamide;

3-(3-{[7-({(2R)-2-hydroxy-2-[4-hydroxy-3-hydroxymethyl)phenyl]ethyl}-amino)heptyl]oxy}propyl)benzenesulfonamide;

4-{(1R)-2-[(6-{2-[(2,6-dichlorobenzyl)oxy]ethoxy}hexyl) amino]-1-hydroxyethyl}-2-(hydroxyl methyl)phenol;

4-{(1R)-2-[(6-{4-[3-(cyclopentylsulfonyl)phenyl] butoxy}hexyl)amino]-1-hydroxyethyl}-2-(hydroxylmethyl)phenol;

N-[2-hydroxyl-5-[(1R)-1-hydroxy-2-[[2-4-[[(2R)-2-hydroxy-2-phenylethyl]amino]phenyl]ethyl]amino]ethyl] phenyl]formamide;

N-2{2-[4-(3-phenyl-4-methoxyphenyl)aminophenyl]ethyl}-2-hydroxy-2-(8-hydroxy-2(1H)-quinolinon-5-yl)ethylamine; and 5-[(R)-2-(2-{4-[4-(2-amino-2-methyl-propoxy)-phenylamino]-phenyl}-ethylamino)-1-hydroxy-ethyl]-8-hydroxy-1H-quinolin-2-one.

The $\beta_2$-adrenoreceptor agonist may be in the form of a salt formed with a pharmaceutically acceptable acid selected from sulfuric, hydrochloric, fumaric, hydroxynaphthoic (for example 1- or 3-hydroxy-2-naphthoic), cinnamic, substituted cinnamic, triphenylacetic, sulfamic, sulfanilic, naphthaleneacrylic, benzoic, 4-methoxybenzoic, 2- or 4-hydroxybenzoic, 4-chlorobenzoic and 4-phenylbenzoic acid.

In another embodiment, there is provided a combination comprising a compound of formula (I) or a pharmaceutically acceptable salt thereof and an anti-inflammatory agent.

Anti-inflammatory agents include corticosteroids. Suitable corticosteroids which may be used in combination with the compounds of formula (I) are those oral and inhaled corticosteroids and their pro-drugs which have anti-inflammatory activity. Examples include methyl prednisolone, prednisolone, dexamethasone, fluticasone propionate, 6α,9α-difluoro-11β-hydroxy-16α-methyl-17α-[(4-methyl-1,3-thiazole-5-carbonyl)oxy]-3-oxo-androsta-1,4-diene-17β-carbothioic acid S-fluoromethyl ester, 6α,9α-difluoro-17α-[(2-furanylcarbonyl)oxy]-11β-hydroxy-16α-methyl-3-oxo-androsta-1,4-diene-17β-carbothioic acid S-fluoromethyl ester (fluticasone furoate), 6α,9α-difluoro-11β-hydroxy-16α-methyl-3-oxo-17α-propionyloxy-androsta-1,4-diene-17β-carbothioic acid S-(2-oxo-tetrahydro-furan-3S-yl)ester, 6α,9α-difluoro-11β-hydroxy-16α-methyl-3-oxo-17α(2,2,3,3-tetramethycyclo propylcarbonyl)oxy-androsta-1,4-diene-17β-carbothioic acid S-cyanomethyl ester and 6α,9α-difluoro-11β-hydroxy-16α-methyl-17α-(1-methycyclopropylcarbonyl)oxy-3-oxo-androsta-1,4-diene-17β-carbothioic acid S-fluoromethyl ester, beclomethasone esters (for example the 17-propionate ester or the 17,21-dipropionate ester), budesonide, flunisolide, mometasone esters (for example mometasone furoate), triamcinolone acetonide, rofleponide, ciclesonide (16α,17-[[(R)-cyclohexylmethylene]bis(oxy)]-11β,21-dihydroxy-pregna-1,4-diene-3,20-dione), butixocort propionate, RPR-106541, and ST-126. Corticosteroids of particular interest may include fluticasone propionate, 6α,9α-difluoro-11β-hydroxy-16α-methyl-17α-[(4-methyl-1,3-thiazole-5-carbonyl)oxy]-3-oxo-androsta-1,4-diene-17β-carbothioic acid S-fluoromethyl ester, 6α,9α-difluoro-17α-[(2-furanylcarbonyl)oxy]-11β-hydroxy-16α-methyl-3-oxo-androsta-1,4-diene-17β-carbothioic acid S-fluoromethyl ester, 6α,9α-difluoro-11β-hydroxy-16α-methyl-3-oxo-17α-(2,2,3,3-tetramethycyclopropylcarbonyl)oxy-androsta-1,4-diene-17β-carbothioic acid S-cyano methylester, 6α,9α-difluoro-11β-hydroxy-16α-methyl-17α-(1-methycyclopropylcarbonyl) oxy-3-oxo-androsta-1,4-diene-17β-carbothioic acid S-fluoromethyl ester and mometasone furoate. In one embodiment the corticosteroid is 6α,9α-difluoro-17α-[(2-furanylcarbonyl)oxy]-11β-hydroxy-16α-methyl-3-oxo-androsta-1,4-diene-17β-carbothioic acid S-fluoromethyl ester (fluticasone furoate) or mometasone furoate.

There is provided, in a further embodiment, a combination comprising a compound of formula (I) or a pharmaceutically acceptable salt thereof, together with a corticosteroid, such as fluticasone propionate or 6α,9α-difluoro-17α-[(2-furanylcarbonyl)oxy]-11β-hydroxy-16α-methyl-3-oxo-androsta-1, 4-diene-17β-carbothioic acid S-fluoromethyl ester (fluticasone furoate) or mometasone furoate. Such combinations may be of particular interest for intranasal administration.

In another embodiment, there is provided a combination comprising a compound which is N-(4-{4-[(6-butyl-8-quinolinyl)oxy]-1-piperidinyl}butyl)ethanesulfonamide, or a pharmaceutically acceptable salt (such as a dihydrochloride salt) thereof together with 6α,9α-difluoro-17α-[(2-furanylcarbonyl)oxy]-11β-hydroxy-16α-methyl-3-oxo-androsta-1,4-diene-17β-carbothioic acid S-fluoromethyl ester (fluticasone furoate). In another embodiment, the combination is suitable for intranasal administration.

In another embodiment, there is provided a combination comprising a compound of formula (I) or a pharmaceutically acceptable salt thereof and a glucocorticoid agonist.

Non-steroidal compounds having glucocorticoid agonism that may possess selectivity for transrepression over transactivation and that may be useful in combination therapy include those covered in the following patent application and patents: WO03/082827, WO98/54159, WO04/005229, WO04/009017, WO04/018429, WO03/104195, WO03/082787, WO03/082280, WO03/059899, WO03/101932, WO02/02565, WO01/16128, WO0/66590, WO03/086294, WO04/026248, WO03/061651, WO03/08277, WO06/000401, WO06/000398 and WO06/015870.

Anti-inflammatory agents include non-steroidal anti-inflammatory drugs (NSAID's).

NSAID's include sodium cromoglycate, nedocromil sodium, phosphodiesterase (PDE) inhibitors (e.g. theophylline, PDE4 inhibitors or mixed PDE3/PDE4 inhibitors), leukotriene antagonists, inhibitors of leukotriene synthesis (eg. montelukast), iNOS (inducible nitric oxide synthase) inhibitors (e.g. oral iNOS inhibitors), IKK antagonists, tryptase and elastase inhibitors, beta-2 integrin antagonists and adenosine receptor agonists or antagonists (e.g. adenosine 2a agonists), cytokine antagonists (e.g. chemokine antagonists, such as a CCR1, CCR2, CCR3, CCR4, or CCR8 antagonists) or inhibitors of cytokine synthesis, or 5-lipoxygenase inhibitors. iNOS inhibitors include those disclosed in WO93/13055, WO98/30537, WO02/50021, WO95/34534 and WO99/62875.

In another embodiment there is provided the use of the compounds of formula (I) or a pharmaceutically acceptable salt thereof in combination with a phosphodiesterase 4 (PDE4) inhibitor. The PDE4-specific inhibitor useful in this embodiment may be any compound that is known to inhibit the PDE4 enzyme or which is discovered to act as a PDE4 inhibitor, and which are selective PDE4 inhibitors, not compounds which inhibit other members of the PDE family, such as PDE3 and PDE5, as well as PDE4.

Compounds which may be of interest include cis-4-cyano-4-(3-cyclopentyloxy-4-methoxyphenyl)cyclohexan-1-carboxylic acid, 2-carbomethoxy-4-cyano-4-(3-cyclopropylmethoxy-4-difluoromethoxyphenyl)cyclohexan-1-one and cis-[4-cyano-4-(3-cyclopropylmethoxy-4-difluoromethoxyphenyl)cyclohexan-1-ol]. Also, cis-4-cyano-4-[3-(cyclopentyloxy)-4-methoxyphenyl]cyclohexane-1-carboxylic acid (also known as cilomilast) and its salts, esters, pro-drugs or physical forms, which is described in U.S. Pat. No. 5,552,438 issued 3 Sep. 1996.

Other PDE4 inhibitors include AWD-12-281 from Elbion (Hofgen, N. et al., 15th EFMC Int. Symp. Med. Chem., (Sep. 6-10, Edinburgh) 1998, Abst. P. 98; CAS reference No. 247584020-9); a 9-benzyladenine derivative nominated NCS-613 (INSERM); D-4418 from Chiroscience and Schering-Plough; a benzodiazepine PDE4 inhibitor identified as CI-1018 (PD-168787) and attributed to Pfizer; a benzodioxole derivative disclosed by Kyowa Hakko in WO99/16766; K-34 from Kyowa Hakko; V-11294A from Napp (Landells, L. J. et al., Eur. Resp. J. [Ann. Cong. Eur. Resp. Soc. (Sep. 19-23, Geneva) 1998] 1998, 12 (Suppl. 28): Abst P2393); roflumilast (CAS reference No 162401-32-3) and a pthalazinone (WO99/47505) from Byk-Gulden; Pumafentrine, (−)-p-[(4aR*,10bS*)-9-ethoxy-1,2,3,4,4a,10b-hexahydro-8-methoxy-2-methylbenzo[c][1,6]naphthyridin-6-yl]-N,N-diisopropylbenzamide which is a mixed PDE3/PDE4 inhibitor which has been prepared and published on by Byk-Gulden, now Altana; arofylline under development by Almirall-Prodesfarma; VM554/UM565 from Vernalis; or T-440 (Tanabe Seiyaku; Fuji, K. et al., J. Pharmacol. Exp. Ther., 284(1):162, (1998)), and T2585.

Further PDE4 inhibitors which may be of interest are disclosed in the published international patent applications WO04/024728 (Glaxo Group Ltd), WO04/056823 (Glaxo Group Ltd) and WO04/103998 (Glaxo Group Ltd). A particular compound of interest is 6-({3-[(di methylamino)carbonyl]phenyl}sulfonyl)-8-methyl-4-{[3-(methyloxy)phenyl]amino}-3-quinolinecarboxamide or a pharmaceutically acceptable salt thereof, which is described in International Patent Application WO04/103998.

In another embodiment, there is provided a combination comprising a compound which is N-(4-{4-[(6-butyl-8-quinolinyl)oxy]-1-piperidinyl}butyl)ethanesulfonamide, or a pharmaceutically acceptable salt (such as a dihydrochloride salt) thereof together with 6-({3-[(dimethylamino)carbonyl]phenyl}sulfonyl)-8-methyl-4-{[3-(methyloxy)phenyl]amino}-3-quinolinecarboxamide or a pharmaceutically acceptable salt thereof.

In another embodiment, there is provided a combination comprising a compound of formula (I) or a pharmaceutically acceptable salt thereof and an anticholinergic agent.

Anticholinergic agents are those compounds that act as antagonists at the muscarinic receptors, in particular those compounds which are antagonists of the $M_1$ or $M_3$ receptors, dual antagonists of the $M_1/M_3$ or $M_2/M_3$, receptors or pan-antagonists of the $M_1/M_2/M_3$ receptors. Exemplary compounds for administration via inhalation include ipratropium (for example, as the bromide, CAS 22254-24-6, sold under the name Atrovent), oxitropium (for example, as the bromide, CAS 30286-75-0) and tiotropium (for example, as the bromide, CAS 136310-93-5, sold under the name Spiriva). Also of interest are revatropate (for example, as the hydrobromide, CAS 262586-79-8) and LAS-34273 which is disclosed in WO01/04118. Exemplary compounds for oral administration include pirenzepine (for example, CAS 28797-61-7), darifenacin (for example, CAS 133099-04-4, or CAS 133099-07-7 for the hydrobromide sold under the name Enablex), oxybutynin (for example, CAS 5633-20-5, sold under the name Ditropan), terodiline (for example, CAS 15793-40-5), tolterodine (for example, CAS 124937-51-5, or CAS 124937-52-6 for the tartrate, sold under the name Detrol), otilonium (for example, as the bromide, CAS 26095-59-0, sold under the name Spasmomen), trospium chloride (for example, CAS 10405-02-4) and solifenacin (for example, CAS 242478-37-1, or CAS 242478-38-2, or the succinate also known as YM-905 and sold under the name Vesicare).

Other anticholinergic agents include compounds which are disclosed in U.S. patent application 60/487,981, published as WO2005/009439 and those compounds disclosed in U.S. patent application 60/511,009, published as WO2005/037280.

The combinations referred to above may conveniently be presented for use in the form of a pharmaceutical composition and thus the present invention further provides pharmaceutical compositions comprising a combination as defined above optionally together with a pharmaceutically acceptable carrier and/or excipient.

The individual compounds of such combinations may be administered either sequentially in separate pharmaceutical compositions or simultaneously in combined pharmaceutical compositions. Appropriate doses of known therapeutic agents will be readily appreciated by those skilled in the art.

Compounds of formula (I) may be prepared by the methods described below or by similar methods. Thus the following Intermediates and Examples illustrate the preparation of the compounds of formula (I), and are not to be considered as limiting the scope of the disclosure in any way.

BRIEF DESCRIPTION OF THE FIGURES

FIG. 1 is an XPRD pattern of N-(4-{4-[(6-Butyl-8-quinolinyl)oxy]-1-piperidinyl}butyl)ethanesulfonamide, dihydrochloride salt (Example 23B) with linear scale on intensity axis (y-axis).

FIG. 2 is an XPRD pattern of N-(4-{4-[(6-Butyl-8-quinolinyl)oxy]-1-piperidinyl}butyl)ethanesulfonamide, dihydrochloride salt (Example 23B) with square-root scale on intensity axis (y-axis).

FIG. 3 is a graphical depiction showing duration of action of N-(4-{4-[(6-butyl-8-quinolinyl)oxy]-1-piperidinyl}butyl)ethanesulfonamide, dihydrochloride salt (Example 23B) and azelastine in a conscious guinea-pig model of histamine-induced nasal congestion.

General Experimental

Abbreviations

DCM: Dichloromethane

DMF: N,N'-Dimethyl formamide

EtOAc: Ethyl acetate g: Grams h: Hours

HPLC: High performance liquid chromatography

HRMS: High-resolution mass-spectroscopy

LCMS: Liquid-chromatography mass-spectroscopy

MDAP: Mass-directed auto-preparative HPLC min Minutes mg: Milligrams ml: Millilitres NMP: N-methylpyrrolidinone s.g.: specific gravity (gml$^{-1}$)

THF: Tetrahydrofuran

General Experimental Procedures

Flash silica gel refers to Merck Art No. 9385; silica gel refers to Merck Art No. 7734.

SCX cartridges are Ion Exchange SPE columns where the stationary phase is polymeric benzene sulfonic acid. These are used to isolate amines.

SCX2 cartridges are Ion Exchange SPE columns where the stationary phase is polymeric propylsulfonic acid. These are used to isolate amines.

LCMS was conducted on a Supelcosil LCABZ+PLUS column (3.3 cm×4.6 mm ID) eluting with 0.1% formic acid and 0.01 M ammonium acetate in water (solvent A) and 0.05% formic acid 5% water in MeCN (solvent B), using the following elution gradient 0.0-7 min 0% B, 0.7-4.2 min 100% B, 4.2-5.3 min 0% B, 5.3-5.5 min 0% B at a flow rate of 3 mlmin$^{-1}$. The mass spectra were recorded on a Fisons VG Platform spectrometer using electrospray positive and negative mode (ES+ve and ES−ve).

The Flashmaster II is an automated multi-user flash chromatography system, available from Argonaut Technologies Ltd, which utilises disposable, normal phase, SPE cartridges (2 g to 100 g). It provides quaternary on-line solvent mixing to enable gradient methods to be run. Samples are queued using the multi-functional open access software, which manages solvents, flow-rates, gradient profile and collection conditions. The system is equipped with a Knauer variable wavelength UV-detector and two Gilson FC204 fraction-collectors enabling automated peak cutting, collection and tracking.

Mass directed autopreparative (MDAP) HPLC was conducted on a Waters FractionLynx system comprising of a Waters 600 pump with extended pump heads, Waters 2700 autosampler, Waters 996 diode array and Gilson 202 fraction collector on a 10 cm×2.54 cm internal diameter ABZ+ column, eluting with 0.1% formic acid in water (solvent A) and 0.1% formic acid in MeCN (solvent B), using an appropriate elution gradient over 15 min at a flow rate of 20 mlmin$^{-1}$ and detecting at 200-320 nm at room temperature. Mass spectra were recorded on Micromass ZMD mass spectrometer using electro spray positive and negative mode, alternate scans. The software used was MassLynx 3.5 with OpenLynx and FractionLynx options.

The $^1$H NMR spectra were recorded on a Bruker AV400 operating at 400 MHz. Standard deuterated solvents were used. Tetramethylsilane may have been used as internal standard.

Reactions are routinely monitored by methods well known to those skilled in the art, such as TLC, LCMS and/or HPLC. Such methods are used to assess whether a reaction has gone to completion, and reaction times may be varied accordingly.

The XRPD method which was employed to analyse crystalline forms of compounds was as follows:

| Manufacturer | PANalytical - The Netherlands |
|---|---|
| Instrument | X'Pert Pro |
| Diffractometer Type | DY1850 |
| Tube anode | Cu |
| K-Alpha1 wavelength (A °) | 1.54056 |
| K-Alpha2 wavelength (A °) | 1.54439 |
| Ration Alpha 1:2 | 0.50000 |
| Divergence slit | Prog.Div.Slit |
| Receiving slit | Prog.Rec.Slit |
| Generator voltage (kV) | 40 |
| Tube Current (mA) | 45 |
| Detector | X'celerator |
| Data Angle range (°2θ) | 2.000-39.997 |
| Scan type | Continuous |
| Scan step size | 0.0167 |
| Scan step time (seconds) | 31.75 |
| Sample preparation | Backfilled |

XRPD analysis was performed on a PANalytical X'Pert Pro X-ray powder diffractometer, model X'Pert Pro PW3040/60, serial number DY1850 using an X'Celerator detector. The acquisition conditions were: radiation: Cu K, generator tension: 40 kV, generator current: 45 mA, start angle: 2.000° 2θ, end angle: 39.997° 2θ, step size: 0.0167, time per step: 31.75 seconds. The sample was prepared by backfilling. The margin of error is approximately ±0.1° 2θ for each of the peak assignments.

Compounds were named using ACD/Name PRO 6.02 chemical naming software from Advanced Chemistry Developments Inc.; Toronto, Ontario, M5H2L3, Canada.

Intermediates

Intermediate 1

6-Bromo-8-fluoroquinoline

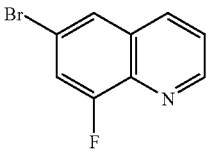

A solution of concentrated sulphuric acid (63 ml, 820 mmol) in water (49.4 ml) was treated with sodium 3-nitrobenzenesulfonate (commercially available, for example, from Aldrich) (47.9 g, 213 mmol) and glycerol (commercially available, for example, from Fluka and/or Aldrich) (52 ml, 720 mmol) to give a thick grey suspension. This was heated to 110° C. (internal temperature was 85° C.). 4-Bromo-2-fluoroaniline (commercially available, for example, from Fluorochem and/or Aldrich) (38 g, 200 mmol) was added over 10 min in portions, during which the internal temperature rose to 95° C. The reaction was heated to 140° C. (internal temperature was 133° C.) and stirred overnight. The reaction mixture was cooled and then poured into water (1000 ml) and basified to pH 7 with aqueous ammonia (0.88 s.g, approximately 190 ml). The brown precipitate that formed was collected by filtration and partially dried. This solid (63 g) was loaded onto a column of silica (1500 ml) and eluted with EtOAc to give the title compound as a light brown solid (43.8 g, 97%). LCMS RT=2.87 min, ES+ve m/z 226/228 [M+H]⁺.

Intermediate 2

6-Butyl-8-fluoroquinoline

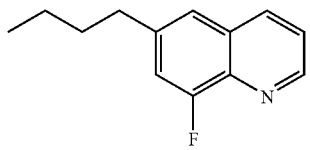

A mixture of 6-bromo-8-fluoroquinoline (for example, as prepared for Intermediate 1) (24 g, 106 mmol) in DMF (150 ml) was treated under nitrogen with potassium carbonate (33 g, 240 mmol), tributylborane solution in THF (commercially available, for example, from Aldrich) (1M, 200 ml) and [1,1'-bis(diphenylphosphino) ferrocene palladium (II)]chloride (1 g, 1.2 mmol). The resulting mixture was stirred under nitrogen and heated at 75° C. overnight. The mixture was allowed to cool, diluted with water and extracted with EtOAc (×3). The combined organic layers were filtered through a frit to remove any insoluble material and the filtrate washed with water. The organic layer was dried (MgSO₄), and the filtrate evaporated to dryness. The residue was purified twice by flash chromatography eluting with DCM-EtOAc (1:0 to 2:1) to afford the title compound (14.47 g, 67%). LCMS RT=3.38 min, ES+ve m/z 204 [M+H]⁺.

Intermediate 3

1,1-Dimethylethyl 4-[(6-butyl-8-quinolinyl)oxy]-1-piperidinecarboxylate

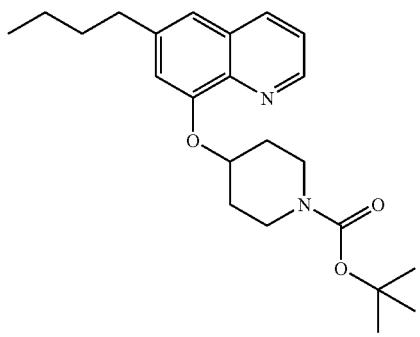

A solution of 6-butyl-8-fluoroquinoline (for example, as prepared for Intermediate 2) (14.4 g, 70.9 mmol) in NMP (20 ml) was added to a mixture of tert-butyl-4-hydroxy-1-piperidinecarboxylate (commercially available, for example, from Aldrich) (21.6 g, 108 mmol) and sodium tert-butoxide (10.4 g, 108 mmol) in NMP (75 ml), and the resulting mixture was stirred at 140° C. for approximately 90 min and then allowed to cool overnight. The reaction mixture was treated with ammonium chloride solution and extracted with EtOAc (×2). The combined organic extracts were washed with water, dried (MgSO₄), filtered and evaporated to dryness. The residue was purified by flash chromatography eluting with DCM-EtOAc (1:0 to 1:1) and then twice by Flashmaster chromatography eluting with DCM-EtOAc (1:0 to 3:1) over 40 min to give the title compound (22 g). LCMS RT=3.49 min, ES+ve m/z 385 [M+H]⁺

Intermediate 4

6-Butyl-8-(4-piperidinyloxy)quinoline

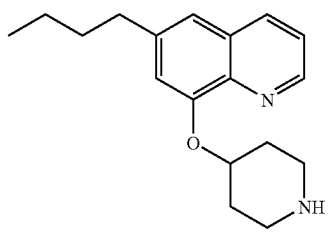

1,1-Dimethylethyl 4-[(6-butyl-8-quinolinyl)oxy]-1-piperidinecarboxylate (for example, as prepared for Intermediate 3) (21.5 g, 56 mmol) was dissolved in DCM (50 ml) and trifluoroacetic acid (50 ml) was added very slowly. The mixture was stirred at room temperature for 1 h. The solvent was evaporated to dryness and the residue treated with saturated aqueous sodium carbonate solution. The mixture was extracted with EtOAc (×2), washed with water, and dried (MgSO₄). The drying agent was removed by filtration and the filtrate was evaporated to dryness (22 g). This was still a trifluoracetic acid salt and was re-dissolved in EtOAc, washed with aqueous sodium carbonate, water, and dried (MgSO₄). The drying agent was removed by filtration and the filtrate was evaporated to dryness to afford the title compound (15.9 g). LCMS RT=2.45 min, ES+ve m/z 285 [M+H]⁺.

Intermediate 5

6-Chloro-8-fluoroquinoline

A solution of concentrated sulphuric acid (16 ml, 300 mmol) in water (12 ml) was treated with sodium 3-nitrobenzenesulfonate (commercially available, for example, from Aldrich) (11.3 g, 50 mmol) and glycerol (commercially available, for example, from Fisher and/or Aldrich) (12 ml, 160 mmol) to give a suspension. This was heated to 110° C. with stirring, and 4-chloro-2-fluoroaniline (commercially available, for example, from Aldrich) (5.6 ml, 50 mmol) was added. The reaction was heated to 140° C. and stirred overnight. The reaction mixture was cooled and then poured into water (400 ml) and basified to pH 11 with aqueous ammonium hydroxide (0.88 s.g., 60 ml). The brown precipitate that formed was collected by filtration and dried under suction. EtOAc was then added to the sinter funnel, dissolving most of the material to give a brown solution. This filtrate was concentrated in vacuo to give a brown solid (7.7 g). This was purified by chromatography on silica (2×100 g, eluting with 0-50% EtOAc-cyclohexane over 60 min). The relevant fractions were concentrated in vacuo to give the title compound as a yellow solid (6.5 g, 70%) LCMS RT=2.78 min, ES+ve m/z 182/184 [M+H]⁺.

Intermediate 6

1,1-Dimethylethyl 4-[(6-chloro-8-quinolinyl)oxy]-1-piperidinecarboxylate

6-Chloro-8-fluoroquinoline (for example, as prepared for Intermediate 5) (2.18 g, 12 mmol) was dissolved in NMP (20 ml) and treated with 1,1-dimethylethyl 4-hydroxy-1-piperidinecarboxylate (commercially available, for example, from Acros and/or Aldrich) (4.85 g, 24 mmol) and sodium tert-butoxide (2.38 g, 25 mmol). Further NMP was added (5 ml) and the resulting mixture was stirred at 140° C. for 1 h, and then allowed to cool overnight. The reaction mixture was treated with water and extracted with toluene. The organic extract was washed with water (×3), dried ($MgSO_4$), and concentrated in vacuo. The residue was purified by silica chromatography (2×70 g), eluting with 0-100% EtOAc-cyclohexane over 30 min. The relevant fractions were concentrated in vacuo to give the title compound as a yellow gum (2.73 g, 63%): LCMS RT=3.37 min, ES+ve m/z 363/365 $[M+H]^+$.

Intermediate 7

1,1-Dimethylethyl 4-[(6-pentyl-8-quinolinyl)oxy]-1-piperidinecarboxylate 1,1-Dimethylethyl 4-[(6-chloro-8-quinolinyl)oxy]-1-piperidinecarboxylate (for example, as prepared for Intermediate 6) (2.73 g, 7.5 mmol) was dissolved in a mixture of THF (55 ml), NMP (5.6 ml) and iron (III) acetylacetonate (220 mg, 0.62 mmol) were added, and the mixture was cooled to 0° C. and stirred under a nitrogen atmosphere. n-Pentyl magnesium bromide (commercially available, for example, from TCI-Europe and/or Aldrich) was added dropwise over 9 min. The stirring was continued at 0° C. for 1 h, and the reaction was then allowed to warm to room temperature with stirring overnight. The reaction mixture was treated with aqueous ammonium chloride solution and extracted with EtOAc (×3). The combined organic extracts were filtered, dried ($MgSO_4$), and concentrated in vacuo. The residue was purified by silica chromatography (2×100 g), eluting with 0-50% EtOAc-cyclohexane over 40 min. The relevant fractions were concentrated in vacuo to give the title compound as a yellow oil (2.2 g, 74%): LCMS RT=3.76 min, ES+ve m/z 399 $[M+H]^+$.

Intermediate 8

6-Pentyl-8-(4-piperidinyloxy)quinoline 1,1-Dimethylethyl 4-[(6-pentyl-8-quinolinyl)oxy]-1-piperidinecarboxylate (for example, as prepared for Intermediate 7) (2.20 g, 5.52 mmol) was dissolved in dioxane (10 ml) and the solution was treated with a solution of hydrogen chloride in dioxane (4M, 12.5 ml). The mixture was stirred under nitrogen overnight at room temperature, and then concentrated in vacuo. The residue was applied to a SCX-2 ion exchange cartridge (70 g) which had been preconditioned with methanol. The cartridge was washed with methanol, and then eluted with 10% aqueous 0.88 s.g. ammonia in methanol. The relevant basic fractions were concentrated in vacuo to give the title compound (1.88 g); LCMS RT=2.70 min, ES+ve m/z 299 $[M+H]^+$.

Intermediate 9

1,1-Dimethylethyl(3R)-3-[(6-butyl-8-quinolinyl)oxy]-1-pyrrolidinecarboxylate This was prepared in an analogous manner to Intermediate 3, using 6-butyl-8-fluoroquinoline (for example, as prepared for Intermediate 2) and N-tert-butoxycarbonyl-(R)-(−)-3-pyrrolidinol (commercially available, for example, from Aldrich) instead of 1,1-dimethylethyl 4-hydroxy-1-piperidinecarboxylate. The reaction time was 3 h instead of 1.5 h. LCMS RT=3.56 min, ES+ve m/z 371 $(M+H)^+$.

Intermediate 10

6-Butyl-8-[(3R)-3-pyrrolidinyloxy]quinoline

This was prepared in an analogous manner to Intermediate 4, using 1,1-dimethylethyl (3R)-3-[(6-butyl-8-quinolinyl)oxy]-1-pyrrolidinecarboxylate (for example, as prepared for Intermediate 9) and 4 M hydrogen chloride in 1,4-dioxane instead of trifluoroacetic acid for 45 min. LCMS RT=2.46 min, ES+ve m/z 271 $(M+H)^+$.

Intermediate 11

2-[(1,1-Dimethylethyl)thio]ethanol

A mixture of bromoethanol (commercially available, for example, from Avocado) (1.5 ml, 21 mmol) and sodium 2-methyl-2-propanethiolate (commercially available, for example, from Aldrich) (2.5 g, 22 mmol) in DMF (10 ml) were heated to 70° C. overnight. The mixture was cooled to room temperature, diluted with water and extracted with EtOAc (×2). The organic solution was washed with water, brine, dried ($MgSO_4$), and evaporated under reduced pressure to give a mixture containing starting material and product by NMR (578 mg). This was re-dissolved in DMF (5 ml) and treated with sodium 2-methyl-2-propanethiolate (2.5 g, 22 mmol) and heated to 80° C. for 4 days. The mixture was cooled to room temperature, diluted with water and extracted with EtOAc (×2). The organic solution was washed with water (×5), brine, dried ($MgSO_4$), and evaporated under reduced pressure to give the title compound (332 mg, 9%): $^1$H NMR δ ($CDCl_3$) 3.73 (2H, t, J=6 Hz), 2.77 (2H, t, J=6 Hz), 2.19-2.07 (1H, br), 1.31 (9H, s).

Intermediate 12

2-Chloroethyl 1,1-dimethylethyl sulfide

A solution of 2-[(1,1-dimethylethyl)thio]ethanol (for example, as prepared for Intermediate 11) in DCM (5 ml) was treated with triethylamine (1 ml, 7 mmol), followed by methanesulfonyl chloride (commercially available, for example, from Aldrich) (0.38 ml, 5 mmol) at room temperature. After 1 h the mixture was diluted with DCM and washed with water (×3), 2 M hydrochloric acid, water, dried ($MgSO_4$), and evaporated under reduced pressure to give the title compound (354 mg, 94%): $^1$H NMR δ (CDCl$_3$) 3.61 (2H, dd, J=8, 7 Hz), 2.88 (2H, dd, J=8, 7 Hz), 1.31 (9H, s).

Intermediate 13

2-Chloroethyl 1,1-dimethylethyl sulfone

A solution of 2-chloroethyl 1,1-dimethylethyl sulfide (for example, as prepared for Intermediate 12) (354 mg, 2.31 mmol) in DCM (10 ml) was treated with m-chloroperbenzoic acid (commercially available, for example, from Aldrich) (1.5 g, 57-86% pure, at least 5 mmol) and the mixture was stirred at room temperature for 2 h. The mixture was diluted with DCM and washed with water, sodium metabisulfite solution, sodium bicarbonate solution, dried (MgSO$_4$), and evaporated under reduced pressure to give the title compound (208 mg, 49%): $^1$H NMR δ (CDCl$_3$) 3.95 (2H, dd, J=8, 7 Hz), 3.38 (2H, dd, J=8, 7 Hz), 1.42 (9H, s).

Intermediate 14

3-Chloropropyl ethyl sulfone

Sodium ethanethiolate (commercially available, for example, from Aldrich) (2.0 g, 24 mmol) in ethanol (24 ml) was treated with 1-bromo-3-chloropropane (commercially available, for example, from Aldrich) (2.35 ml, 24 mmol) and the mixture was stirred at room temperature for 3 days. The mixture was then diluted with diethyl ether and filtered to remove the white precipitate. The filtrate was then concentrated by distillation of the solvents at atmospheric pressure. The solid residue from the filtration was combined with the solid residue from the distillation, and partitioned between water and DCM. The aqueous phase was extracted with DCM and the combined organic solutions were dried (MgSO$_4$), filtered, and the filtrate was treated with m-chloroperbenzoic acid (commercially available, for example, from Aldrich) (1 g, 57-86% pure, at least 3 mmol) and the mixture was stirred at room temperature overnight. The reaction mixture was diluted with DCM and washed with sodium bicarbonate solution. The organic solution was washed with aqueous sodium metabisulfite solution (×2), aqueous sodium bicarbonate solution, dried (MgSO$_4$) and evaporated under reduced pressure. The residue (790 mg) was dissolved in DCM and applied to a silica cartridge (20 g) eluting with a gradient of diethylether-petroleum ether (40-60° C.) (20%-60%) to give the title compound (260 mg, 6%): $^1$H NMR δ (CDCl$_3$) 3.71 (2H, t, J=7 Hz), 3.15 (2H, t, J=7 Hz), 3.04 (2H, q, J=7 Hz), 2.40-2.30 (2H, m), 1.44 (3H, t, J=7 Hz).

Intermediate 15

3-(Ethylthio)propyl 4-methyl benzenesulfonate

Preparation A

A solution of 3-(ethylthio)propanol (commercially available, for example, from Alfa Aesar) (1.2 g, 10 mmol) in pyridine (10 ml) was treated portionwise with p-toluenesulfonyl chloride (commercially available, for example from Aldrich) (1.9 g, 10 mmol) at room temperature and the solution was stirred for 20 h. The reaction mixture was diluted with EtOAc, washed with water, 2 M hydrochloric acid, sodium bicarbonate solution (×2), brine, dried (MgSO$_4$), and evaporated under reduced pressure. The residue (1.2 g) was purified by Flashmaster 2 chromatography on a silica cartridge (70 g) eluting with 0 to 25% EtOAc-cyclohexane over 40 min. The appropriate fractions were combined and evaporated to give the title compound (667 mg, 24%): LCMS RT=3.37 min, ES+ve m/z 275 (M+H)$^+$.

Preparation B

Sodium ethanethiolate (commercially available, for example from Aldrich) (840 mg, 10 mmol) was added portionwise over 10 min to a solution of 1,3-propanediol ditosylate (commercially available, for example, from Aldrich) (3.84 g, 10 mmol) in DMF (25 ml) at room temperature under nitrogen and the mixture was stirred for 3 days and then heated to 75° C. for 4 h. The solvent was removed under reduced pressure and the residue was partitioned between EtOAc and aqueous sodium bicarbonate. The organic solution was washed with aqueous sodium bicarbonate, dried (MgSO$_4$) and evaporated under reduced pressure. The residue (1.9 g) was dissolved in DCM and purified by Flashmaster 2 chromatography on a silica cartridge (70 g) eluting with 0-25% EtOAc-cyclohexane over 40 min to give the title compound (250 mg, 9%): $^1$H NMR δ (CDCl$_3$) 7.80 (2H, d, J=8 Hz), 7.36 (2H, d, J=8 Hz), 4.15 (2H, t, J=6 Hz), 2.54 (2H, t, J=7 Hz), 2.48 (2H, q, J=7 Hz), 2.46 (3H, s), 1.97-1.88 (2H, m), 1.21 (3H, t, J=7 Hz).

Intermediate 16

3-(Ethylsulfonyl)propyl 4-methylbenzenesulfonate

A solution of 3-(ethylthio)propyl 4-methylbenzenesulfonate (for example, as prepared for Intermediate 15) (2.43 mmol) in DCM (40 ml) was treated with m-chloroperbenzoic acid (commercially available, for example, from Aldrich) (1.9 g, 57-86% pure, at least 6.6 mmol) and the mixture was stirred at room temperature for 2.5 h. The reaction mixture was diluted with DCM and washed with aqueous solution of sodium bicarbonate, sodium metabisulfite, water, dried (MgSO$_4$), and concentrated under reduced pressure to give the title compound, which solidified on standing (735 mg, 99%): $^1$H NMR δ (CDCl$_3$) 7.80 (2H, d, J=8 Hz), 7.37 (2H, d, J=8 Hz), 4.18 (2H, t, J=6 Hz), 3.04 (2H, t, J=7 Hz), 3.00 (2H, q, J=7 Hz), 2.47 (3H, s), 2.26-2.19 (2H, m), 1.40 (3H, t, J=7 Hz).

Intermediate 17

3-Bromopropyl 1,1-dimethylethyl sulfone and 3-chloropropyl 1,1-dimethylethyl sulfone A solution of 1-bromo-3-chloropropane (commercially available, for example, from Aldrich) (4.0 ml, 40 mmol) in DMF (5 ml) was treated with sodium 2-methyl-2-propanethiolate (commercially available, for example, from Aldrich) (3.36 g, 30 mmol) and the mixture was stirred for 24 h at room temperature and another 24 h at 70° C. The mixture was allowed to cool to room temperature, and partitioned between water and diethyl ether. The aqueous layer was again extracted with diethyl ether and the combined organic solutions were washed with water (×4), brine (×2), dried (MgSO$_4$) and evaporated under reduced pressure to give an oil (4.3 g) which solidified on standing at room temperature. This was dissolved in DCM (80 ml) and treated with m-chloroperbenzoic acid (commercially available, for example, from Aldrich) (13.8 g, 57-86% pure, at least 48 mmol) and the mixture was stirred overnight at room temperature. The mixture was diluted with DCM and washed with aqueous sodium bicarbonate solution (×2), 1 M sodium hydroxide (100 ml), dried (MgSO$_4$), and evaporated. The residue (4.85 g) was split into two portions; one portion (1.8 g) was purified by Flashmaster 2 chromatography on a silica cartridge (100 g) eluting with 0-50% EtOAc-cyclohexane over 40 min. The remainder was purified by flash chromatography on silica (150 g) eluting with 0-50% EtOAc-cyclohexane. Appropriate fractions were combined and evaporated to give a mixture of the title compounds (1.1 g) in a 1:1 ratio: $^1$H NMR δ (CDCl$_3$) 3.75 (2H, t, J=6 Hz), 3.11 (2H, t, J=7 Hz), 2.43-2.36 (2H, m), 1.45 (9H, s) for the chloride and 3.61 (2H, t, J=6 Hz), 3.11 (2H, t, J=7 Hz), 2.51-2.44 (2H, m), 1.45 (9H, s) for the bromide.

Intermediates 18 to 20 were prepared in an analogous manner to that disclosed for Intermediate 17:

Intermediate 18

3-Bromopropyl propyl sulfone and 3-chloropropyl propyl sulfone

Obtained as a mixture of the title compounds using sodium 1-propanethiolate (commercially available, for example, from Aldrich) instead of sodium 2-methyl-2-propanethiolate (ratio: 4:3 bromide:chloride): $^1$H NMR δ (CDCl$_3$) includes 3.70 (2H, t, J=6 Hz, minor), 3.55 (2H, t, J=6 Hz, major), 3.20-3.10 (4H, m), 1.93-1.82 (2H, m), 1.09 (3H, t, J=7 Hz).

Intermediate 19

3-Bromopropyl methyl sulfone and 3-chloropropyl methyl sulfone

Obtained as a mixture of the title compounds using sodium methanethiolate (commercially available, for example, from Aldrich) instead of sodium 2-methyl-2-propanethiolate (ratio: 64:36, bromide:chloride): LCMS RT=0.86 min, ES+ve m/z 174/176 (3:1, M+NH$_4$)$^+$ and RT=1.00 min, ES+ve m/z 218/220 [(1:1), (M+NH$_4$)$^+$].

Intermediate 20

3-Bromopropyl 1-methylethyl sulfone and 3-chloropropyl 1-methylethyl sulfone

Obtained as a mixture of the title compounds using sodium 2-propanethiolate (commercially available, for example, from Aldrich) instead of sodium 2-methyl-2-propanethiolate (ratio: 43:57, chloride:bromide) $^1$H NMR δ (CDCl$_3$) 3.71 (2H, t, J=6 Hz, minor), 3.56 (2H, t, J=6 Hz, major), 3.16-3.09 (3H, m), 2.45-2.30 (2H, m), 1.41 (6H, d, J=7 Hz).

Intermediate 21

4-Bromobutyl 1,1-dimethylethyl sulfide

A solution of 1,4-dibromobutane (commercially available, for example, from Aldrich) (4.7 ml, 40 mmol) in DMF (10 ml) was treated with sodium 2-methyl-2-propanethiolate (commercially available, for example, from Aldrich) (3.36 g, 30 mmol) and the mixture was heated for 23 h at 70° C. The mixture was allowed to cool to room temperature, and partitioned between water and EtOAc. The organic solution was washed with water (×4), aqueous sodium bicarbonate solution, brine, dried (MgSO$_4$), and evaporated. The residue was purified by flash column chromatography on silica (200 g) eluting with 0-50% EtOAc-cyclohexane to give the title compound (1.4 g, 21%): $^1$H NMR δ (CDCl$_3$) 3.46 (2H, t, J=7 Hz), 2.96 (2H, t, J=7 Hz), 2.15-2.03 (4H, m), 1.44 (9H, s).

Intermediate 22

4-Bromobutyl 1,1-dimethylethyl sulfone

A solution of 4-bromobutyl 1,1-dimethylethyl sulfide (for example, as prepared for Intermediate 21) (1.4 g, 6.2 mmol) in DCM (15 ml) was treated with m-chloroperbenzoic acid (commercially available, for example, from Aldrich) (4.5 g, 60% pure, 16 mmol) and the mixture was stirred at room temperature overnight. The mixture was diluted with DCM and washed with aqueous sodium bicarbonate solution (×4), water, dried (MgSO$_4$), and evaporated under reduced pressure to give the title compound contaminated with m-chloroperbenzoic acid. The mixture was dissolved in EtOAc and washed with aqueous sodium bicarbonate solution (×4), 2 M sodium hydroxide, dried (MgSO$_4$), and evaporated under reduced pressure to give the title compound (1.14 g, 71%) as a solid: LCMS RT=2.68 min, ES+ve m/z 274/276 [(1:1), (M+NH$_4$)$^+$].

Intermediate 23

3-(Cyclopentylthio)-1-propanol

To a suspension of sodium hydride (commercially available, for example, from Aldrich) (60% dispersion in mineral oil; 800 mg, 20 mmol) in dry DMF (30 ml) was carefully added cyclopentyl mercaptan (commercially available, for example, from Aldrich and/or Alfa Aesar) (2.14 ml, 20 mmol). The resultant suspension was stirred at room temperature, under nitrogen for 15 min before adding 3-bromopropanol (commercially available, for example, from Aldrich) (1.81 ml, 20 mmol). The mixture was then stirred under nitrogen and heated to 80° C. overnight. Water (20 ml) was cautiously added to the reaction mixture, followed by diethyl ether (50 ml). The aqueous solution was extracted with diethyl ether (2×50 ml). The combined organic solutions were washed with water (100 ml) and brine (100 ml) and concentrated in vacuo to leave a yellow oil, which was purified by flash chromatography on silica eluting with cyclohexane-EtOAc (3:1) increasing to (1:1). The solvents were removed in vacuo to afford the title compound (2.18 g). LCMS RT=2.61 min, ES+ve m/z 161 (M+H)$^+$.

Intermediate 24

3-(Cyclopentylthio)propyl methanesulfonate

To a solution of 3-(cyclopentylthio)-1-propanol (for example, as prepared for Intermediate 23) (1.05 g, 6.56 mmol) in dry DCM (5 ml) was added diisopropylethylamine (1.37 ml, 7.87 mmol), and then methanesulfonyl chloride (commercially available, for example, from Aldrich) (0.609 ml, 7.87 mmol) at 20° C. The reaction mixture was stirred at room temperature, under nitrogen for 2.5 h and then diluted with DCM (10 ml) and saturated sodium bicarbonate solution (20 ml). The phases were separated using a hydrophobic frit. The organic phase was concentrated in vacuo to afford the title compound (1.74 g): LCMS RT=3.13 min, ES+ve m/z 239 (M+H)$^+$.

Intermediate 25

3-(Cyclopentylsulfonyl)propyl methanesulfonate

To a solution of 3-(cyclopentylthio)propyl methanesulfonate (for example, as prepared for Intermediate 24) (1.7 g, 6.54 mmol) in DCM (10 ml) was added m-chloroperbenzoic acid (commercially available, for example, from Aldrich) (57-86% pure; 4.46 g, at least 15 mmol). The mixture was stirred at room temperature for about 4 h and then left to stand overnight. The reaction mixture was then diluted with DCM (25 ml) and washed with 2 M sodium metabisulfite solution (×2). The organic solution was then washed with saturated sodium bicarbonate solution (×3), 2 M sodium sulfite (2×100 ml), water (100 ml) and brine (100 ml) and then concentrated in vacuo to afford the title compound (1.8 g). LCMS RT=2.13 min, ES+ve m/z 288 (M+H)$^+$.

Intermediate 26

Ethyl 3-(ethylthio)butanoate

Ethyl crotonate (commercially available, for example, from Aldrich) (2.37 g, 20.8 mmol) was dissolved in DMF (60 ml) and stirred at room temperature. Sodium ethanethiolate (commercially available, for example, from Aldrich) (1.66 g, 19.7 mmol) was added portionwise. On completion of the addition, the mixture was stirred at room temperature overnight. The mixture was diluted with water and extracted with EtOAc (×3). The combined organic solutions were dried (MgSO$_4$), and concentrated in vacuo, for an extensive period of time to remove excess DMF. The residue was applied to a silica cartridge (50 g), eluting with a gradient of EtOAc-cyclohexane (2%-6%) to give the title compound as a colourless oil (527 mg, 14%): $^1$H NMR δ (CDCl$_3$) 4.16 (2H, q, J=9 Hz), 3.28-3.18 (1H, m), 2.66-2.55 (3H, m), 2.44 (1H, dd, J=15, 8 Hz), 1.33 (3H, d, J=7 Hz), 1.31-1.23 (6H, m).

Intermediate 27

3-(Ethylthio)-1-butanol

Ethyl 3-(ethylthio)butanoate (for example, as prepared for Intermediate 26) (526 mg, 2.98 mmol) was dissolved in THF (9 ml) and added dropwise to a stirred solution of lithium aluminium hydride in ether (1.0 M, 6 ml), cooled in an external ice-water bath, and under a nitrogen atmosphere. The mixture was stirred under nitrogen for 2.5 h, and then quenched by the addition of saturated aqueous sodium sulfate solution. The mixture was filtered, and the filtrate was concentrated in vacuo to give the title compound as a colourless oil (493 mg, about 100%, contained some residual THF): $^1$H NMR δ (CDCl$_3$) 3.89-3.72 (2H, m), 3.00-2.91 (1H, m), 2.59 (2H, q, J=7.5 Hz), 1.93-1.77 (2H, m), 1.33 (3H, d, J=7 Hz), 1.27 (3H, t, J=7.5 Hz).

Intermediate 28

3-(Ethylthio)butyl methanesulfonate 3-(Ethylthio)-1-butanol (for example, as prepared for Intermediate 27) (247 mg, 1.84 mmol) was dissolved in DCM (10 ml), and the stirred solution was cooled in an external ice-water bath. Methanesulfonyl chloride (commercially available, for example, from Aldrich) (154 μl, 1.99 mmol) was added and stirring was continued under a nitrogen atmosphere for 2.5 h. The reaction mixture was diluted with further DCM (5 ml) and quenched with saturated aqueous sodium hydrogen carbonate. The layers were separated and the aqueous was extracted with further DCM (×2) (hydrophobic frit). The combined organic solutions were concentrated in vacuo to give the title compound as a colourless oil, which later partially solidified (360 mg, 92%): $^1$H NMR δ (CDCl$_3$) 4.46-4.32 (2H, m), 3.03 (3H, s), 2.98-2.88 (1H, m), 2.57 (2H, q, J=7.5 Hz), 2.03-1.87 (2H, m), 1.35 (3H, d, J=7 Hz), 1.26 (3H, t, J=7 Hz).

Intermediate 29

3-(Ethylsulfonyl)butyl methanesulfonate 3-(Ethylthio)butyl methanesulfonate (for example, as prepared for Intermediate 28) (360 mg, 1.70 mmol) was dissolved in DCM (10 ml) with stirring. The solution was treated with m-chloroperbenzoic acid (commercially available, for example, from Aldrich) (57-86%, 0.90 g, at least 3 mmol), and the mixture was stirred at room temperature for 2.5 h. Excess m-chloroperbenzoic acid was quenched by the addition of aqueous sodium metabisulfite. Saturated aqueous sodium hydrogen carbonate and further DCM were added. The mixture was shaken, the layers were separated, and the aqueous was extracted with further DCM. The combined DCM extracts were washed with further saturated aqueous sodium hydrogen carbonate (×3), dried (MgSO$_4$), and were concentrated in vacuo to give the title compound as a colourless gum (393 mg, 95%): LCMS RT=1.64 min, ES+ve m/z 262 (M+NH$_4$)$^+$ Intermediate 30

2-(2-{4-[(6-Butyl-8-quinolinyl)oxy]-1-piperidinyl}ethyl)-1H-isoindole-1,3(2H)-dione 6-Butyl-8-(4-piperidinyloxy)quinoline (for example, as prepared for Intermediate 4) (2.44 g, 8.59 mmol) was stirred with 2-(2-bromoethyl)-1H-isoindole-1,3(2H)-dione (commercially available, for example, from Acros and/or Aldrich) (2.40 g, 9.4 mmol) and potassium carbonate (5.9 g, 43 mmol) in 2-butanone (75 ml) under nitrogen at 80° C. for 3 days. Further 2-(2-bromoethyl)-1H-isoindole-1,3(2H)-dione (2.4 g, 9.4 mmol) was added and the heating and stirring were continued for a further 24 h. More 2-(2-bromoethyl)-1H-isoindole-1,3(2H)-dione (1.2 g, 4.7 mmol) was added and the heating and stirring were continued for a further 24 h. The mixture was cooled and partitioned between water and DCM. The aqueous layer was extracted with more DCM (×2) and the combined organic layers were washed with water, dried (MgSO$_4$) and evaporated to an oil. This oil was re-dissolved in DCM and loaded onto a column of silica gel (250 g) that had been preconditioned with DCM. The column was eluted with DCM, then DCM-ethanol-0.88 s.g. aqueous ammonia solution (200:8:1) to give the title compound (2.76 g, 6.03 mmol). LCMS RT=2.91 min, ES+ve m/z 458 [M+H]$^+$.

Intermediate 31

1,1-Dimethylethyl(3-{4-[(6-butyl-8-quinolinyl)oxy]-1-piperidinyl}propyl)carbamate 6-Butyl-8-(4-piperidinyloxy)quinoline (for example, as prepared for Intermediate 4) (437 mg, 1.54 mmol) was stirred with 1,1-dimethylethyl (3-bromopropyl)carbamate (commercially available, for example, from Aldrich) (612 mg, 2.57 mmol) and potassium carbonate (426 mg, 3.15 mmol) in 2-butanone (15 ml) under nitrogen at 80° C. overnight. The mixture was cooled and partitioned between water and DCM. The aqueous layer was extracted with more DCM (×2) and the combined organic layers were washed with brine, dried (MgSO$_4$) and evaporated to give a yellow gum. This was purified by flash chromatography (50 g), eluting with 0-30% methanol (containing 1% triethylamine) in DCM. The relevant fractions were concentrated in vacuo to give the title compound as a yellow oil (530 mg, 78%). LCMS RT=2.94 min, ES+ve m/z 442 [M+H]⁺.

Intermediate 32

1,1-Dimethylethyl(4-{4-[(6-butyl-8-quinolinyl)oxy]-1-piperidinyl}butyl)carbamate

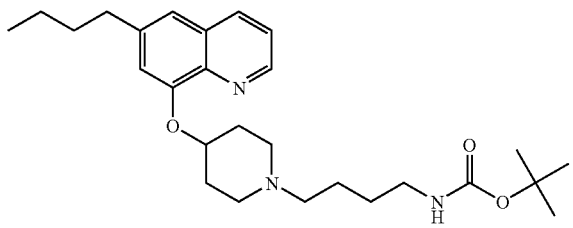

This was prepared in an analogous manner to that disclosed for Intermediate 31 using 6-butyl-8-(4-piperidinyloxy)quinoline (for example, as prepared for Intermediate 4) and 1,1-dimethylethyl (4-bromobutyl)carbamate (commercially available, for example, from Aldrich) instead of 1,1-dimethylethyl (3-bromopropyl) carbamate.

Thus, for example, 6-butyl-8-(4-piperidinyloxy)quinoline (for example, as prepared for Intermediate 4) (855 mg, 3.0 mmol) was stirred with 1,1-dimethylethyl (4-bromobutyl) carbamate (commercially available, for example, from Fluka) (1.12 g, 4.5 mmol) and potassium carbonate (887 mg, 6.4 mmol) in 2-butanone (30 ml) under nitrogen at 80° C. overnight. The mixture was cooled and concentrated in vacuo. The residue was partitioned between water (25 ml) and DCM (25 ml). The aqueous layer was extracted with more DCM (25 ml), and the combined organic layers dried (hydrophobic frit) and concentrated in vacuo. The residue was purified by flash chromatography (silica, 100 g), eluting with 0-15% methanol (containing 1% triethylamine) in DCM over 40 min. The relevant fractions were concentrated in vacuo to give the title compound as a yellow gum (1.29 g, 94%). LCMS RT=3.04 min, ES+ve m/z 456 [M+H]⁺.

Intermediate 33

1,1-Dimethylethyl(5-{4-[(6-butyl-8-quinolinyl)oxy]-1-piperidinyl}pentyl)carbamate This was prepared in an analogous manner to that disclosed for Intermediate 31 using 6-butyl-8-(4-piperidinyloxy)quinoline (for example, as prepared for Intermediate 4), and 1,1-dimethylethyl (5-bromopentyl)carbamate (commercially available, for example, from Toronto). LCMS RT=3.04 min, ES+ve m/z 470 [M+H]⁺.

Intermediate 34

1,1-Dimethylethyl(3-{4-[(6-pentyl-8-quinolinyl)oxy]-1-piperidinyl}propyl) carbamate This was prepared in an analogous manner to that disclosed for Intermediate 31 using 6-pentyl-8-(4-piperidinyloxy)quinoline (for example, as prepared for Intermediate 8) and 1,1-dimethylethyl (3-bromopropyl) carbamate (commercially available, for example, from Aldrich) with a reaction time of 7 h. LCMS RT=3.16 min, ES+ve m/z 456 [M+H]⁺.

Intermediate 35

(2-{4-[(6-Butyl-8-quinolinyl)oxy]-1-piperidinyl}ethyl)amine 2-(2-{4-[(6-Butyl-8-quinolinyl)oxy]-1-piperidinyl}ethyl)-1H-isoindole-1,3(2H)-dione (for example, as prepared for Intermediate 30) (2.76 g, 6.03 mmol) was stirred under nitrogen in ethanol (40 ml) containing hydrazine monohydrate (commercially available, for example, from Aldrich) (0.71 ml, 15.1 mmol) at 80° C. for 2 h. The reaction was cooled with ice-water and filtered. The filter-cake was leached with ethanol and the combined filtrates were evaporated to an oil containing a white solid. This solid was mixed with DCM (about 20 ml) and filtered. The filter-cake was leached with more DCM and the combined filtrates were evaporated to give the title compound (2.07 g) as an oil: LCMS RT=2.32 min, ES+ve m/z 328 [M+H]⁺.

Intermediate 36

(3-{4-[(6-Butyl-8-quinolinyl)oxy]-1-piperidinyl}propyl)amine 1,1-Dimethylethyl(3-{4-[(6-butyl-8-quinolinyl)oxy]-1-piperidinyl}propyl)carbamate (for example, as prepared for Intermediate 31) (493 mg, 1.12 mmol) was treated with a solution of hydrogen chloride in dioxane (4 M, 10 ml), and stirred under nitrogen overnight at room temperature. The mixture was concentrated in vacuo. The residue was dissolved in methanol, and applied to a SCX-2 ion exchange cartridge (10 g) which had been preconditioned with methanol. The cartridge was washed with methanol (100 ml), and then eluted with 10% aqueous 0.88 s.g. ammonia in methanol (100 ml). The relevant basic fractions were concentrated in vacuo to give the title compound (292 mg, 76%). LCMS RT=1.92 min, ES+ve m/z 342 (M+H)⁺.

Intermediate 37

4-{4-[(6-Butyl-8-quinolinyl)oxy]-1-piperidinyl}butyl)amine

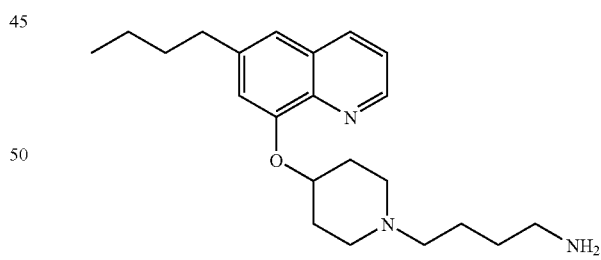

This was prepared in an analogous manner to that disclosed for Intermediate 36, using 1,1-dimethylethyl (4-{4-[(6-butyl-8-quinolinyl)oxy]-1-piperidinyl}butyl)carbamate (for example, as prepared for Intermediate 32).

Thus, for example, 1,1-dimethylethyl (4-{4-[(6-butyl-8-quinolinyl)oxy]-1-piperidinyl}butyl) carbamate (for example, as prepared for Intermediate 32) (1.29 g, 2.84 mmol) was dissolved in MeOH (10 ml) and treated with a solution of hydrogen chloride in dioxane (4 M, 30 ml). The mixture was stirred under nitrogen for 3 h at room temperature. The mixture was concentrated in vacuo. The residue was dissolved in methanol, and applied to a SCX-2 ion exchange cartridge (50 g, pre-conditioned with methanol). The cartridge was washed with methanol (3 column volumes), and then eluted with 10% aqueous 0.88 s.g. ammonia in methanol (3 CV). The relevant basic fractions were concentrated in vacuo to give the title compound as a yellow gum (891 mg, 88%). LCMS RT=2.34 min, ES+ve m/z 356 [M+H]+.

Intermediate 38

(5-{4-[(6-Butyl-8-quinolinyl)oxy]-1-piperidinyl}pentyl)amine

This was prepared in an analogous manner to that disclosed for Intermediate 36, using 1,1-dimethylethyl (5-{4-[(6-butyl-8-quinolinyl)oxy]-1-piperidinyl}pentyl)carbamate (for example, as prepared for Intermediate 33). LCMS RT=2.28 min, ES+ve m/z 370 [M+H]+.

Intermediate 39

(3-{4-[(6-Pentyl-8-quinolinyl)oxy]-1-piperidinyl}propyl)amine

This was prepared in an analogous manner to that disclosed for Intermediate 36, using 1,1-dimethylethyl (3-{4-[(6-pentyl-8-quinolinyl)oxy]-1-piperidinyl}propyl)carbamate (for example, as prepared for Intermediate 34). LCMS RT=2.56 min, ES+ve m/z 356 [M+H]+.

Intermediate 40

4-[(Ethylsulfonyl)amino]butyl ethanesulfonate

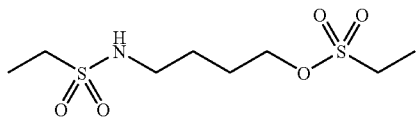

4-Amino-1-butanol (commercially available, for example, from Aldrich) (0.97 g, 11 mmol) was dissolved in DCM (50 ml) together with triethylamine (9.0 ml, 65 mmol), and the stirred solution was cooled to approximately 5° C. in an external ice-water bath under a nitrogen atmosphere. Ethanesulfonyl chloride (commercially available, for example, from Aldrich) (4.09 g, 31.8 mmol), dissolved in DCM (30 ml), was added dropwise, using further DCM (20 ml) to wash in. The reaction mixture was stirred under nitrogen and allowed to warm gradually to room temperature over 4 h. The mixture was diluted with further DCM (100 ml) and washed with saturated aqueous sodium hydrogen carbonate (100 ml). The aqueous layer was extracted with further DCM (100 ml, ×2). The combined organic solutions were dried (MgSO$_4$) and concentrated in vacuo to give the crude product, which was used without further purification in the reaction below (3.11 g): LCMS RT=2.06 min, ES+ve m/z 274 (M+H)+, 291 (M+NH$_4$)+.

On another occasion, a portion of the crude material from an analogous reaction was purified by chromatography. The brown oil (792 mg) was applied to a silica cartridge (50 g, Flashmaster 2), eluting with 0-100% EtOAc-DCM over 40 min to give the pure title compound as a colourless gum (621 mg): LCMS RT=2.15 min, ES+ve m/z 291 (M+NH$_4$)+.

Intermediate 41

3-Chloro-N-(1,1-dimethylethyl)-1-propanesulfonamide

To a solution of 3-chloropropanesulfonyl chloride (commercially available, for example, from Aldrich) (1 g, 6 mmol) in DCM (10 ml) in an ice-water bath was added t-butylamine (commercially available, for example, from Aldrich) (1.3 ml, 12 mmol). The solution was allowed to warm to ambient temperature and stirred for 3 h. The reaction mixture was applied to a SCX-2 cartridge (50 g) (preconditioned with methanol) and the cartridge eluted with methanol (2 column volumes). The methanol fraction was concentrated in vacuo to give the title compound as a white waxy solid (1.17 g, 97%). LCMS RT=2.61 min, ES+ve m/z 214 (M+H)+.

Intermediate 42

N-(1,1-Dimethylethyl)ethenesulfonamide and 2-chloro-N-(1,1-dimethylethyl)ethanesulfonamide (1:1)

This was prepared in an analogous manner to that disclosed for Intermediate 41, using 2-chloro-1-ethanesulfonyl chloride (commercially available, for example, from Aldrich) instead of 3-chloropropanesulfonyl chloride. Yield 65%. LCMS RT=2.04 min, ES+ve m/z 164 (M+H)+ and RT=2.22 min, ES+ve m/z 215/217 (M+NH$_4$)+; $^1$H NMR δ(DMSO-d$_6$) 6.74 (1H, dd, J=16, 10 Hz), 6.0 (1H, d, J=16 Hz), 5.84 (1H, d, J=8 Hz), 3.70 (1H, t, J=8 Hz), 2.86 (1H, t, J=8 Hz) and 1.20 (9H, s).

Intermediate 43

4-Chloro-N-propyl-1-butanesulfonamide

This was prepared in an analogous manner to that disclosed for Intermediate 41, using n-propylamine (commercially available, for example, from Aldrich) instead of t-butylamine, and 4-chloro-1-butanesulfonyl chloride (prepared according to White, E. H.; Lim, H. M. *J. Org. Chem.* 52, 1987, 11, 2162-2166) instead of 3-chloropropane sulfonyl chloride. Yield 88%. LCMS RT=2.54 min, ES+ve m/z 214 (M+H)+.

EXAMPLES

Example 1

6-Butyl-8-({1-[2-(ethylsulfonyl)ethyl]-4-piperidinyl}oxy)quinoline, dihydrochloride salt

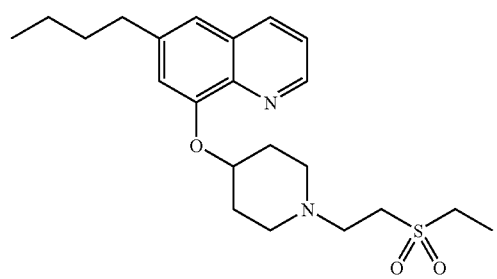

A mixture of 6-butyl-8-(4-piperidinyloxy)quinoline (for example, as prepared for Intermediate 4) (35 mg, 0.12 mmol) sodium bicarbonate (50 mg, 0.6 mmol) in DMF (1 ml) was treated with ethyl vinyl sulfone (commercially available, for example, from Aldrich) (0.6 ml, 5.7 mmol) and the suspension was heated to 100° C. for 15 min in a Smith Creator™ microwave oven. The mixture was diluted with methanol and applied to an SCX-2 cartridge (10 g) eluting with methanol, followed by 10% aqueous 0.88 s.g. ammonia in methanol. The ammoniacal fractions were evaporated under reduced pressure; the residue was dissolved in methanol and re-evaporated. The residue (43 mg) was purified by MDAP and the appropriate fractions were combined and evaporated under reduced pressure to give the formate salt of the title compound (34 mg). The formate salt was then dissolved in methanol (10 ml) and treated with 1.25 M hydrogen chloride in methanol (0.2 ml, 0.25 mmol) and the solvent removed in vacuo to give the title compound (37 mg): LCMS RT=2.71 min, ES+ve m/z 405 (M+H)+.

Example 2

6-Butyl-8-[(1-{2-[(1,1-dimethylethyl)sulfonyl]ethyl}-4-piperidinyl)oxy]quinoline, dihydrochloride salt

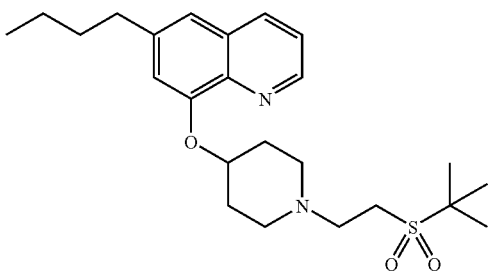

A mixture of 6-butyl-8-(4-piperidinyloxy)quinoline (for example, as prepared for Intermediate 4) (80 mg, 0.28 mmol), sodium iodide (37 mg, 0.25 mmol), sodium bicarbonate (168 mg, 2.0 mmol) and 2-chloroethyl 1,1-dimethylethyl sulfone (for example, as prepared for Intermediate 12) (208 mg, 1.1 mmol) in DMF (2 ml) was heated at 150° C. for 15 min in a Smith Creator™ microwave oven. The reaction mixture was applied to an SCX-2 cartridge (20 g) preconditioned with methanol and was eluted with methanol, followed by 10% aqueous 0.88 s.g. ammonia in methanol. The ammoniacal fractions were combined and concentrated in vacuo and the residue (118 mg) was purified by MDAP (×2). Appropriate fractions were combined and concentrated in vacuo to give the free base of the title compound (10 mg, 8%): This was diluted with methanol and treated with 1.25 M hydrogen chloride solution in methanol (0.05 ml) and the solution was evaporated in vacuo to give the title compound (12 mg): LCMS RT=2.73 min, ES+ve m/z 433 (M+H)+.

Example 3

6-Butyl-8-({1-[3-(methylsulfonyl)propyl]-4-piperidinyl}oxy)quinoline, dihydrochloride salt

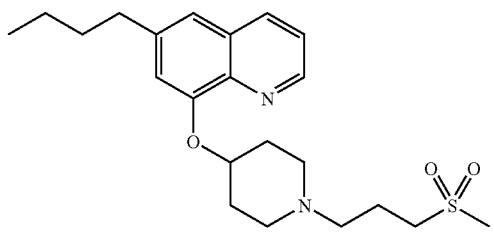

A mixture of 6-butyl-8-(4-piperidinyloxy)quinoline (for example, as prepared for Intermediate 4) (80 mg, 0.28 mmol), sodium iodide (30 mg, 0.2 mmol) and sodium bicarbonate (110 mg, 1.3 mmol) in DMF (2 ml) was treated with a solution of mixture of 3-bromopropyl methyl sulfone and 3-chloropropyl methyl sulfone (for example, as prepared for Intermediate 19) (124 mg) in DMF (0.5 ml) and the mixture was heated at 150° C. for 15 min in a Smith Creator™ microwave oven. The reaction mixture was applied to an SCX-2 cartridge (10 g), preconditioned with methanol, and eluted with methanol, followed by 10% aqueous 0.88 s.g. ammonia in methanol. The ammoniacal fractions were combined and concentrated in vacuo and the residue (126 mg) was purified by MDAP. Appropriate fractions were combined and concentrated in vacuo and the residue (30 mg) was applied to an SCX-2 cartridge (5 g), pre-conditioned with methanol and eluted with methanol, followed by 10% aqueous 0.88 s.g. ammonia in methanol. The ammoniacal fractions were combined and concentrated in vacuo to give the free base of the title compound (21 mg, 18%): This was treated with 1.25 M hydrogen chloride solution in methanol (0.15 ml) and the solution was evaporated in vacuo to give the title compound (22 mg, 89%): LCMS RT=2.49 min, ES+ve m/z 405 (M+H)+.

Example 4

6-Butyl-8-({1-[3-(ethylsulfonyl)propyl]-4-piperidinyl}oxy)quinoline

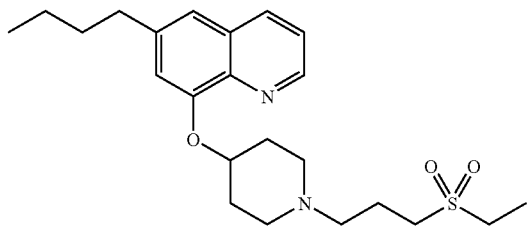

Preparation A (Free Base):

A mixture of 6-butyl-8-(4-piperidinyloxy)quinoline (for example, as prepared for Intermediate 4) (392 mg, 1.38 mmol), sodium iodide (70 mg, 0.46 mmol) and sodium bicarbonate (580 mg, 7 mmol) was treated with a solution of 3-(ethylsulfonyl)propyl 4-methylbenzenesulfonate (for example, as prepared for Intermediate 16) (422 mg, 1.38 mmol) in DMF (10 ml), and the mixture was heated to 100° C. under nitrogen for 5.75 h, then for 3 days at room temperature.

More 3-(ethylsulfonyl)propyl 4-methylbenzenesulfonate (60 mg, 0.2 mmol) was added, and the mixture was stirred at room temperature for 20 h and then heated at 100° C. for 4 h. LCMS indicated no significant change beyond the initial 3 h reaction time and the mixture was partitioned between EtOAc and aqueous sodium bicarbonate. The organic solution was washed with aqueous sodium bicarbonate (×3), brine (×2), dried (MgSO$_4$), and evaporated in vacuo. The residue (722 mg) was dissolved in DCM and purified by chromatography on Flashmaster 2 (silica, 70 g cartridge) eluting with 0-15% methanol (containing 1% triethylamine)-DCM over 40 min. Appropriate fractions were combined and evaporated in vacuo to give the title compound (352 mg, 61%): LCMS RT=2.42 min, ES+ve m/z 419 (M+H)$^+$; $^1$H NMR δ (CDCl$_3$) 8.88 (1H, dd, J=4, 2 Hz), 8.04 (1H, dd, J=8, 2 Hz), 7.37 (1H, dd, J=8, 4 Hz), 7.18 (1H, br s), 6.96 (1H, d, J=1 Hz), 4.64-4.56 (1H, m), 3.13-2.99 (4H, m), 2.97-2.88 (2H, m), 2.76 (2H, t, J=8 Hz), 2.55 (2H, t, J=7 Hz), 2.36-2.25 (2H, m), 2.22-2.13 (2H, m), 2.10-1.99 (4H, m), 1.74-1.58 (4H, m), 1.43 (3H, t, J=7 Hz), 0.96 (3H, t, J=7 Hz).

Preparation B (Dihydrochloride Salt):

To a solution of 6-butyl-8-(4-piperidinyloxy)quinoline (for example, as prepared for Intermediate 4) (0.26 g, 0.91 mmol) in DMF (5 ml) was added a mixture of 3-chloropropyl ethyl sulfone (for example, as prepared for Intermediate 14) (0.182 g, 1.07 mmol), sodium iodide (0.157 g, 1.05 mmol), and then potassium carbonate (0.152 g, 1.1 mmol). The suspension was heated to 150° C. for 15 min in a Smith Creator™ microwave oven, with fixed hold time on. The mixture was applied to an SCX-2 cartridge (20 g), preconditioned with methanol, and the cartridge washed with methanol (2 column volumes). The cartridge was eluted with 10% 0.88 s.g. ammonia in methanol (2 column volumes), the basic fraction was concentrated in vacuo and the residue (0.4 g) was purified by Flashmaster II chromatography (silica, 70 g cartridge), eluting with 0-25% methanol in DCM over 40 min. The appropriate fractions were combined and evaporated in vacuo to give the free base of the title compound (295 mg). LCMS RT=2.7 min, ES+ve m/z 419 (M+H)$^+$; $^1$H NMR δ (CD$_3$OD): 8.45 (1H, t, J=4, 2 Hz), 8.03 (1H, dd, J=8, 2 Hz), 7.30 (1H, dd, J=8, 4 Hz), 7.08 (1H, br s), 6.92 (1H, br s), 4.51 (1H, m), 3.0-2.9 (4H, m), 2.80 (2H, m), 2.60 (2H, t, J=8 Hz), 2.42 (2H, t, J=8 Hz), 2.25 (2H, m), 1.93-2.0 (2H, m), 1.9-1.77 (4H, m), 1.57-1.47 (2H, m), 1.28-1.2 (2H, m), 1.18 (3H, t, J=8 Hz) and 0.78 (3H, t, J=8 Hz). To a solution of the free base of the title compound (295 mg, 0.7 mmol) in methanol (2 ml) was added 1.25 M hydrogen chloride in methanol (1.7 ml). The solvent was removed using a stream of nitrogen and then dried in vacuo to give the title compound as a solid (287 mg, 64%). LCMS RT=2.69 min, ES+ve m/z 419 (M+H)$^+$. Anal. Found: C, 55.30; H, 7.45; N, 5.41% Calcd for (C$_{23}$H$_{34}$N$_2$O$_3$S.2HCl.0.5H$_2$O): C, 55.19; H, 7.45; N, 5.60%.

Example 5

6-Butyl-8-({1-[3-(propylsulfonyl)propyl]-4-piperidinyl}oxy)quinoline, dihydrochloride salt

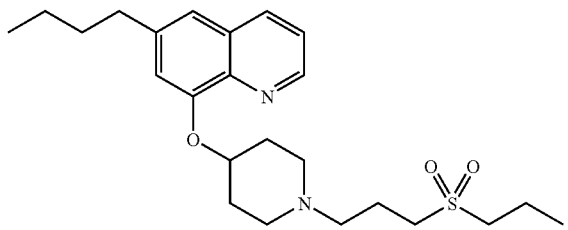

A mixture of 6-butyl-8-(4-piperidinyloxy)quinoline (for example, as prepared for Intermediate 4) (284 mg, 1.00 mmol), sodium iodide (150 mg, 1.0 mmol) and sodium bicarbonate (700 mg, 8 mmol) was treated with a solution of a mixture of 3-bromopropyl propyl sulfone and 3-chloropropyl propyl sulfone (for example, as prepared for Intermediate 18) (4:3, 494 mg) in DMF (6 ml) and the mixture was heated at 100° C. for 18 h under nitrogen. The reaction mixture was allowed to cool to room temperature and partitioned between EtOAc and water. The organic phase was washed with water (×4), brine, dried (MgSO$_4$), and evaporated in vacuo. The residue (681 mg) was dissolved in methanol and applied to an SCX-2 cartridge (50 g) eluting with methanol, followed by 10% aqueous 0.88 s.g. ammonia in methanol. The ammoniacal fractions were combined and evaporated in vacuo. The residue (0.51 g) was dissolved in DCM and purified by chromatography on Flashmaster 2 (silica, 70 g cartridge) eluting with 0-15% methanol (containing 1% triethylamine) in DCM over 40 min. The appropriate fractions were combined and evaporated and the residue (183 mg) was further purified by MDAP to give the formate salt of the title compound (132 mg, 27%): LCMS RT=2.70 min, ES+ve m/z 433 (M+H)$^+$. The formate salt (132 mg, 0.3 mmol) was dissolved in methanol (3 ml) and treated with 1.25 M hydrogen chloride in methanol (0.5 ml). The solvent was removed in vacuo to give the title compound (127 mg, 84%) LCMS RT=2.71 min, ES+ve m/z 433 (M+H)$^+$.

Example 6

6-Butyl-8-[(1-{3-[(1-methylethyl)sulfonyl]propyl}-4-piperidinyl)oxy]quinoline, dihydrochloride salt

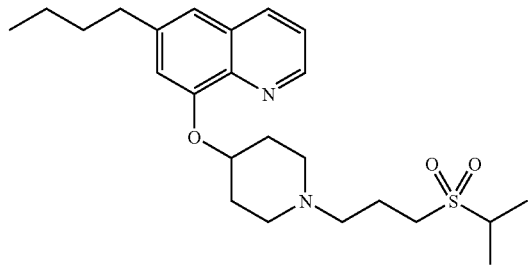

A mixture of 6-butyl-8-(4-piperidinyloxy)quinoline (for example, as prepared for Intermediate 4) (83 mg, 0.29 mmol), sodium iodide (47 mg, 0.3 mmol) and sodium bicarbonate (168 mg, 2 mmol) was treated with a mixture of 3-bromopropyl 1-methylethyl sulfone and 3-chloropropyl 1-methylethyl sulfone (for example, as prepared for Intermediate 20) (57:43, 90 mg) in DMF (1.5 ml) and the mixture was heated at 150° C. for 15 min in a Smith Creator™ microwave oven. The reaction mixture was applied to an SCX-2 cartridge (20 g), preconditioned with methanol, and eluted with methanol, followed by 10% aqueous 0.88 s.g. ammonia in methanol. The ammoniacal fractions were combined and concentrated in vacuo. The residue (160 mg) was purified by MDAP to give the formate salt of the title compound (102 mg, 73%). The formate salt (100 mg, 0.2 mmol) was treated with 1.25 M hydrogen chloride in methanol (4 ml) and the solvent was removed in vacuo to give the title compound (103 mg, 99%): LCMS RT=2.53 min, ES+ve m/z 433 (M+H)$^+$.

Example 7

6-Butyl-8-[(1-{3-[(1,1-dimethylethyl)sulfonyl]propyl}-4-piperidinyl)oxy]quinoline, formate salt

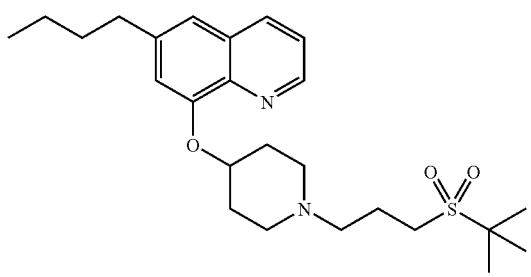

A mixture of 6-butyl-8-(4-piperidinyloxy)quinoline (for example, as prepared for Intermediate 4) (28 mg, 0.10 mmol), sodium iodide (34 mg, 0.23 mmol) and sodium bicarbonate (60 mg, 0.7 mmol) was treated with a mixture of 3-bromopropyl 1,1-dimethylethyl sulfone and 3-chloropropyl 1,1-dimethylethyl sulfone (for example, as prepared for Intermediate 17) (1:1, 40 mg) in DMF (1.5 ml) and heated to at 150° C. for 15 min in a Smith Creator™ microwave oven. The reaction mixture was applied to an SCX-2 cartridge (10 g), preconditioned with methanol, and eluted with methanol, followed by 10% aqueous 0.88 s.g. ammonia in methanol. The ammoniacal fractions were combined and concentrated in vacuo and the residue was purified by MDAP to give the title compound (20 mg, 40%): LCMS RT=2.76 min, ES+ve m/z 447 (M+H)$^+$; $^1$H NMR δ (CD$_3$OD) 8.78 (1H, dd, J=4, 2 Hz), 8.44 (1.6H, s), 8.24 (1H, dd, J=8, 2 Hz), 7.52 (1H, dd, J=8, 4 Hz), 7.32 (1H, br s), 7.19 (1H, br s), 5.03-4.96 (1H, m), 3.68-3.59 (2H, m), 3.40-3.26 (4H, obscured by CD$_3$OD), 3.22 (2H, t, J=7 Hz), 2.79 (2H, t, J=7 Hz), 2.35-2.21 (6H, m), 1.75-1.67 (2H, m), 1.45-1.35 (2H, m), 1.40 (9H, s), 0.96 (3H, t, J=7 Hz).

Example 8

6-Butyl-8-({1-[3-(cyclopentylsulfonyl)propyl]-4-piperidinyl}oxy)quinoline, formate salt (1:1)

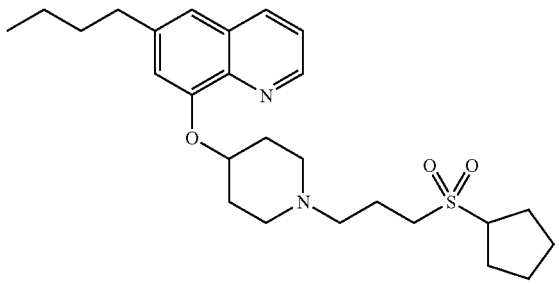

A suspension of 3-(cyclopentylsulfonyl)propyl methanesulfonate (for example, as prepared for Intermediate 25) (0.081 g, 0.3 mmol), 6-butyl-8-(4-piperidinyloxy)quinoline (for example, as prepared for Intermediate 4) (0.102 g, 0.360 mmol), sodium iodide (40 mg, 0.3 mmol) and sodium hydrogen carbonate (200 mg, 2.39 mmol) in dry DMF (2 ml) was heated in a Smith Creator™ microwave oven at 150° C. for 15 min. The reaction mixture was applied to an SCX-2 cartridge (20 g), preconditioned with methanol. The cartridge was washed with methanol (4×25 ml) and then eluted with 10% aqueous 0.88 s.g. ammonia in methanol (4×25 ml). The solvents were removed in vacuo and the resultant residue purified by MDAP to afford the title compound (53 mg): LCMS RT=2.81 min; ES+ve m/z 459 (M+H)$^+$ Example 9

6-Butyl-8-[(1-{4-[(1,1-dimethylethyl)sulfonyl]butyl}-4-piperidinyl)oxy]quinoline, formate salt

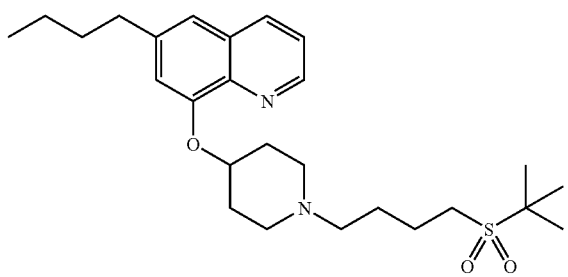

A mixture of 6-butyl-8-(4-piperidinyloxy)quinoline (for example, as prepared for Intermediate 4) (65 mg, 0.23 mmol), sodium iodide (47 mg, 0.3 mmol), sodium bicarbonate (190 mg, 2.2 mmol) and 4-bromobutyl 1,1-dimethylethyl sulfone (for example, as prepared for Intermediate 22) (94 mg) in DMF (2 ml) was heated in a Smith Creator™ microwave oven at 150° C. for 20 min. The reaction mixture was applied to an SCX-2 cartridge (10 g), preconditioned with methanol, and eluted with methanol, followed by 10% aqueous 0.88 s.g. ammonia in methanol. The ammoniacal fractions were combined and concentrated in vacuo and the residue (100 mg) was purified by MDAP to give the title compound (58 mg, 46%): LCMS RT=2.65 min, ES+ve m/z 461 (M+H)+.

Example 10

6-Butyl-8-({1-[3-(ethylsulfonyl)butyl]-4-piperidinyl}oxy)quinoline, dihydrochloride salt

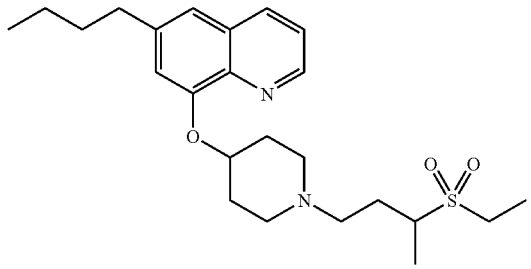

A mixture of 6-butyl-8-(4-piperidinyloxy)quinoline (for example, as prepared for Intermediate 4) (88 mg, 0.31 mmol), sodium hydrogen carbonate (183 mg, 2.18 mmol) and sodium iodide (92 mg, 0.61 mmol) in DMF (3 ml) was treated with 3-(ethylsulfonyl)butyl methanesulfonate (for example, as prepared for Intermediate 29) (143 mg, 0.59 mmol) and the suspension was heated to 150° C. for 30 min in a Smith Creator™ microwave oven. The mixture was diluted with methanol and applied to an SCX-2 cartridge (50 g) eluting with methanol, followed by 10% aqueous 0.88 s.g. ammonia in methanol. The relevant fractions were concentrated, and the residue was purified by MDAP. The appropriate fractions were combined and concentrated in vacuo to give the title compound as the monoformate salt (68 mg, 46%): LCMS RT=2.72 min, ES+ve m/z 433 (M+H)+; A portion of this material (12 mg) was dissolved in methanol and treated with 1.25 M hydrogen chloride in methanol (0.5 ml, excess). The volatiles were removed under a stream of nitrogen to give the title compound (13 mg) as a pale yellow glass: LCMS RT=2.68 min, ES+ve m/z 433 (M+H)+.

Example 11

8-({1-[3-(Ethylsulfonyl)propyl]-4-piperidinyl}oxy)-6-pentylquinoline, dihydrochloride salt

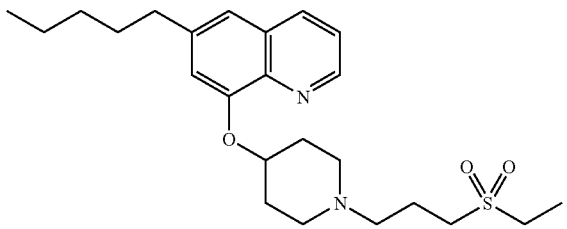

A mixture of 6-pentyl-8-(4-piperidinyloxy)quinoline (for example, as prepared for Intermediate 8) (72 mg, 0.24 mmol), sodium hydrogen carbonate (144 mg, 1.7 mmol), sodium iodide (30 mg, 0.2 mmol) and 3-(ethylsulfonyl)propyl 4-methylbenzenesulfonate (for example, as prepared for Intermediate 16) (68 mg, 0.2 mmol) in DMF (2 ml) was heated to 150° C. for 15 min in a Smith Creator™ microwave oven. The mixture was applied to an SCX-2 cartridge (20 g) eluting with methanol, followed by 10% aqueous 0.88 s.g. ammonia in methanol. The relevant fractions were concentrated, and the residue was applied to a silica cartridge (50 g), eluting with DCM-ethanol-aqueous 0.88 s.g. ammonia (200:8:1 then 100:8:1). One fraction contained clean product, but the material obtained from concentration of a second fraction required further purification by MDAP. The relevant fractions from the MDAP purification were concentrated in vacuo and combined with the pure material from the earlier purification. This material (12 mg) was dissolved in methanol and treated with 1.25 M hydrogen chloride in methanol (0.5 ml, excess). The volatiles were removed under a stream of nitrogen to give the title compound (36 mg, 30%): LCMS RT=2.89 min, ES+ve m/z 433 (M+H)+.

Example 12

6-Butyl-8-[((3R)-1-{3-[(1,1-dimethylethyl)sulfonyl]propyl}-3-pyrrolidinyl)oxy]quinoline, dihydrochloride salt

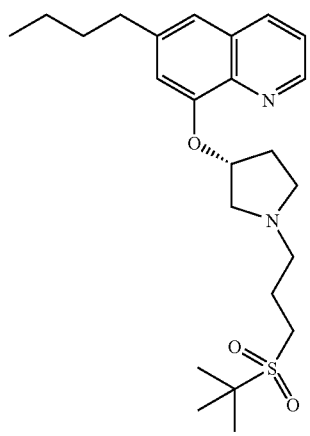

To a solution of 6-butyl-8-[(3R)-3-pyrrolidinyloxy]quinoline (for example, as prepared for Intermediate 10) (0.130 g, 0.481 mmol), in DMF (3 ml) was added a mixture of 3-bromopropyl 1,1-dimethylethyl sulfone and 3-chloropropyl 1,1-dimethylethyl sulfone (for example, as prepared for Intermediate 17) (1:1, 0.215 g, 0.96 mmol), sodium iodide (0.144 g, 0.96 mmol), then potassium carbonate (0.133 g, 0.96 mmol). The suspension was heated to 150° C. for 15 min in a Smith Creator™ microwave oven with fixed hold time on. The mixture was applied to an SCX-2 cartridge (20 g), preconditioned with methanol, and the cartridge washed with methanol (2 column volumes). The cartridge was eluted with 10% 0.88 s.g. ammonia in methanol (2 column volumes) and the basic fraction concentrated in vacuo. The residue (0.2 g) was purified by MDAP and the appropriate fractions combined and concentrated in vacuo. The residue (0.113 g) was further purified by Flashmaster II chromatography (50 g cartridge) eluting with 0-25% methanol in DCM over 40 min. The appropriate fractions were combined and the solvent removed in vacuo (70 mg, 33%). To a portion of this material (29 mg, 0.067 mmol) in methanol (0.5 ml) was added 1.25 M hydrogen chloride in methanol (0.3 ml). The solvent was removed using a stream of nitrogen to leave the title compound as white solid (34 mg). LCMS RT=2.97 min, ES+ve m/z 433 (M+H)+.

Example 13

6-Butyl-8-{[1-(1,1-dioxidotetrahydro-3-thienyl)-4-piperidinyl]oxy}quinoline

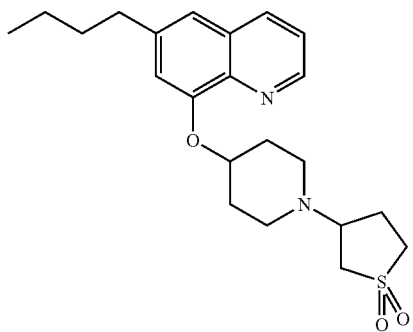

To a solution of 6-butyl-8-(4-piperidinyloxy)quinoline (for example, as prepared for Intermediate 4) (0.15 g, 0.53 mmol) in THF (5 ml) was added 2,3-dihydrothiophene 1,1-dioxide (commercially available, for example, from AKOS) (0.150 g, 1.27 mmol). The solution was heated to 80° C. for 2.5 h. To the solution at ambient temperature was added a further amount of 2,3-dihydrothiophene 1,1-dioxide (0.150 g, 1.27 mmol) and the solution stirred overnight at ambient temperature. The solution was heated to reflux for 2 h and then at ambient temperature for 7 days. The reaction was applied to an SCX-2 cartridge (20 g), preconditioned with methanol, and the cartridge washed with methanol (2 column volumes). The cartridge was eluted with 10% 0.880 s.g. ammonia in methanol (2 column volumes) and the basic fractions concentrated in vacuo. The residue was purified by MDAP and the appropriate fractions combined and evaporated. The combined fractions were applied to an SCX-2 cartridge (20 g), preconditioned with methanol, and the cartridge washed with methanol. The cartridge was eluted with 10% 0.88 s.g. ammonia in methanol (2 column volumes) and the basic fractions concentrated in vacuo to give the title compound (17 mg, 8%). LCMS RT=2.59 min, ES+ve m/z 403 (M+H)+.

Example 14

N-(2-{4-[(6-Butyl-8-quinolinyl)oxy]-1-piperidinyl}ethyl)ethanesulfonamide, dihydrochloride salt

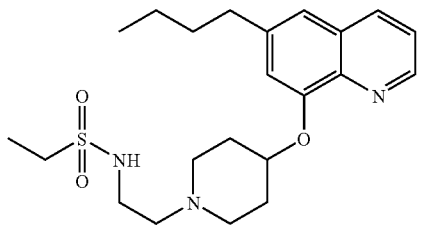

This was prepared in an analogous manner to that disclosed for Example 24 using (2-{4-[(6-butyl-8-quinolinyl)oxy]-1-piperidinyl}ethyl)amine (for example, as prepared for Intermediate 35) (26 mg, 0.08 mmol), triethylamine (56 μl, 0.4 mmol), and ethanesulfonyl chloride (commercially available, for example, from Aldrich) (19 μl, 0.2 mmol) in DCM (2 ml). The title compound was obtained as the formate salt: LCMS RT=2.36 min, ES+ve m/z 420 (M+H)+. The material was dissolved in methanol and treated with 1.25 M hydrogen chloride in methanol (0.6 ml, excess). The volatiles were removed under a stream of nitrogen to give the title compound (15 mg, 38%); LCMS RT=2.68 min, ES+ve m/z 420 (M+H)+.

Example 15

N-(2-{4-[(6-Butyl-8-quinolinyl)oxy]-1-piperidinyl}ethyl)-2-methyl-1-propanesulfonamide, dihydrochloride salt

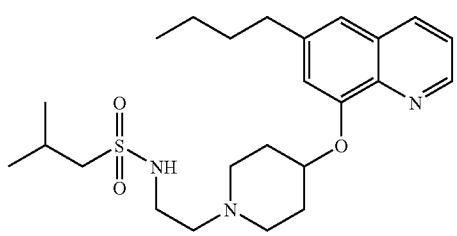

This was prepared in an analogous manner to that disclosed for Example 24 using (2-{4-[(6-butyl-8-quinolinyl)oxy]-1-piperidinyl}ethyl)amine (for example, as prepared for Intermediate 35) (20 mg, 0.06 mmol), triethylamine (56 μl, 0.4 mmol), and isobutane sulfonyl chloride (commercially available, for example, from Aldrich) (26 μl, 0.2 mmol) in DCM (2 ml). The title compound was obtained as the formate salt: LCMS RT=2.97 min, ES+ve m/z 448 (M+H)+. The material was dissolved in methanol and treated with 1.25 M hydrogen chloride in methanol (0.6 ml, excess). The volatiles were removed under a stream of nitrogen to give the title compound (6 mg, 19%); LCMS RT=2.94 min, ES+ve m/z 448 (M+H)+.

Example 16

N-(2-{4-[(6-Butyl-8-quinolinyl)oxy]-1-piperidinyl}ethyl)benzenesulfonamide, dihydrochloride salt

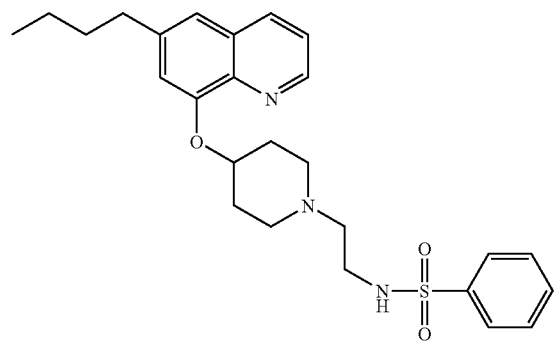

(2-{4-[(6-Butyl-8-quinolinyl)oxy]-1-piperidinyl}ethyl)amine (for example, as prepared for Intermediate 35) (50 mg, 0.15 mmol) was stirred with triethylamine (0.1 ml, 0.7 mmol) in DCM (2 ml) at room temperature under nitrogen and benzenesulphonyl chloride (commercially available, for example, from Aldrich) (29 µL, 0.22 mmol) was added. After 20 min, LCMS showed the reaction was complete. The solution was poured onto a Bond Elute silica cartridge (10 g), preconditioned with DCM. The cartridge was eluted with this solvent, and then DCM-ethanol-0.88 s.g. aqueous ammonia solution (200:8:1) to give, after evaporation, the crude free base of the title compound (55 mg). This was dissolved in dimethylsulfoxide-methanol (1:1; 1 ml) and purified by MDAP to give, after evaporation, the formate salt of the title compound: LCMS RT=2.96 min, ES+ve m/z 468 (M+H)$^+$. 1.25 M hydrogen chloride in methanol (0.75 ml, excess) was added to this material and the solution was evaporated to dryness and dried to give the title compound (39 mg, 48%): LCMS RT=2.95 min, ES+ve m/z 468 (M+H)$^+$.

Example 17

N-(3-{4-[(6-Butyl-8-quinolinyl)oxy]-1-piperidinyl}propyl)ethanesulfonamide, dihydrochloride salt

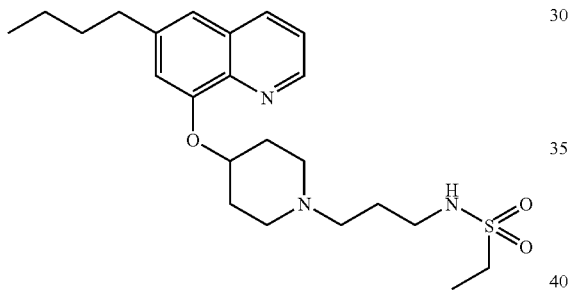

(3-{4-[(6-Butyl-8-quinolinyl)oxy]-1-piperidinyl}propyl)amine (for example, as prepared for Intermediate 36) (30 mg, 0.09 mmol) was dissolved in DCM (1 ml), and treated with triethylamine (38 µl, 0.27 mmol), and ethanesulfonyl chloride (commercially available, for example, from Aldrich) (17 µl, 0.18 mmol). The mixture was stirred in a stoppered vial at room temperature for 1 h, then left to stand at room temperature overnight. The mixture was diluted with methanol and applied to an SCX-2 cartridge (5 g) eluting with methanol, followed by 10% aqueous 0.88 s.g. ammonia in methanol. The relevant fractions were concentrated, and the residue was purified by MDAP. The appropriate fractions were combined and concentrated to give the title compound as the monoformate salt (29 mg, 67%): LCMS RT=2.62 min, ES+ve m/z 434 (M+H)$^+$. The material was dissolved in methanol and treated with 1.25 M hydrogen chloride in methanol (excess). The volatiles were removed under a stream of nitrogen to give the title compound (30 mg): LCMS RT=2.63 min, ES+ve m/z 434 (M+H)$^+$.

Example 18

N-(3-{4-[(6-Butyl-8-quinolinyl)oxy]-1-piperidinyl}propyl)-1-propanesulfonamide, dihydrochloride salt

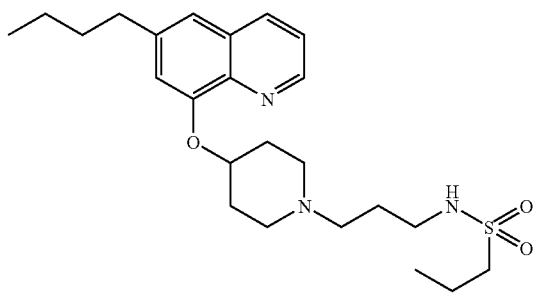

This was prepared in an analogous manner to that disclosed for Example 24 using (3-{4-[(6-butyl-8-quinolinyl)oxy]-1-piperidinyl}propyl)amine (for example, as prepared for Intermediate 36) (30 mg, 0.09 mmol), triethylamine (38 µl, 0.27 mmol), and propanesulfonyl chloride (commercially available, for example, from Aldrich) (20 µl, 0.18 mmol) in DCM (1 ml). The title compound was obtained as the partial formate salt (approximately 0.5 equivalents formate) (36 mg, 85%). The material was dissolved in methanol and treated with 1.25 M hydrogen chloride in methanol (excess). The volatiles were removed under a stream of nitrogen to give the title compound (30 mg): LCMS RT=2.73 min, ES+ve m/z 448 (M+H)$^+$.

Example 19

N-(3-{4-[(6-Butyl-8-quinolinyl)oxy]-1-piperidinyl}propyl)-2-propanesulfonamide, dihydrochloride salt

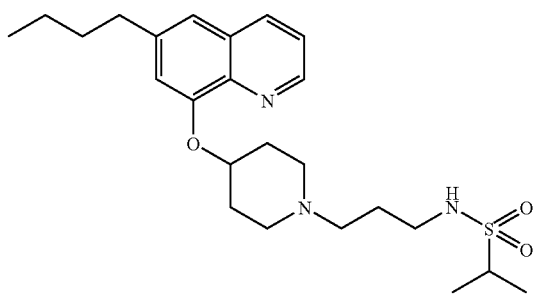

(3-{4-[(6-Butyl-8-quinolinyl)oxy]-1-piperidinyl}propyl)amine (for example, as prepared for Intermediate 36) (30 mg, 0.09 mmol) was dissolved in DCM (1 ml), and treated with triethylamine (38 µl, 0.27 mmol), and 2-propanesulfonyl chloride (commercially available, for example, from Aldrich) (20 µl, 0.18 mmol). The mixture was stirred in a stoppered vial at room temperature for 1 h, then left to stand at room temperature overnight. LCMS analysis indicated that reaction was not complete. Further triethylamine (38 µl, 0.27 mmol), and 2-propanesulfonyl chloride (17 µl, 0.18 mmol) were added and the mixture stirred at room temperature for 1.5 h. LCMS analysis indicated that reaction was still not complete. Further triethylamine (19 µl, 0.14 mmol), and 2-propanesulfonyl chloride (10 µl, 0.09 mmol) were added and the mixture stirred at room temperature overnight. The mixture was diluted with methanol and applied to an SCX-2 cartridge (5 g) eluting with methanol, followed by 10% aqueous 0.88 s.g. ammonia in methanol. The relevant fractions were concentrated, and the residue was purified by MDAP. The appropriate fractions were combined and concentrated, but the product was found to contain an impurity, thought to be (3-{4-[(6-butyl-8-quinolinyl)oxy]-1-piperidinyl}propyl)sulfamic acid. The material was dissolved in methanol and applied to an aminopropyl cartridge (5 g) eluting with methanol. The relevant fractions were combined and concentrated to give the title compound as the free base: LCMS RT=2.68 min, ES+ve m/z 448 (M+H)+. The material was dissolved in methanol and treated with 1.25 M hydrogen chloride in methanol (0.5 ml, excess). The volatiles were removed under a stream of nitrogen to give the title compound (13 mg, 27%): LCMS RT=2.80 min, ES+ve m/z 448 (M+H)+.

Example 20

N-(3-{4-[(6-Pentyl-8-quinolinyl)oxy]-1-piperidinyl}propyl)ethanesulfonamide, dihydrochloride salt

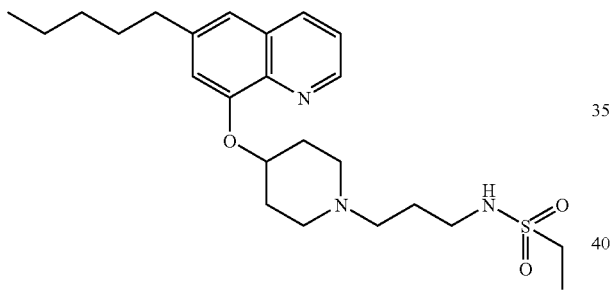

This was prepared in an analogous manner to that disclosed for Example 24 using (3-{4-[(6-pentyl-8-quinolinyl)oxy]-1-piperidinyl}propyl)amine (for example, as prepared for Intermediate 39) (37 mg, 0.1 mmol), triethylamine (18 μl, 0.13 mmol), and ethanesulfonyl chloride (commercially available, for example, from Aldrich) (12 μl, 0.12 mmol) in DCM (2 ml). The title compound was obtained as the formate salt: LCMS RT=2.90 min, ES+ve m/z 448 (M+H)+. The material was dissolved in methanol and treated with 1.25 M hydrogen chloride in methanol (0.5 ml, excess). The volatiles were removed under a stream of nitrogen to give the title compound as a yellow gum (24 mg, 46%): LCMS RT=2.86 min, ES+ve m/z 448 (M+H)+.

Example 21

N-(3-{4-[(6-Pentyl-8-quinolinyl)oxy]-1-piperidinyl}propyl)-1-propanesulfonamide, dihydrochloride salt

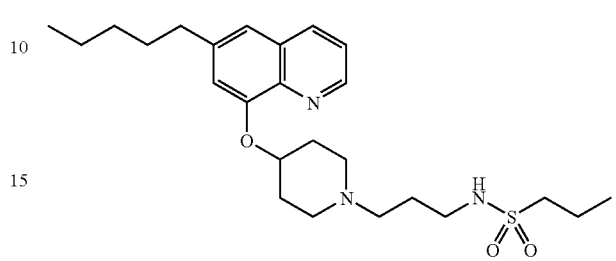

This was prepared in an analogous manner to that disclosed for Example 24 using (3-{4-[(6-pentyl-8-quinolinyl)oxy]-1-piperidinyl}propyl)amine (for example, as prepared for Intermediate 39) (35 mg, 0.1 mmol), triethylamine (18 μl, 0.13 mmol), and 1-propanesulfonyl chloride (commercially available, for example, from Aldrich) (14 μl, 0.12 mmol) in DCM (2 ml). The title compound was obtained as the formate salt: LCMS RT=2.98 min, ES+ve m/z 462 (M+H)+. The material was dissolved in methanol and treated with 1.25 M hydrogen chloride in methanol (0.5 ml, excess). The volatiles were removed under a stream of nitrogen to give the title compound as a yellow gum (24 mg, 45%): LCMS RT=2.98 min, ES+ve m/z 462 (M+H)+.

Example 22

N-(4-{4-[(6-Butyl-8-quinolinyl)oxy]-1-piperidinyl}butyl)methanesulfonamide, dihydrochloride salt

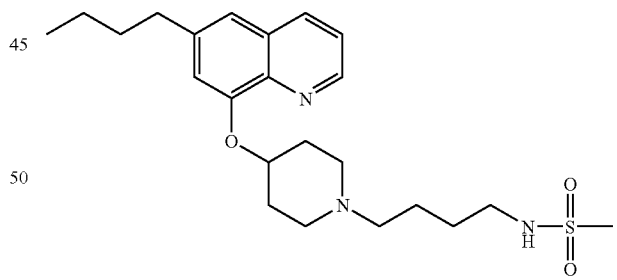

This was prepared in an analogous manner to that disclosed for Example 24 using (4-{4-[(6-butyl-8-quinolinyl)oxy]-1-piperidinyl}butyl)amine (for example, as prepared for Intermediate 37) (40 mg, 0.11 mmol), triethylamine (24 μl, 0.18 mmol), and methanesulfonyl chloride (commercially available, for example, from Aldrich) (10 μl, 0.14 mmol) in DCM (2 ml). The title compound was obtained as the formate salt: LCMS RT=2.65 min, ES+ve m/z 434 (M+H)+. The material was dissolved in methanol and treated with 1.25 M hydrogen chloride in methanol (0.5 ml, excess). The volatiles were removed under a stream of nitrogen to give the title compound (20 mg, 36%); LCMS RT=2.65 min, ES+ve m/z 434 (M+H)+.

Example 23A

N-(4-{4-[(6-Butyl-8-quinolinyl)oxy]-1-piperidinyl}butyl)ethanesulfonamide

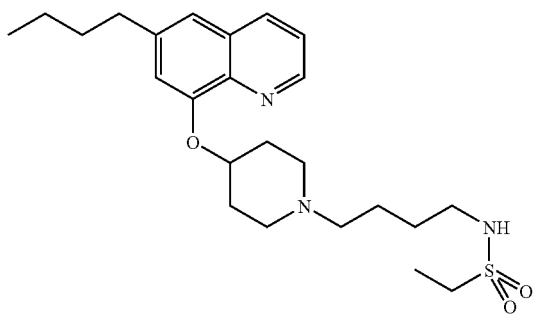

Preparation A:

6-Butyl-8-(4-piperidinyloxy)quinoline (for example, as prepared for Intermediate 4) (575 mg, 2.02 mmol) and 4-[(ethylsulfonyl)amino]butyl ethanesulfonate (for example, as prepared for Intermediate 40) (1.10 g, impure, estimated as 2.8 mmol) were dissolved in DMF (20 ml). Sodium hydrogen carbonate (845 mg, 10.1 mmol) and sodium iodide (602 mg, 4.02 mmol) were added. The mixture was heated at 60° C. with stirring overnight (16 h) under a nitrogen atmosphere. LCMS analysis showed that unreacted starting material was present, so further 4-[(ethylsulfonyl)amino]butyl ethanesulfonate (402 mg, impure, estimated as 1.0 mmol) and DMF (5 ml) were added and the mixture was heated for a further 10 h. The mixture was diluted with water (100 mL) and extracted with toluene (100 ml, then 50 ml×3). The combined organic extracts were dried (MgSO$_4$) and concentrated in vacuo to give the crude material as a brown oil (1.89 g). This was applied to an SCX-2 cartridge (50 g, pre-conditioned with methanol [100 mL] then with acetonitrile [100 mL]), eluting with acetonitrile (200 ml) (or, alternatively methanol), followed by 10% aqueous 0.88 s.g. ammonia in acetonitrile (300 ml) (or, alternatively methanol). The basic fractions were concentrated in vacuo to give a brown gum (approximately 600 mg). This was applied to a silica cartridge (50 g), eluting with DCM-ethanol-aqueous 0.88 s.g. ammonia (200:8:1, 418 ml, then 150:8:1, 477 ml, then 100:8:1, 436 ml). Relevant fractions were concentrated in vacuo to give the title compound (free base) as a brown oil (522 mg, 58%): LCMS RT=2.60 min, ES+ve m/z 448 (M+H)+; $^1$H NMR δ (CD$_3$OD) 8.72 (1H, dd, J=4, 2 Hz), 8.20 (1H, dd, J=8, 2 Hz), 7.47 (1H, dd, J=8, 4 Hz), 7.25 (1H, s), 7.09 (1H, d, J=1.5 Hz), 4.72-4.64 (1H, m), 3.09-2.99 (4H, m), 2.98-2.90 (2H, m), 2.78 (2H, t, J=7.5 Hz), 2.47-2.36 (4H, m), 2.18-2.09 (2H, m), 2.05-1.94.

Preparation B:

(4-{4-[(6-Butyl-8-quinolinyl)oxy]-1-piperidinyl}butyl) amine (for example, as prepared for Intermediate 37) (248 mg, 0.7 mmol) was dissolved in DCM (5 ml), and treated with triethylamine (156 µl, 1.12 mmol), and ethanesulfonyl chloride (commercially available, for example, from Aldrich) (80 µl, 0.84 mmol). The mixture was stirred at room temperature for 2 h, then left to stand at room temperature overnight. The mixture was washed with saturated aqueous sodium hydrogen carbonate, passed through a hydrophobic frit and the organic solution was concentrated in vacuo. The residue was applied to a silica cartridge (20 g), eluting with DCM-ethanol-aqueous 0.88 s.g. ammonia (100:8:1). The relevant fractions were concentrated in vacuo to give the title compound (as the free base) as a yellow gum (167 mg). LCMS RT=2.66 min, ES+ve m/z 448 (M+H)+; $^1$H NMR δ (CD$_3$OD) 8.72 (1H, dd, J=4, 1.5 Hz), 8.21 (1H, dd, J=8, 1.5 Hz), 7.48 (1H, dd, J=8, 4 Hz), 7.26 (1H, s), 7.10 (1H, s), 4.74-4.64 (1H, m), 3.10-2.92 (6H, m), 2.78 (2H, t, J=7.5 Hz), 2.50-2.38 (4H, m), 2.20-2.10 (2H, m), 2.08-1.95 (2H, m), 1.76-1.53 (6H, m), 1.47-1.36 (2H, m), 1.30 (3H, t, J=7 Hz), 0.97 (3H, t, J=7 Hz).

Example 23B

N-(4-{4-[(6-Butyl-8-quinolinyl)oxy]-1-piperidinyl}butyl)ethanesulfonamide, dihydrochloride salt For this method the following abbreviations are used:

eqv: equivalent (1 eq=1 mole reagent per 1 mole of starting material)

kg: kilograms

L: litres vol: volume (1 vol=1 ml per gram starting material)

wt: weight (1 wt=1 g reagent per 1 g starting material)

Scheme 11

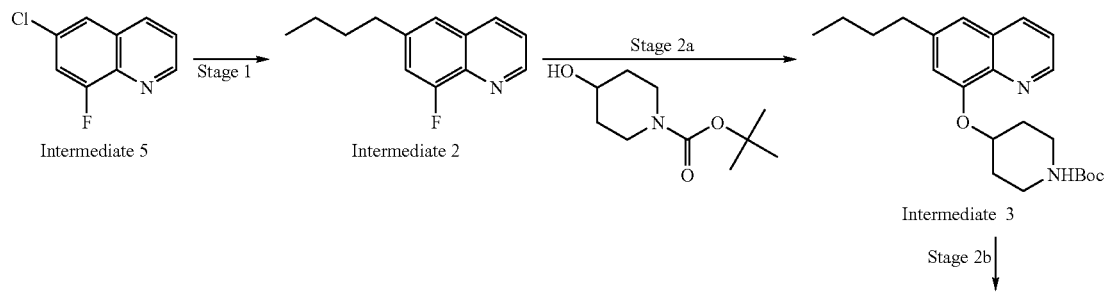

Stage 2b

-continued

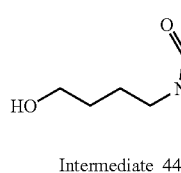
Intermediate 44

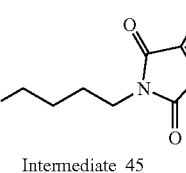
Intermediate 45

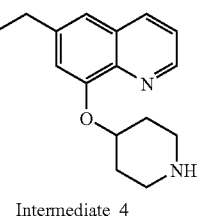
Intermediate 4

Stage 3b

Stage 3a

Stage 4a

HO—NH₂

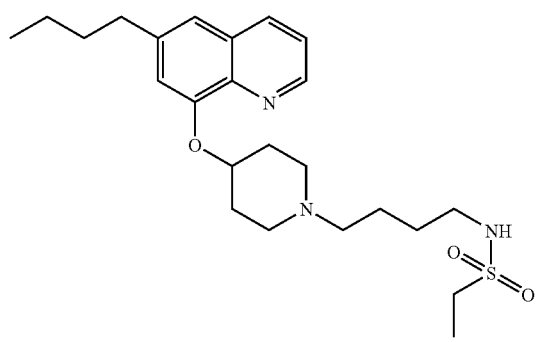
Intermediate 46

Stage 4b

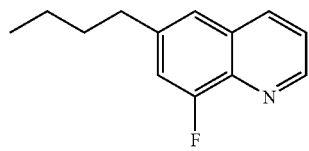
Example 23B

Stage 5

Intermediate 37

Intermediate 2

Stage 1

6-Butyl-8-fluoroquinoline

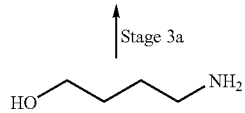

Under nitrogen, 6-chloro-8-fluoroquinoline (for example, as prepared for Intermediate 5) (4.6 kg, 1.0 eqv) was added to N-methylpyrrolidinone (46 L, 10 vol). To this mixture, ferric acetylacetonate (0.89 kg, 0.1 eqv) was added and the reaction mass cooled to 0 to −10° C. A solution of n-butyl magnesium chloride (commercially available, for example, from Aldrich) (14.84 L, 1.35 eqv of 2.3M grignard in tetrahydrofuran) was added slowly over approximately 4 hours at between 0 to −10° C. and the reaction was stirred for 10 to 20 min. The progress of the reaction was monitored by HPLC. As there was more than 2% starting material a further portion of n-butyl magnesium chloride was added (0.52 L, 0.05 eqv of 2.3M grignard in tetrahydrofuran) at 0 to −10° C. over 10 to 30 min. After passing the HPLC (starting material not more than 2%), the reaction mixture was quenched with ammonium chloride solution (4.6 kg, 1 wt, in 101 L water) keeping the temperature below 35° C., an the reaction mixture was stirred at approximately 27° C. for 15-30 min. A dilute solution of aqueous HCl (3.5 vol, 14.6 L [made up as bulk solution of 4.6 L 35% HCl in 13.8 L water]) was then added into the reaction mixture until pH 1-2 was reached. The reaction mass was extracted at pH 1 to 2 with ethyl acetate (46 L, then 28 L×3). The combined organic layers were then washed with water (69 L, 15 vol) and dilute ammonia solution (46 L [41.4 L water and 4.6 L 22.38% aqueous ammonia solution). The organic layer was washed with water (55.2 L×3), the organic layer was separated and concentrated in vacuo (vacuum no less than 600 mm Hg), keeping the temperature below 70° C.

Toluene (4.6 L, 1 vol) was then added and the mixture concentrated in vacuo (vacuum no less than 600 mm Hg), keeping the temperature below 70° C. to a crude oil to remove traces of ethyl acetate. The residue was diluted in toluene (6.9 L, 1.5 vol) and added to n-hexane (138 L, 30 vol) with stirring at 25-35° C. After 1 to 2 hr, the mass was filtered through celite (4.6 kg) and the celite bed was washed with mixture of toluene and hexane (1:10, 0.92 L, 0.2 vol toluene and 9.2 L, 2 vol hexane) followed by hexane washing (46 L, 10 vol). The combined filtrate was stirred with silica gel (6.9 kg, 1.5 wt) for 1.5 to 2.5 hr at 25-35° C. Silica gel was filtered off and filtered silica gel was washed with a mixture of hexane and triethylamine (20:1 mixture, 5×48.3 L). The combined filtrate was then concentrated twice in vacuo (vacuum not less than 600 mm Hg) keeping the temperature below 70° C. Toulene (4.6 L, 1 vol) was then added to the residue (approximately 10 L) and again concentrated in vacuo (vacuum not less than 650 mm Hg) keeping the temperature below 70° C. to remove traces of solvent (toluene less than 10%). The residue was cooled, unloaded and stored under nitrogen. The title compound was obtained in 82.5% yield (4.25 kg) and in 99.0% purity.

$^1$H NMR (400 MHz, CDCl$_3$) δppm/TMS 0.95 (3H, t), 1.4 (2H, m), 1.7 (2H, m), 2.75 (2H, q), 7.25 (1H, m), 7.4 (2H, m—partly obscured by CHCl$_3$), 8.1 (1H, d), 8.9 (1H, d)

Intermediate 4

Stages 2a and 2b

6-Butyl-8-(4-piperidinyloxy)quinoline

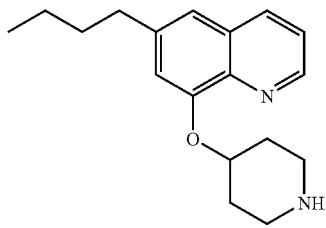

Under a nitrogen atmosphere, N-Boc-4-hydroxypiperidine (commercially available, for example, from Aldrich) (11.66 kg, 1.5 eqv) and sodium tert-butoxide (5.5 kg, 1.5 eqv) was charged into a reactor containing N-methylpyrrolidinone (39.25 L, 5 vol) and stirred at approximately 25° C. to obtain a clear solution. In another reactor under a nitrogen atmosphere was charged 6-butyl-8-fluoroquinoline (for example, as obtained from Stage 1) (7.85 kg, 1.0 eqv) and N-methylpyrrolidinone (31.4 L, 4 vol) under nitrogen and heated to approximately 110° C. over 1-3 hr. From the first reactor, the solution of N-Boc-4-hydroxypiperidine sodium salt in N-methylpyrrolidinone was added slowly over 2-3 hr into the second reactor containing 6-butyl-8-fluoroquinoline in N-methylpyrrolidinone at approximately 110° C. The reaction mixture was stirred for approximately 1 hr at approximately 110° C. and progress of the reaction was monitored by HPLC (starting material not more than 2%). After completion of reaction, the temperature was adjusted to 30-40° C. and a saturated solution of ammonium chloride (7.85 kg ammonium chloride in 157 L water, 20 vol) was added into the reaction mass below 40° C. To this reaction mixture, ethyl acetate (78.5 L, 10 vol) was added followed by acetic acid (1.15 L, 0.15 vol) and stirred well. The organic layer was separated, and aqueous layer was again extracted with ethyl acetate (39.25 L, 5 vol). The combined organics were then washed with water (78.5 L, 10 vol×3). The combined organics were concentrated in vacuo (vacuum not less than 600 mm Hg), keeping the temperature below 60° C. To the concentrated reaction mass, toluene (23.55 L, 3 vol) was added, and the reaction mixture concentrated in vacuo (vacuum not less than 600 mm Hg), keeping the temperature below 60° C. To this crude mass again fresh toluene (78.5 L, 10 vol) was added, followed by 22.8% HCl in iso-propyl alcohol (24.51 L, 3.36 eqv), and reaction mixture was stirred at 70-80° C. for 1-2 hr. The progress of the reaction was monitored by HPLC (starting material less than 2% by HPLC). After completion of reaction, the reaction was cooled to 30-40° C. and water (78.5 L, 10 vol) was added portionwise into the reaction mixture, stirred well and the layers separated. The aqueous layer was washed three times with dichloromethane (78.5 L, 10 vol, then 54.95 L, 7 vol, then 39.25 L, 5 vol). The aqueous layer was slowly basified with sodium hydroxide solution (7.85 kg in 54.95 L water) until pH was 12.5 to 13.5. The product was extracted in dichloromethane (78.5 L, 10 vol, then 39.25 L, 5 vol, ×2). The combined dichloromethane layers were washed with aqueous sodium chloride solution (7.85 kg in 78.5 L water, ×3). The combined organics were concentrated in vacuo (vacuum no less than 600 mm Hg) keeping the temperature below 50° C. In order to remove traces if dichloromethane, N,N'-dimethylformamide (23.6 L, 3 vol) was added and the reaction mass was held at a vacuum of no less than 650 mm Hg, keeping the temperature below 50° C. The title compound (3.76 kg, 34.24% yield) was obtained as solution in N,N'-dimethylformamide and stored at approximately 5° C.

$^1$H NMR (400 MHz, CDCl$_3$) δppm/TMS 0.95 (3H, t), 1.4 (2H, m), 1.7 (2H, m), 1.9 (2H, m), 2.2 (2H, dd), 2.75 (2H, m), 2.85 (2H, m), 3.3 (2H, m), 4.7 (1H, m), 7.0 (1H, s), 7.2 (1H, s), 7.35 (1H, m), 8.05 (1H, m), 8.85 (1H, d)

Intermediate 45

Stages 3a and 3b 4-(1,3-dioxo-1,3-dihydro-2H-isoindol-2-yl)butyl ethanesulfonate

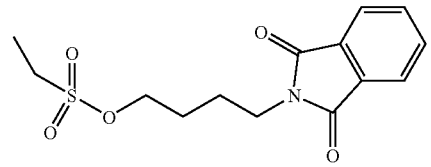

To a solution of 4-aminobutanol (commercially available, for example, from Aldrich) (2.6 kg, 1 eqv) in toluene (65 L, 25 vol) at 25-35° C. was added phthalic anhydride (commercially available, for example, from Aldrich) (4.3 kg, 1 eqv). The temperature of the reaction mixture was slowly raised to 80-90° C. for 2-3 hr and then heated to reflux to azeotropically remove the water from the reaction mass. The progress of the reaction was monitored by TLC, and after passing the TLC (starting material not more than 2%), approximately 25-40% of toluene was removed from reaction by atmospheric distillation. The reaction mass was then cooled to 0-5° C. and triethylamine (4.4 kg, 1.5 eqv) was charged to the reaction mass over 15 min. Ethane sulphonyl chloride (commercially available, for example, from Aldrich) (4.5 kg, 1.2 eqv) diluted in toluene (7.8 L, 3 vol) was slowly added into the reaction mass at 0-5° C. under a nitrogen atmosphere. The reaction mixture was stirred for approximately 2 hr, then monitored by HPLC (starting material not more than 2%). After completion of reaction, water (26 L, 10 vol) and triethylamine (2.6 kg, 1 vol) was added to the reaction mass, and stirred at 30-35° C. for 10-30 min, and then filtered over celite (1.3 kg, 0.5 wt, pre-conditioned with toluene, 2.6 L, 1 vol). The celite was then washed with hot toluene (40-50° C., 10.4 L, 4 vol), and the organic layer was separated. The aqueous layer was extracted with toluene (7.8 L, 3 vol) and combined organic layers were then washed with aqueous sodium bicarbonate solution (2.6 kg in 26 L water) and water (13 L, 5 vol). The organic layer was concentrated in vacuo (vacuum no less than 600 mm Hg), keeping the temperature below 70° C. Iso-propylalcohol (7.8 L, 3 vol) was added and the reaction mass was concentrated in vacuo (vacuum no less than 600 mm Hg), keeping the temperature below 70° C. To this concentrated mass, iso-propylalcohol (26 L, 10 vol) was added, and warmed to 50-60° C. to give a clear solution. This solution was cooled to 35-45° C. and n-hexane (26 L, 10 vol) was added slowly and then cooled to 25-35° C. The reaction mass was stirred for 1.5 to 2.5 hr and filtered by centrifugation. The wet cake was washed with n-hexane (31 L, 11.9 vol) and filtered again by centrifugation. The material was dried in vacuo (vacuum no less than 650 mm Hg) for 10-12 hr at 50-55° C. The title compound was isolated in 78.36% yield (7.1 kg) and 99.6% purity.

$^{1}$H NMR (400 MHz, CDCl$_3$) δppm/TMS 1.4 (3H, t), 1.8 (4H, m), 3.15 (2H, m), 3.7 (2H, m), 4.25 (2H, m), 7.75 (2H, m), 7.85 (2H, m)

Intermediate 37

Stages 4a and 4b

4-{4-[(6-Butyl-8-quinolinyl)oxy]-1-piperidinyl}butyl)amine

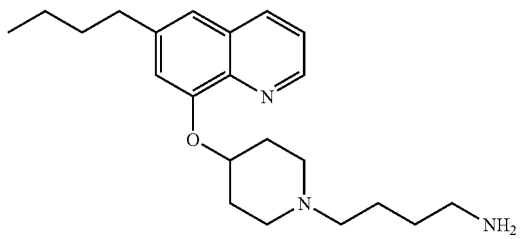

To a solution of 6-butyl-8-(4-piperidinyloxy)quinoline (for example, as prepared for Intermediate 4 in stages 2a and 2b) (3.76 kg, 1 eqv) in N,N'-dimethylformamide (7.52 L, 2 vol) was added tetrabutylammonium iodide (commercially available, for example, from Aldrich) (0.019 kg, 0.005 wt), sodium iodide (1.98 kg, 1 eqv), diisopropylethylamine (3.42 kg, 2 eqv), and 4-(1,3-dioxo-1,3-dihydro-2H-isoindol-2-yl)butyl ethanesulfonate (for example, as prepared for Intermediate 45 in stages 3a and 3b) (4.32 kg, 1.1 eqv) under nitrogen atmosphere at 25-35° C. The reaction mass was warmed to about 70-80° C. and maintained at that temperature for 10-12 hr. The reaction was monitored by HPLC (starting material not more than 1.5%). After the completion of reaction, the reaction mixture was cooled to 30-40° C. The reaction mixture was diluted with water (37.6 L, 10 vol) followed by toluene (37.6 L, 10 vol). To the reaction mixture was then added activated carbon (0.38 kg, 0.1 wt) and celite (0.94 kg, 0.25 wt) and warmed to 50-60° C. for 15-30 min. The reaction mixture was stirred and cooled to 25-35° C., then filtered over celite (celite bed made with 1 kg celite, 18.8 L water, 5 vol). The celite bed was then washed with hot (50-60° C.) toluene (18.8 L, 5 vol). The combined filtrates were separated and the aqueous layer was extracted with toluene (18.8 L, 5 vol, ×3). The combined organic layers were washed with water (37.6 L, 10 vol, ×3). The organic layer was washed with concentrated [37.36%] aqueous HCl (22.56 L, 6 vol) and the aqueous HCl layer containing product was collected. The aqueous HCl layer was then heated to reflux (110-120° C.) and 5-10% of solvent was distilled off. Reflux was then continued for a further 10-12 hr. An aliquot of sample was submitted for HPLC (starting material not more than 2%), then the reaction mixture was cooled to 5-15° C., stirred for 30-60 min, filtered in vacuo and the filter cake was washed with cooled (5-15° C.) water (7.52 L, 2 vol). The resulting filtrate was basified by slow addition of sodium hydroxide solution (19.5 L NaOH solution [made with 11.28 kg NaOH and 22.56 L water]) to pH 4-5. The aqueous layer was then washed with dichloromethane/iso-propylalcohol (10:1, 41.36 L, 11 vol, then 20.68 L, 5.5 vol×2). The pH of the aqueous layer containing product was slowly adjusted to pH 8 to 9 keeping the temperature at approximately 30° C. by adding sodium hydroxide solution (2 L NaOH solution [made with 11.28 kg NaOH and 22.56 L water]). The aqueous layer was then extracted with dichloromethane (37.6 L, 10 vol, then 18.8 L, 5 vol, then 11.28 L, 3 vol), and the combined organics were washed with a solution of dilute ammonia (37.6 L ammonia solution [15.04 L ammonia (22.38%) and 22.56 L water]) and iso-propylalcohol (18.8 L, 5 vol), followed by dilute ammonia (37.6 L ammonia solution, [15.04 L ammonia (22.38%) and 22.56 L water]×2). 20-40% of dichloromethane solvent was removed by distillation at atmospheric pressure. The remaining mixture was concentrated in vacuo (vacuum no less than 650 mm Hg), keeping the temperature below 40-45° C. The residue was diluted with dichloromethane (1.88 L, 0.5 vol) and can be stored under nitrogen at 2-8° C. for up to 3 days. The title compound was isolated in 56.68% yield (2.57 kg) and 86% purity.

$^{1}$H NMR (400 MHz, CDCl$_3$) δppm/TMS 0.95 (3H, t), 1.4 (2H, m), 1.5 (4H, m), 1.7 (2H, m), 2.05 (2H, m), 2.2 (2H, m), 2.3 (2H, m), 2.4 (2H, m), 2.75 (4H, m), 2.95 (2H, m), 4.6 (1H, m), 6.95 (1H, s), 7.2 (1H, s), 7.35 (1H, d), 8.0 (1H, d), 8.85 (1H, d)

Example 23B

Stage 5

N-(4-[4-[(6-Butyl-8-quinolinyl)oxy]-1-piperidinyl]butyl)ethanesulfonamide, dihydrochloride salt To a solution of 4-{4-[(6-butyl-8-quinolinyl)oxy]-1-piperidinyl}butyl)amine (for example, as prepared for Intermediate 37 in stages 4a and 4b) (2.57 kg, 1.0 eqv) was added dichloromethane (30.84 L, 12 vol), and triethylamine (2.05 kg, 2.8 eqv) under a nitrogen atmosphere. The reaction mixture was cooled to 0-5° C. and a solution of ethanesulphonyl chloride (commercially available, for example, from Aldrich) (1.86 kg, 2.0 eqv) in dichloromethane (7.71 L, 3 vol) was added dropwise at 0-10° C. After stirring for 2-3 hr at 0-10° C. under nitrogen, the reaction temperature was adjusted to 25-35° C. and stirred for 2-3 hr. A sample was analysed by HPLC to monitor reaction progress. The reaction mixture was quenched at 25-35° C. with water (25.7 L, 10 vol). The organic layer was separated and the aqueous layer extracted with dichloromethane (7.71 L, 3 vol). The combined organics were washed with citric acid solution (5.14 kg, 2 wt dissolved in 25.7 L water, 10 vol). The aqueous layer containing product was collected and the organic layer was again washed with aqueous citric acid solution (0.77 kg, 0.3 wt, dissolved in 3.34 L water, 1.3 vol) and the organic layer was separated. The combined aqueous layers were washed with dichloromethane (12.8 L, 5 vol). Dilute ammonia solution (12.85 L ammonia (22.38%) dissolved in 12.85 L water) was then added to the aqueous layer keeping the temperature at 30-35° C., until the pH reached was between 10-12. The product from the aqueous layer was then extracted with dichloromethane (25.7 L, 10 vol, then 7.71, 3 vol) and the combined organics were again washed with dilute ammonia solution (5.14 L ammonia (22.38%) dissolved in 5.14 L water). The organic layer was finally washed twice with water (25.7 L, 10 vol) then 50-80% solvent was removed by distillation under atmospheric pressure, keeping the temperature below 55° C. The reaction mixture was then concentrated in vacuo (vacuum no less than 600 mm Hg) keeping the temperature below 50° C. To this crude mixture, iso-propylalcohol (7.71 L, 3 vol) was added and concentrated in vacuo (vacuum no less than 600 mm Hg) keeping the temperature below 50° C. To this, methanol (17.99 L, 7 vol) and activated carbon (0.13 kg, 0.05 wt) were added sequentially, and stirred for 15-30 min. The charcoal was filtered over a celite bed (prepared using 1.5 kg celite and 7.71 L methanol), then washed with methanol (7.71 L, 3 vol) and to the combined filtrate, HCl in iso-propylalcohol (22.8%, 3.6 L, 2.65 eqv) was added at 20-30° C., and stirred for 15-30 min. The reaction mass was then concentrated in vacuo (vacuum no less than 650 mm Hg) until a syrup remained which started to solidify, then methanol (12.85 L, 5 vol) was added to the residue to obtain a clear solution. The reaction mass was then stirred at 30-35° C., and ethyl acetate (51.4 L, 20 vol) was added. The reaction mass was then stirred for 1-2 hr at 25-35° C. and then cooled to 5-10° C. for 1-2 hr, then centrifuged. The solid was then washed with methanol: ethyl acetate mixture (1:7, 2.57 L methanol in 17.99 L ethyl acetate) at 5-10° C. and centrifuged. The product was dried in vacuo (vacuum no less than 650 mm Hg) at 50-55° C. for 8-12 hrs. The title compound was obtained in 53.15% yield (2 kg).

$^1$H NMR (400 MHz, CDCl$_3$) δ ppm/TMS 0.95 (3H, t), 1.4 (5H, m), 1.7 (4H, m), 2.1 (2H, m), 2.2 (2H, d), 2.9 (4H, m), 3.0 (2H, m), 3.2 (2H, m), 3.5 (4H, m), 4.4 (2H, broad s), 5.3 (1H, s), 6.4 (1H, s), 7.4 (1H, s), 7.5 (1H, s), 7.95 (1H, d), 8.8 (1H, d), 9.3 (1H, s), 11.3 (1H, s), 17.1 (1H, s)

Recrystallisation of N-(4-[4-[(6-Butyl-8-quinolinyl) oxy]-1-piperidinyl]butyl)ethane sulfonamide, dihydrochloride salt Example 23B Stage 6

A solution of N-(4-{4-[(6-butyl-8-quinolinyl)oxy]-1-piperidinyl}butyl)ethanesulfonamide, dihydrochloride salt (for example, as prepared for Example 23B in stage 5) (2 kg, 1 eqv) in methanol (8 L, 4 vol) at 25-35° C. was passed through catridge filters (1 micron, followed by 0.2 micron frit) and the line flushed with methanol (2 L, 1 vol). The filtrate was cooled to 25-30° C. and stirred for 30 min to ensure complete dissolution. Ethyl acetate (4.4 L, 2.2 vol) was slowly added into the reaction mixture, which was then seeded with N-(4-{4-[(6-butyl-8-quinolinyl)oxy]-1-piperidinyl}butyl)ethanesulfonamide, dihydrochloride salt (0.0048 kg, 0.0024 wt) and aged isothermally for 30-45 min at 25-30° C. Further ethyl acetate (35.6 L, 17.8 vol) was added slowly over 2-2.5 hr, keeping the temperature between 25-30° C., then stirred at this temperature for 30 min. The reaction mixture was slowly cooled to 0-10° C., and stirred at this temperature for an additional 2-3 hrs. The product was filtered through a centrifuge and washed with pre-chilled (0-10° C.) ethyl acetate (4 L, 2 vol). The cake was offloaded, spin-dried then dried in vacuo (vacuum no less than 600 mm Hg) at 55-60° C. for 12-14 hrs to give the title compound in 85.55% yield (1.72 kg) and 98.59% purity.

An XRPD pattern of N-(4-{4-[(6-Butyl-8-quinolinyl) oxy]-1-piperidinyl}butyl)ethanesulfonamide, dihydrochloride salt (as prepared for Example 23B) is shown in FIG. 1 and FIG. 2. The peak angles and d-spacings for this form are tabulated below:

| Two theta (°) | d-spacing (Å) |
|---|---|
| 10.3 | 8.6 |
| 12.5 | 7.1 |
| 15.5 | 5.7 |
| 20.7 | 4.3 |
| 23.0 | 3.9 |
| 24.9 | 3.6 |
| 27.6 | 3.2 |

Example 24

N-(4-{4-[(6-Butyl-8-quinolinyl)oxy]-1-piperidinyl}butyl)-1-propanesulfonamide, dihydrochloride salt

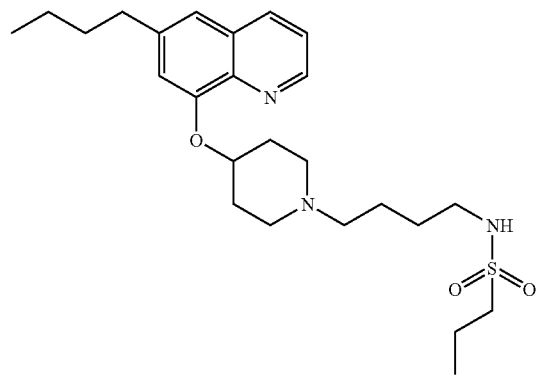

(4-{4-[(6-Butyl-8-quinolinyl)oxy]-1-piperidinyl}butyl) amine (for example, as prepared for Intermediate 37) (36 mg, 0.1 mmol) was dissolved in DCM (2 ml) with stirring, and treated with triethylamine (22 μl, 0.16 mmol), and 1-propanesulfonyl chloride (commercially available, for example, from Aldrich) (14 μl, 0.12 mmol). The mixture was stirred at room temperature for 1 h. The mixture was washed with saturated aqueous sodium hydrogen carbonate, and the aqueous layer was extracted with further DCM (×2) (hydrophobic frit). The combined organic solutions were concentrated, and the residue was purified by MDAP. The appropriate fractions were combined and concentrated to give the title compound as the formate salt: LCMS RT=2.89 min, ES+ve m/z 462 (M+H)$^+$.

The material was dissolved in methanol and treated with 1.25 M hydrogen chloride in methanol (0.6 ml, excess). The volatiles were removed in vacuo to give the title compound (17 mg 32%): LCMS RT=2.88 min, ES+ve m/z 462 (M+H)+.

Example 25

N-(4-{4-[(6-Butyl-8-quinolinyl)oxy]-1-piperidinyl}butyl)-2-propanesulfonamide, dihydrochloride salt

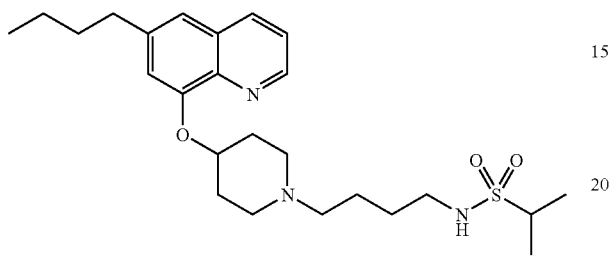

(4-{4-[(6-Butyl-8-quinolinyl)oxy]-1-piperidinyl}butyl)amine (for example, as prepared for Intermediate 37) (87 mg, 0.24 mmol) was dissolved in DCM (2 ml), and treated with triethylamine (167 µl, 1.2 mmol), and 2-propanesulfonyl chloride (commercially available, for example, from Aldrich) (54 µl, 0.48 mmol). The mixture was stirred at room temperature for 1.5 h. LCMS analysis indicated that reaction was not complete. Further triethylamine (167 µl, 1.2 mmol), and 2-propanesulfonyl chloride (54 µl, 0.48 mmol) were added and the mixture stirred at room temperature for 1 h. The reaction was quenched by the addition of methanol then concentrated under a stream of nitrogen. The residue was re-dissolved in methanol and applied to an SCX-2 cartridge (20 g) eluting with methanol, followed by 10% aqueous 0.88 s.g. ammonia in methanol. The relevant fractions were concentrated, and the residue was purified by MDAP. The appropriate fractions were combined and concentrated, but the product was found to contain impurities, thought to be (3-{4-[(6-butyl-8-quinolinyl)oxy]-1-piperidinyl}propyl)sulfamic acid. The material was dissolved in methanol and applied to an aminopropyl cartridge (5 g) eluting with methanol. The relevant fractions were combined and concentrated to give the title compound as the free base (43 mg, 39%): LCMS RT=2.63 min, ES+ve m/z 462 (M+H)+. Approximately half the material was dissolved in methanol and treated with 1.25 M hydrogen chloride in methanol (1 ml, excess). The volatiles were removed under a stream of nitrogen to give the title compound (26 mg): LCMS RT=2.70 min, ES+ve m/z 462 (M+H)+.

Example 26

N-(4-{4-[(6-Butyl-8-quinolinyl)oxy]-1-piperidinyl}butyl)-2-methyl-1-propanesulfonamide, dihydrochloride salt

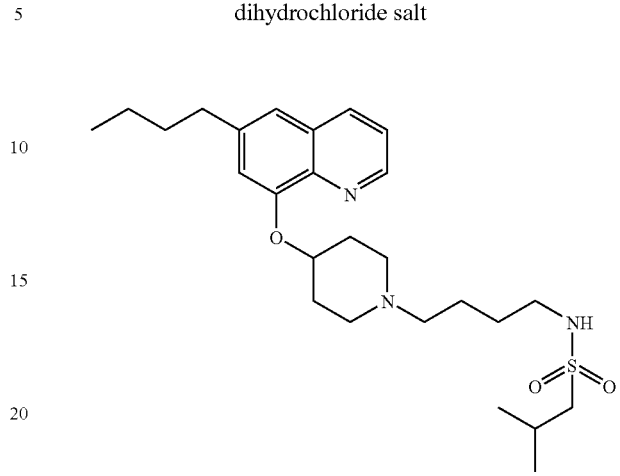

(4-{4-[(6-Butyl-8-quinolinyl)oxy]-1-piperidinyl}butyl)amine (for example, as prepared for Intermediate 37) (39 mg, 0.11 mmol) was dissolved in DCM (2 ml) with stirring, and treated with triethylamine (25 µl, 0.18 mmol), and isobutanesulfonyl chloride (commercially available, for example, from Aldrich) (17 µl, 0.13 mmol). The mixture was stirred at room temperature for 1 h, then treated with further triethylamine (13 µl, 0.09 mmol), and isobutanesulfonyl chloride (13 µl, 0.10 mmol). The mixture was stirred at room temperature for a further 30 min. The mixture was washed with saturated aqueous sodium hydrogen carbonate, and the aqueous layer was extracted with further DCM (×2) (hydrophobic frit). The combined organic solutions were concentrated, and the residue was purified by MDAP. The appropriate fractions were combined and concentrated to give the title compound as the formate salt: LCMS RT=3.05 min, ES+ve m/z 476 (M+H)+. The material was dissolved in methanol and treated with 1.25 M hydrogen chloride in methanol (0.6 ml, excess). The volatiles were removed under a stream of nitrogen to give the title compound (11 mg, 18%): LCMS RT=3.02 min, ES+ve m/z 476 (M+H)+.

Example 27

N-(4-{4-[(6-Butyl-8-quinolinyl)oxy]-1-piperidinyl}butyl)cyclohexanesulfonamide, dihydrochloride salt

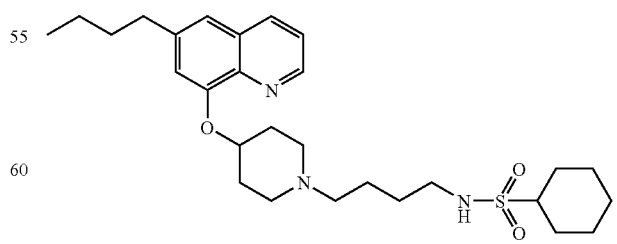

(4-{4-[(6-Butyl-8-quinolinyl)oxy]-1-piperidinyl}butyl)amine (for example, as prepared for Intermediate 37) (74 mg, 0.2 mmol) was dissolved in DCM (2 ml), and treated with triethylamine (55 μl, 0.4 mmol), and cyclohexanesulfonyl chloride (commercially available, for example, from Aldrich) (44 μl, 0.30 mmol). The mixture was stirred at room temperature for 1 h. LCMS analysis indicated that reaction was not complete. Further triethylamine (55 μl, 0.4 mmol), and cyclohexanesulfonyl chloride (20 ml, 0.1 mmol) were added and the mixture stirred at room temperature for overnight. The reaction was quenched by the addition of methanol then concentrated under a stream of nitrogen. The residue was re-dissolved in methanol and applied to an SCX-2 cartridge (20 g) eluting with methanol, followed by 10% aqueous 0.88 s.g. ammonia in methanol. The relevant fractions were concentrated, and the residue was purified by MDAP. The appropriate fractions were combined and concentrated to give the title compound as the formate salt: LCMS RT=3.08 min, ES+ve m/z 502 (M+H)$^+$. The material was dissolved in methanol and treated with 1.25 M hydrogen chloride in methanol (0.5 ml, excess). The volatiles were removed under a stream of nitrogen to give the title compound (26 mg, 23%): LCMS RT=3.06 min, ES+ve m/z 502 (M+H)$^+$.

Example 28

N-(4-{4-[(6-Butyl-8-quinolinyl)oxy]-1-piperidinyl}butyl)-1-cyclohexyl methane sulfonamide, dihydrochloride salt

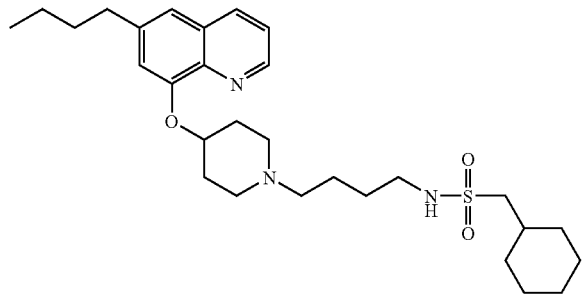

This was prepared in an analogous manner to that disclosed for Example 24 using (4-{4-[(6-butyl-8-quinolinyl)oxy]-1-piperidinyl}butyl)amine (for example, as prepared for Intermediate 37) (42 mg, 0.12 mmol), triethylamine (26 μl, 0.19 mmol), and cyclohexylmethanesulfonyl chloride (commercially available, for example, from Array Biopharma) (39 mg, 0.20 mmol) in DCM (2 ml). The title compound was initially obtained as the formate salt, but required further purification. The salt was re-dissolved in methanol and applied an SCX-2 cartridge (5 g) eluting with methanol, followed by 10% aqueous 0.88 s.g. ammonia in methanol. The relevant basic fractions were concentrated in vacuo to provide the title compound as the free base: LCMS RT=3.31 min, ES+ve m/z 516 (M+H)$^+$. The material was dissolved in methanol and treated with 1.25 M hydrogen chloride in methanol (1 ml, excess). The volatiles were removed under a stream of nitrogen to give the title compound (26 mg, 37%): LCMS RT=3.29 min, ES+ve m/z 516 (M+H)$^+$.

Example 29

N-(4-{4-[(6-Butyl-8-quinolinyl)oxy]-1-piperidinyl}butyl)-N-methylethanesulfonamide, dihydrochloride salt

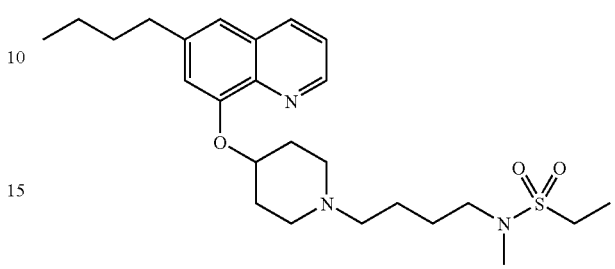

DMF (0.5 ml) was added to sodium hydride (60% dispersion in oil, 20 mg, 0.5 mmol) and the mixture was stirred under nitrogen at room temperature. N-(4-{4-[(6-Butyl-8-quinolinyl)oxy]-1-piperidinyl}butyl)ethanesulfonamide (for example, as prepared for Example 23, preparation A) (56 mg, 0.125 mmol) was added as a solution in DMF (2 ml), and the mixture stirred for 10 min. Methyl iodide (commercially available, for example, from Aldrich) (17 mg, 0.125 mmol) was added as a solution in DMF (200 μl), and the reaction was stirred under nitrogen at room temperature for 1.5 h. The mixture was diluted with methanol and applied to an SCX-2 cartridge (50 g) eluting with methanol, followed by 10% aqueous 0.88 s.g. ammonia in methanol. The relevant fractions were concentrated, and the residue was purified by MDAP. The appropriate fractions were combined and concentrated to give the title compound as the formate salt: LCMS RT=2.68 min, ES+ve m/z 462 (M+H)$^+$. The material was dissolved in methanol and treated with 1.25 M hydrogen chloride in methanol (0.5 ml, excess). The volatiles were removed under a stream of nitrogen to give the title compound (35 mg, 52%): LCMS RT=2.76 min, ES+ve m/z 462 (M+H)$^+$.

Example 30

N-(4-{4-[(6-Pentyl-8-quinolinyl)oxy]-1-piperidinyl}butyl)ethanesulfonamide, dihydrochloride salt

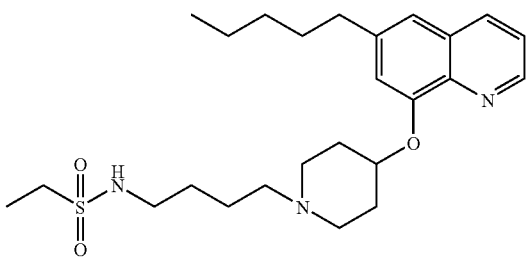

A mixture of 6-pentyl-8-(4-piperidinyloxy)quinoline (for example, as prepared for Intermediate 8) (62 mg, 0.2 mmol) and 4-[(ethylsulfonyl)amino]butyl ethanesulfonate (for example, as prepared for Intermediate 40) (80 mg, 0.24 mmol), sodium hydrogen carbonate (120 mg, 1.4 mmol) and sodium iodide (29 mg, 0.19 mmol) in DMF (2 ml) was heated to 150° C. for 15 min in a Smith Creator™ microwave oven.

LCMS analysis showed that reaction was incomplete, so further 4-[(ethylsulfonyl)amino]butyl ethanesulfonate (26 mg, 0.1 mmol) and DMF (0.5 ml) were added and the mixture was heated for 15 min further at 150° C. in a Smith Creator™ microwave oven. LCMS analysis showed that reaction was still incomplete, so the mixture was transferred to a flask, diluting with further DMF (2 ml). Further 4-[(ethylsulfonyl)amino]butyl ethanesulfonate (80 mg, 0.29 mmol) and DMF (1 ml) were added and the mixture was heated to 60° C. for 3 h under nitrogen. Further 4-[(ethylsulfonyl)amino]butyl ethanesulfonate (82 mg, 0.3 mmol), sodium iodide (60 mg, 0.4 mmol) and DMF (1 ml) were added and the mixture was heated to 60° C. overnight under nitrogen. The reaction mixture was concentrated in vacuo. The residue was applied to an SCX-2 cartridge (20 g) eluting with methanol, followed by 10% aqueous 0.88 s.g. ammonia in methanol. The relevant fractions were concentrated, and the residue was purified by MDAP. The appropriate fractions were combined and concentrated to give the title compound as the formate salt: LCMS RT=2.92 min, ES+ve m/z 462 (M+H)$^+$. The material was dissolved in methanol and treated with 1.25 M hydrogen chloride in methanol (0.5 ml, excess). The volatiles were removed under a stream of nitrogen to give the title compound (15 mg, 14%): LCMS RT=2.95 min, ES+ve m/z 462 (M+H)$^+$.

Example 31

N-(5-{4-[(6-Butyl-8-quinolinyl)oxy]-1-piperidinyl}pentyl)methanesulfonamide, dihydrochloride salt

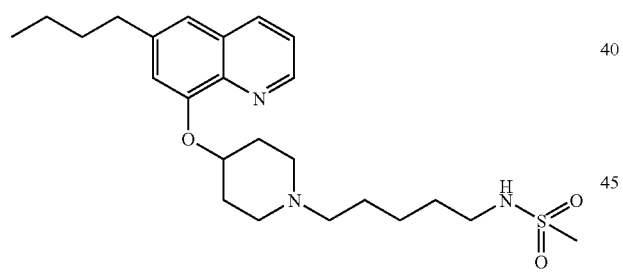

This was prepared in an analogous manner to that disclosed for Example 24 using (5-{4-[(6-butyl-8-quinolinyl)oxy]-1-piperidinyl}pentyl)amine (for example, as prepared for Intermediate 38) (35 mg, 0.1 mmol), triethylamine (22 µl, 0.16 mmol), and methanesulfonyl chloride (commercially available, for example, from Aldrich) (9 µl, 0.12 mmol) in DCM (2 ml). The title compound was obtained as the formate salt: LCMS RT=2.71 min, ES+ve m/z 448 (M+H)$^+$. The material was dissolved in methanol and treated with 1.25 M hydrogen chloride in methanol (0.5 ml, excess). The volatiles were removed under a stream of nitrogen to give the title compound (32 mg, 61%); LCMS RT=2.71 min, ES+ve m/z 448 (M+H)$^+$.

Example 32

N-(5-{4-[(6-Butyl-8-quinolinyl)oxy]-1-piperidinyl}pentyl)ethanesulfonamide, dihydrochloride salt

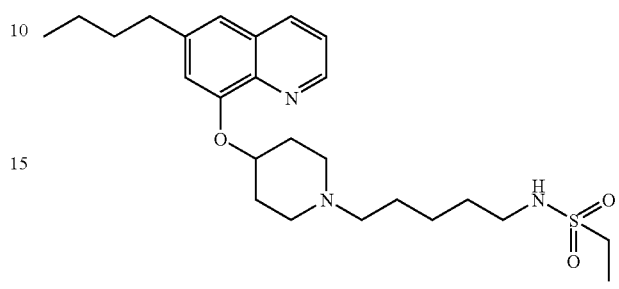

This was prepared in an analogous manner to that disclosed for Example 24 using (5-{4-[(6-butyl-8-quinolinyl)oxy]-1-piperidinyl}pentyl)amine (for example as prepared for Intermediate 38) (44 mg, 0.12 mmol), triethylamine (27 µl, 0.19 mmol), and ethanesulfonyl chloride (commercially available, for example, from Aldrich) (14 µl, 0.14 mmol) in DCM (2 ml). The title compound was obtained as the formate salt: LCMS RT=2.79 min, ES+ve m/z 462 (M+H)$^+$. The material was dissolved in methanol and treated with 1.25 M hydrogen chloride in methanol (0.5 ml, excess). The volatiles were removed under a stream of nitrogen to give the title compound (38 mg, 59%); LCMS RT=2.78 min, ES+ve m/z 462 (M+H)$^+$.

Example 33

2-{4-[(6-Butyl-8-quinolinyl)oxy]-1-piperidinyl}-N-(1,1-dimethylethyl)ethanesulfonamide, formate salt (1:1)

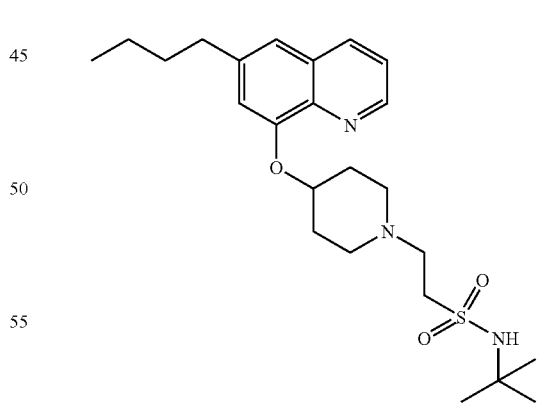

This was prepared in an analogous manner to that disclosed for Example 34 using a mixture of N-(1,1-dimethylethyl)ethenesulfonamide and 2-chloro-N-(1,1-dimethylethyl)ethane sulfonamide (for example, as prepared for Intermediate 42) (1:1), yield 4%. LCMS RT=2.95 min, ES+ve m/z 448 (M+H)$^+$.

Example 34

3-{4-[(6-Butyl-8-quinolinyl)oxy]-1-piperidinyl}-N-(1,1-dimethylethyl)-1-propanesulfonamide, dihydrochloride salt

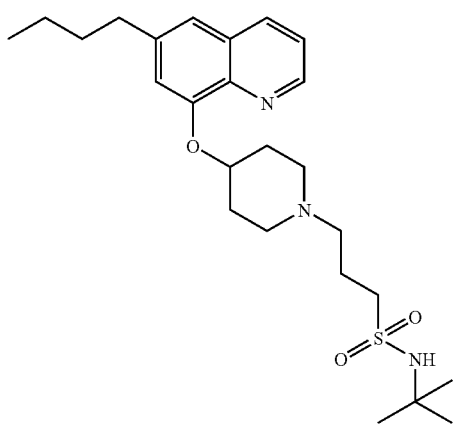

To a solution of 6-butyl-8-(4-piperidinyloxy)quinoline (for example, as prepared for Intermediate 4) (0.24 g, 0.84 mmol) in DMF (5 ml) was added sodium iodide (0.22 g, 1.5 mmol), potassium carbonate (0.21 g, 1.5 mmol) and then 3-chloro-N-(1,1-dimethylethyl)-1-propanesulfonamide (for example, as prepared for Intermediate 41) (0.32 g, 1.50 mmol). The slight suspension was heated to 60° C. for 6 h. The mixture was applied to an SCX-2 cartridge (20 g), preconditioned with methanol, and the cartridge washed with methanol (2 column volumes). The cartridge was eluted with 10% 0.880 s.g. ammonia in methanol (2 column volumes) and the basic fractions concentrated in vacuo. The residue (0.36 g) was purified by MDAP and the appropriate fractions combined. The solvent was removed in vacuo to give the formate salt of the title compound (142 mg, 33%): LCMS RT=2.90 min, ES+ve m/z 462 (M+H)+. A portion of the formate salt (47 mg, 0.092 mmol) in methanol (1.5 ml) was treated with 1.25 M hydrogen chloride in methanol (0.5 ml, 0.6 mmol). The solvent was removed using a stream of nitrogen to give the title compound as a yellow solid (49 mg). LCMS RT=2.95 min, ES+ve m/z 462 (M+H)+.

Example 35

4-{4-[(6-Butyl-8-quinolinyl)oxy]-1-piperidinyl}-N-propyl-1-butanesulfonamide, formate salt (1:1)

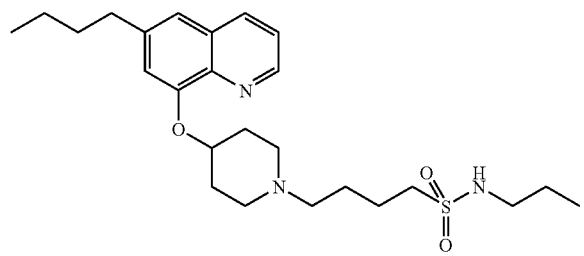

This was prepared in an analogous manner to that disclosed for Example 34 using 4-chloro-N-propyl-1-butanesulfona-mide (for example, as prepared for Intermediate 43). Yield 5%. LCMS RT=2.92 min, ES+ve m/z 462 (M+H)+.

Example 36

N-(3-{4-[(6-Butyl-8-quinolinyl)oxy]-1-piperidinyl}propyl)-N'-propylurea, dihydrochloride salt

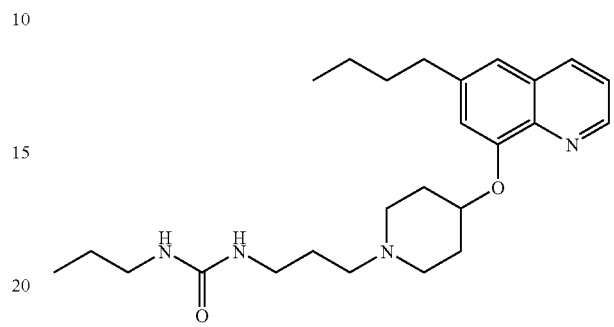

(3-{4-[(6-Butyl-8-quinolinyl)oxy]-1-piperidinyl}propyl)amine (for example, as prepared for Intermediate 36) (33 mg, 0.1 mmol) was dissolved in DCM (2 ml), and treated with propyl isocyanate (commercially available, for example, from Aldrich) (14 μl, 0.15 mmol). The mixture was stirred at room temperature for 20 min, then left to stand at room temperature overnight. The reaction mixture was applied to an SCX-2 cartridge (10 g) eluting with methanol, followed by 10% aqueous 0.88 s.g. ammonia in methanol. The relevant fractions were concentrated, and the residue was purified by MDAP. The appropriate fractions were combined and concentrated to give the title compound as the formate salt (34 mg): LCMS RT=2.76 min, ES+ve m/z 427 (M+H)+. The material was dissolved in methanol and treated with 1.25 M hydrogen chloride in methanol (0.5 ml, excess). The volatiles were removed under a stream of nitrogen to give the title compound (40.5 mg, 81%): LCMS RT=2.78 min, ES+ve m/z 427 (M+H)+.

Biological Assays

The compounds of the invention may be tested for in vitro and/or in vivo biological activity in accordance with the following or similar assays.

H1 Receptor Cell Line Generation and FLIPR Assay Protocol

1. Generation of Histamine H1 Cell Line

The human H1 receptor is cloned using known procedures described in the literature [Biochem. Biophys. Res. Commun., 201(2):894 (1994)]. Chinese hamster ovary (CHO) cells stably expressing the human H1 receptor are generated according to known procedures described in the literature [Br. J. Pharmacol., 117(6):1071 (1996)].

Histamine H1 Functional Antagonist Assay: Determination of Functional pKi Values The histamine H1 cell line is seeded into non-coated black-walled clear bottom 384-well tissue culture plates in alpha minimum essential medium (Gibco/Invitrogen, cat no. 22561-021), supplemented with 10% dialysed foetal calf serum (Gibco/Invitrogen cat no. 12480-021) and 2 mM L-glutamine (Gibco/Invitrogen cat no 25030-024) and is maintained overnight at 5% CO2, 37° C.

Excess medium is removed from each well to leave 10 μl. 30 μl loading dye (250 μM Brilliant Black, 2 μM Fluo-4 diluted in Tyrodes buffer+probenecid (145 mM NaCl, 2.5 mM KCl, 10 mM HEPES, 10 mM D-glucose, 1.2 mM $MgCl_2$, 1.5 mM $CaCl_2$, 2.5 mM probenecid, pH adjusted to 7.40 with NaOH 1.0 M)) is added to each well and the plates are incubated for 60 min at 5% $CO_2$, 37° C.

10 µl of test compound, diluted to the required concentration in Tyrodes buffer+probenecid (or 10 µl Tyrodes buffer+probenecid as a control) is added to each well and the plate is incubated for 30 min at 37° C., 5% $CO_2$. The plates are then placed into a FLIPR™ (Molecular Devices, UK) to monitor cell fluorescence ($\lambda_{ex}$=488 nm, $\lambda_{EM}$=540 nm) in the manner described in Sullivan et al., (In: Lambert D G (ed.), *Calcium Signaling Protocols*, New Jersey: Humana Press, 1999, 125-136) before and after the addition of 10 µl histamine at a concentration that results in the final assay concentration of histamine being $EC_{80}$.

Functional antagonism is indicated by a suppression of histamine induced increase in fluorescence, as measured by the FLIPR™ system (Molecular Devices). By means of concentration effect curves, functional affinities are determined using standard pharmacological mathematical analysis.

Histamine H1 Functional Antagonist Assay: Determination of Antagonist pA2 and Duration The histamine H1 receptor expressing CHO cells are seeded into non-coated black-walled clear bottom 96-well tissue culture plates as described above.

Following overnight culture, growth medium is removed from each well, washed with 200 µl PBS and is replaced with 50 µl loading dye (250 µM Brilliant Black, 1 µM Fluo-4 diluted in Tyrodes buffer+probenecid (145 mM NaCl, 2.5 mM KCl, 10 mM HEPES, 10 mM D-glucose, 1.2 mM $MgCl_2$, 1.5 mM $CaCl_2$, 2.5 mM probenecid, pH adjusted to 7.40 with NaOH 1.0 M)). Cells are incubated for 45 min at 37° C. The loading buffer is removed and the cells are washed as above, and 90 µl of Tyrodes buffer+probenecid is added to each well. 10 µl of test compound, diluted to the required concentration in Tyrodes buffer+probenecid (or 10 µl Tyrodes buffer+probenecid as a control) is added to each well and the plate is incubated for 30 min at 37° C., 5% $CO_2$.

The plates are then placed into a FLIPR™ (Molecular Devices, UK) to monitor cell fluorescence ($\lambda_{ex}$=488 nm, $\lambda_{EM}$=540 nm) in the manner described in Sullivan et al., (In: Lambert D G (ed.), *Calcium Signaling Protocols*, New Jersey: Humana Press, 1999, 125-136) before and after the addition of 50 µl histamine over a concentration range of 1 mM-0.1 nM. The resultant concentration response curves are analysed by non-linear regression using a standard four parameter logistic equation to determine the histamine $EC_{50}$, the concentration of histamine required to produce a response of 50% of the maximum response to histamine. The antagonist pA2 is calculated using the following standard equation: pA2=log(DR−1)−log [ B] where DR=dose ratio, defined as $EC_{50}$antagonist-treated/$EC_{50}$control and [B]=concentration of antagonist.

To determine the antagonist duration, cells are cultured overnight in non-coated black-walled clear bottom 96-well tissue culture plates, are washed with PBS and are incubated with a concentration of antagonist chosen to give an approximate DR in the range 30-300. Following the 30 min antagonist incubation period, the cells are washed two or three times with 200 µl of PBS and then 100 µl Tyrodes buffer is added to each well to initiate antagonist dissociation. Following incubation for predetermined times, typically 30-270 min at 37° C., the cells are then washed again with 200 µl PBS and are incubated with 100 µl Tyrodes buffer containing Brilliant Black, probenecid and Fluo-4 for 45 min at 37° C., as described above. After this period, the cells are challenged with histamine in the FLIPR™ as described above. The dose ratio at each time point is used to determine the fractional H1 receptor occupancy by the following equation: fractional receptor occupancy=(DR−1)/DR. The decrease in receptor occupancy over time approximates to a straight line and is analysed by linear regression. The slope of this straight line fit is used as an index of the dissociation rate of the antagonist. The dose ratios for antagonist treated cells and for antagonist treated and washed cells at each time point are used to calculate a relative dose ratio (rel DR) which is also used as an index of antagonist duration. Antagonists with long duration of action produce rel DR values close to 1, and antagonists with short duration of action produce rel DR values that approaches the dose ratio value obtained for antagonist treatment alone.

2. H3 Receptor Cell Line Generation, Membrane Preparation and Functional GtpγS Assay Protocols Generation of Histamine H3 Cell Line The histamine H3 cDNA is isolated from its holding vector, pCDNA3.1 TOPO (InVitrogen), by restriction digestion of plasmid DNA with the enzymes BamH1 and Not-1 and is ligated into the inducible expression vector pGene (InVitrogen) digested with the same enzymes. The GeneSwitch™ system (a system where in transgene expression is switched off in the absence of an inducer and switched on in the presence of an inducer) is performed as described in U.S. Pat. Nos. 5,364,791; 5,874,534; and 5,935,934. Ligated DNA is transformed into competent DH5α *E. coli* host bacterial cells and is plated onto Luria Broth (LB) agar containing Zeocin™ (an antibiotic which allows the selection of cells expressing the sh ble gene which is present on pGene and pSwitch) at 50 µgml$^{-1}$. Colonies containing the re-ligated plasmid are identified by restriction analysis. DNA for transfection into mammalian cells is prepared from 250 ml cultures of the host bacterium containing the pGeneH3 plasmid and is isolated using a DNA preparation kit (Qiagen Midi-Prep) as per manufacturers guidelines (Qiagen).

CHO K1 cells previously transfected with the pSwitch regulatory plasmid (InVitrogen) are seeded at $2 \times 10^6$ cells per T75 flask in Complete Medium, containing Hams F12 (GIBCOBRL, Life Technologies) medium supplemented with 10% v/v dialysed foetal bovine serum, L-glutamine, and hygromycin (100 µgml$^{-1}$), 24 h prior to use. Plasmid DNA is transfected into the cells using Lipofectamine plus according to the manufacturer's guidelines (InVitrogen). 48 h post transfection, cells are placed into complete medium supplemented with 500 µgml$^{-1}$ Zeocin™.

10-14 days post selection, 10 nM Mifepristone (InVitrogen) is added to the culture medium to induce the expression of the receptor. 18 h post induction, cells are detached from the flask using ethylenediamine tetra-acetic acid (EDTA; 1:5000; InVitrogen), following several washes with PBS, pH 7.4 and are resuspended in Sorting Medium containing Minimum Essential Medium (MEM), without phenol red, and are supplemented with Earles salts and 3% Foetal Clone II (Hyclone). Approximately $1 \times 10^7$ cells are examined for receptor expression by staining with a rabbit polyclonal antibody, 4a, raised against the N-terminal domain of the histamine H3 receptor, are incubated on ice for 60 min, followed by two washes in sorting medium. Receptor bound antibody is detected by incubation of the cells for 60 min on ice with a goat anti rabbit antibody, conjugated with Alexa 488 fluorescence marker (Molecular Probes). Following two further washes with Sorting Medium, cells are filtered through a 50 µm Filcon™ (BD Biosciences) and then are analysed on a FACS Vantage SE Flow Cytometer fitted with an Automatic Cell Deposition Unit. Control cells are non-induced cells treated in an analogous manner. Positively stained cells are sorted as single cells into 96-well plates, containing Complete Medium containing 500 µgml$^{-1}$ Zeocin™ and are allowed to expand before reanalysis for receptor expression via antibody and ligand binding studies. One clone, 3H3, is selected for membrane preparation.

Membrane Preparation from Cultured Cells

All steps of the protocol are carried out at 4° C. and with pre-cooled reagents. The cell pellet is resuspended in 10 volumes of homogenisation buffer (50 mM N-2-hydroxyethylpiperazine-N'-2-ethanesulfonic acid (HEPES), 1 mM ethylenediamine tetra-acetic acid (EDTA), pH 7.4 with KOH, supplemented with 10$^{-6}$ M leupeptin (acetyl-leucyl-leucyl-arginal; Sigma L2884), 25 µgml$^{-1}$ bacitracin (Sigma B0125), 1 mM phenylmethylsulfonyl fluoride (PMSF) and 2×10$^{-6}$ M pepstain A (Sigma)). The cells are then homogenised by 2×15 second bursts in a 1 litre glass Waring blender, followed by centrifugation at 500 g for 20 min. The supernatant is then spun at 48,000 g for 30 min. The pellet is resuspended in homogenisation buffer (4× the volume of the original cell pellet) by vortexing for 5 sec, followed by homogenisation in a Dounce homogeniser (10-15 strokes). At this point the preparation is aliquoted into polypropylene tubes and stored at −80° C.

Histamine H3 Functional Antagonist Assay

For each compound being assayed, in a solid white 384 well plate, is added:—

(a) 0.5 µl of test compound diluted to the required concentration in DMSO (or 0.5 µl DMSO as a control);

(b) 30 µl bead/membrane/GDP mix which is prepared by mixing Wheat Germ Agglutinin Polystyrene LeadSeeker® (WGA PS LS) scintillation proximity assay (SPA) beads with membrane (prepared in accordance with the methodology described above) and diluting in assay buffer (20 mM N-2-hydroxyethylpiperazine-N'-2-ethanesulfonic acid (HEPES)+ 100 mM NaCl+10 mM MgCl$_2$, pH 7.4 NaOH) to give a final volume of 30 µl which contains 5 µg protein, 0.25 mg bead per well and 10 µM final assay concentration of guanosine 5' diphosphate (GDP) (Sigma, diluted in assay buffer) incubating at room temperature for 60 min on a roller;

(c) 15 µl 0.38 nM [$^{35}$S]-GTPγS (Amersham; Radioactivity concentration=37 MBqml$^{-1}$; Specific activity=1160 Cimmol$^{-1}$), histamine (at a concentration that results in the final assay concentration of histamine being EC$_{80}$).

After 2-6 h, the plate is centrifuged for 5 min at 1500 rpm and counted on a Viewlux counter using a 613/55 filter for 5 minplate$^{-1}$. Data is analysed using a 4-parameter logistic equation. Basal activity is used as minimum, i.e. histamine not added to well.

Intranasal Challenge Method: Whole Body Plethysmography (a) Sensitisation

Female Dunkin-Hartley guinea pigs 150-250 g are sensitised twice daily for 5 days (week 1) with ovalbumin (OVA) and aluminium hydroxide (Al(OH)$_3$ or Alum) in physiological saline, 25 µl/nostril. Solution is made up at 20 µg/ml OVA, 180 mg/ml Alum. During weeks 2 and 3 animals receive 25 µl/nostril of OVA (5 mg/ml) once daily. During Week 4 guinea pigs will be entered into study but are continually sensitized as per weeks 2 and 3 until the day before dosing with compound or vehicle.

(b) Compound Vehicle Pretreatment

Pretreatment with test compound is performed at various times prior to histamine challenge. Efficacy dose-response curves are determined 1 hr and/or 3 hr after dosing whereas duration of action may be studied up to 7 days post dose (for example, at 24 hours). Test compounds are formulated as solutions in 0.9% sterile saline or suspensions in 0.9% sterile saline/tween80.

Guinea pigs were anaesthetised with isoflurane (5%, 2-31/min O$_2$), placed in a supine position, and 25 µl of test compound or vehicle dosed into each nostril using a Gilson pipette. After dosing, animals remain supine for at least 30 seconds (e.g. 60 seconds) during recovery from anaesthesia.

(c) Histamine Challenge Protocol

At 30 minutes before the time of histamine challenge, guinea pigs are dosed with atropine sulphate (Sigma A0257, dissolved in saline), 1 mg/kg i.p. Animals are then placed into whole body plethysmograph systems (Buxco® Electronics) where the parameter PenH area under curve (AUC) is recorded as outlined in Hamelmann, E., Schwarze, J., Takeda, K., Oshiba, A., Larsen, L., Irvin, C. G. & Gelfand, E. W. (1997), Noninvasive measurement of airway responsiveness in allergic mice using barometric plethysmography., *Am. J. Respir. Crit. Care Med.*, 156, 766-775. A 10 minute baseline AUC is recorded and if this value is over 1000, the animals are excluded.

After the stipulated pre-dose time has been reached, guinea pigs are re-anaesthetised with isoflurane and dosed with either 10 mM or 15 mM histamine or phosphate-buffered saline (PBS), (25 µl per nostril). On recovery from anaesthesia animals are returned to the individual plethysmograph chambers and 4×10 min consecutive PenH AUC recordings are made. These recordings are summed to give a cumulative AUC over 40 mins post histamine challenge for each animal. Data are analysed using ANOVA with post-hoc Fishers LSD test (general linear models, Statistica®) and finally Hochberg adjustment. Inhibition of histamine-induced congestion is determined by statistically significant differences between the mean responses of compound pre-treated groups compared to the vehicle pre-treated, histamine-challenged group.

CNS Penetration (i) CNS Penetration by Bolus Administration

Compounds are dosed intravenously at a nominal dose level of 1 mgkg$^{-1}$ to male CD Sprague Dawley rats. Compounds are formulated in 5% DMSO/45% PEG200/50% water. Blood samples are taken under terminal anaesthesia with isoflurane at 5 min post-dose and the brains are also removed for assessment of brain penetration. Blood samples are taken directly into heparinised tubes. Blood samples are prepared for analysis using protein precipitation and brain samples are prepared using extraction of drug from brain by homogenisation and subsequent protein precipitation. The concentration of parent drug in blood and brain extracts is determined by quantitative LC-MS/MS analysis using compound-specific mass transitions.

(ii) CNS Penetration Following Intravenous Infusion at Steady State

A loading dose of the compounds is given to male CD Sprague Dawley rats at a nominal dose level of 0.4 mgkg$^{-1}$. The compounds are then infused intravenously for 4 h at a nominal dose level of 0.1 mgkg$^{-1}$h$^{-1}$. Compounds are formulated in 2% DMSO/30% PEG200/68% water. Serial or terminal blood samples are taken at 0.5, 1.5, 2.5, 3, 3.5 and 4 h post dose. The final blood sample is collected under terminal anaesthesia with isoflurane and the brains are also removed for assessment of brain penetration. Blood samples are taken directly into heparinised tubes. Blood samples are prepared for analysis using protein precipitation and brain samples are prepared using extraction of drug from brain by homogenisation and subsequent protein precipitation. The concentration of parent drug in blood and brain extracts is determined by quantitative LC-MS/MS analysis using compound-specific mass transitions.

Results

The compounds of Examples 1 to 36 were tested in the above or similar assays/methods and showed:

(i) Examples 1, 13, 14, 15 and 16 had an average $pK_i$ ($pK_b$) at H1 of approximately greater than 7. The remaining Examples had an average $pK_i$ ($pK_b$) at H1 of approximately greater than 8.

Examples 8, 12 and 13 had average pA2 values of greater than approximately 7. Examples 1, 3, 9, 10, 14, 15, 16, 17, 25, 28, 29, 33 and 35 had average pA2 values of greater than approximately 8. Examples 2, 5, 6, 7, 11, 18, 19, 22, 23B, 24, 26, 31, 32, 34 and 36 had average pA2 values of greater than approximately 9.

(ii) The compounds of the Examples had an average $pK_i$ ($pK_b$) at H3 of less than 6.5.

(iii) The compounds of Example 4A and Example 23B demonstrated low CNS penetration.

(iv) Compound of Examples 4B, 23, 24 and 26 exhibited at one or more time points a longer duration of action than azelastine in the histamine H1 functional antagonist assay. Other compounds were either not tested or were tested and did not exhibit a longer duration of action.

(v) In the intranasal challenge model, compound of Example 23B dosed intranasally at 1 mg/ml either 3 hr or 24 hr before histamine challenge significantly ($p<0.05$) inhibited the response at both timepoints. In the same model, azelastine failed to show a similar duration of action when administered at the same concentration.

Example Compositions

The aqueous pharmaceutical compositions of the invention may be prepared according to the following general method:

Where appropriate, the isotonicity adjusting agent(s) is charged into a suitable mixing vessel containing purified water and dissolved with stirring.

The suspending/thickening agent(s) is then charged into the mixing vessel and dispersed throughout the solution. The resulting suspending vehicle is allowed to hydrate for an appropriate period of time to ensure cross-linkage and gelation, which may take 60 minutes or longer.

Preservative(s) is pre-dissolved in purified water in a separate vessel, optionally with heating, for example to 50-60° C. depending on the preservative chosen, to aid dissolution, and then added to the thickened isotonicity adjusting agent(s) solution with continuous stirring.

Buffering agents, if included, are dissolved in a minimum amount of purified water, optionally heated, for example to about 50-60° C. as appropriate depending on the buffering agents chosen, and stirred to dissolve in separate containers. The separate solutions are combined, mixed well and then added to the bulk solution with continuous stirring.

In a separate mixing vessel, the wetting agent(s) is mixed with purified water which optionally may be heated, for example to about 50-60° C. as appropriate depending on the wetting agent(s) chosen, and stirred to dissolve. A slurry or solution of active compound(s) is then prepared by adding the resultant wetting agent(s) solution to the active compound(s), which may be particle size reduced for example micronised, and mixed prior to homogenising/refining.

Additionally, in a separate mixing vessel, additional preservative(s), if needed, may be mixed with purified water and stirred to dissolve.

Following the dispersion and refining of the slurry/solution of active compound(s) it is added to the mixing vessel containing the suspending/thickening agent and dispersed with stirring. Following the addition of the slurry of active compound(s), any additional preservative may be added to the bulk suspension/solution and dispersed with continuous stirring. Finally, the suspension is made to its final mass by adding water and stirred.

Co-solvent(s), if included, may be added before or after the addition of the buffering agents. Alternatively, the co-solvent(s) may be added during the formation of the drug slurry or solution.

Preservative(s), if included, may be added before or after the addition of the suspending/thickening agent(s).

Fluticasone furoate is used in its unsolvated form as polymorphic Form 1. The preparation of fluticasone furoate (6α, 9α-difluoro-17α-[(2-furanylcarbonyl)oxy]-11β-hydroxy-16α-methyl-3-oxo-androsta-1,4-diene-17β-carbothioic acid S-fluoromethyl ester), solvates and polymorphs thereof including polymorphic Form 1, and biological activity thereof, are disclosed in International Patent Application WO02/12265 and International Patent Application WO03/066024 incorporated fully herein by reference.

N-(4-{4-[(6-butyl-8-quinolinyl)oxy]-1-piperidinyl}butyl) ethanesulfonamide is used in the form of the dihydrochloride salt, optionally as polymorphic form 1.

Example Composition 1 May be Made According to the Following Procedure:

Approximately 200 mL of water is added to a tared beaker. The xyltiol is added with stirring (Silverson mixer) until dissolved. In a separate vessel, the EDTA is dissolved in approximately 5 mL, using heat (without boiling) to aid dissolution. The EDTA solution is then added to the xylitol solution. With mixing (Silverson mixer), the Avicel™ CL611 is added to the xylitol and EDTA solution. The speed of the mixer is adjusted, as required, to maintain a vortex. After addition of the Avicel™ CL611, and once it is well dispersed, the mixture is allowed to stand for at least 60 minutes to ensure hydration of the Avicel™ CL611. In one vessel, the citric acid is dissolved in approximately 10 mL of water, and, in another vessel, the sodium citrate is dissolved in 10 mL of water. The vessels are heated with stirring (without boiling) to aid dissolution. Once the citric acid and sodium citrate are dissolved, they are combined and mixed thoroughly. The buffer is then added to the bulk suspension with mixing (Silverson mixer). In another vessel, the polysorbate 80 is dissolved in approximately 10 mL of water with heat and stirring (without boiling) to aid dissolution. The propylene glycol is added to the polysorbate 80 solution. To N-(4-{4-[(6-butyl- 8-quinolinyl)oxy]-1-piperidinyl}butyl)ethanesulfonamide (in the form of the dihydrochloride salt) is added approximately 3-5 mL of the propylene glycol and polysorbate 80 solution. The drug substance is wetted by mixing with a spatula or alternatively placing in a sealed container and shaking on a shaker until all the drug is wetted. The drug mixture is homogenised (small Silverson head or small Ultra Turrax) to disperse and/or dissolve the drug substance for approximately 2-3 minutes. The drug mixture is added to the bulk suspension and mixed (Silverson mixer). Any remaining polysorbate 80 solution and propylene glycol is added to the bulk suspension. The drug mixture vessel, polysorbate 80 vessel and propylene glycol vessel are rinsed with water (small Silveron head or Ultra Turrax) and the rinsings are added to the bulk solution. In another vessel, the potassium sorbate is dissolved in approximately 5 mL of water with stirring and heat (without boiling) to aid dissolution. The potassium sorbate solution is added to the bulk solution with stirring (Silverson mixer). The tared beaker is made up to the final weight with water (500 g) and mixed for a further 3 minutes. The pH is measured (target pH=4.5, with limits of 4.0 to 5.0).

| Component | Example Composition 1 | Example Composition 2 | Example Composition 3 | Example Composition 4 |
| --- | --- | --- | --- | --- |
| Xylitol | None | 0.75% | None | 0.75% |
| EDTA | 0.015% | 0.015% | 0.015% | 0.015% |
| MC Cellulose & Sodium Carboxymethyl Cellulose (Avicel CL611) | 2.4% | 2.4% | 2.4% | 2.4% |
| Potassium Sorbate | 0.3% | 0.3% | 0.3% | 0.3% |
| Propylene Glycol | 1.5% | 2.5% | 1.5% | 2.5% |
| Sodium Citrate | 1.48% | 1.48% | 1.48% | 1.48% |
| Citric Acid, Anhydrous | 0.96% | 0.96% | 0.96% | 0.96% |
| Polysorbate 80 | 0.025% | 0.025% | 0.025% | 0.025% |
| N-(4-{4-[(6-butyl-8-quinolinyl)oxy]-1-piperidinyl}butyl)ethane sulfonamide, as free base* | 0.025-0.9% | 0.025-0.9% | 0.025-0.9% | 0.025-0.9% |
| Fluticasone furoate (micronised unsolvated, polymorphic Form 1) | None | None | 0.05% | 0.05% |
| Purified Water | to 100% | to 100% | to 100% | to 100% |

| Component | Example Composition 5 | Example Composition 6 | Example Composition 7 | Example Composition 8 |
| --- | --- | --- | --- | --- |
| Xylitol | None | 0.75% | None | 0.75% |
| EDTA | 0.015% | 0.015% | 0.015% | 0.015% |
| MC Cellulose & Sodium Carboxymethyl Cellulose (Avicel CL611) | 2.4% | 2.4% | 2.4% | 2.4% |
| Potassium Sorbate | 0.3% | 0.3% | 0.3% | 0.3% |
| Propylene Glycol | 1.5% | 2.5% | 1.5% | 2.5% |
| Sodium Citrate | 1.48% | 1.48% | 1.48% | 1.48% |
| Citric Acid, Anhydrous | 0.96% | 0.96% | 0.96% | 0.96% |
| Polysorbate 80 | 0.025% | 0.025% | 0.025% | 0.025% |
| N-(4-{4-[(6-butyl-8-quinolinyl)oxy]-1-piperidinyl}butyl)ethane sulfonamide, as free base* | 0.025-0.9% | 0.025-0.9% | 0.025-0.9% | 0.025-0.9% |
| Fluticasone furoate (micronised unsolvated, polymorphic Form 1) | 0.05% | 0.05% | None | None |
| Purified Water | to 100% | to 100% | to 100% | to 100% |

In Example Compositions 1 to 8, the concentration of micronised N-(4-{4-[(6-butyl-8-quinolinyl)oxy]-1-piperidinyl}butyl)ethanesulfonamide is given as the free base, which concentrations are 0.025% (w/w), 0.05% (w/w), 0.1% (w/w), 0.25% (w/w), 0.5% (w/w) and 0.9% (w/w), based on the total weight of the composition.

It will be appreciated that N-(4-{4-[(6-butyl-8-quinolinyl)oxy]-1-piperidinyl}butyl)ethanesulfonamide may be used in the form of a pharmaceutically acceptable salt at an appropriate concentration, depending on the salt chosen, such as to provide the desired concentration of free base.

Example compositions may be filled into suitable containers depending on the chosen route of administration. For intransal administration, suitable containers are described hereinabove and typically are made of plastics and dispense 50 to 100 µL of composition per actuation.

The invention claimed is:

1. A compound which is N-(4-{4-[(6-butyl-8-quinolinyl)oxy]-1-piperidinyl}butyl)ethanesulfonamide

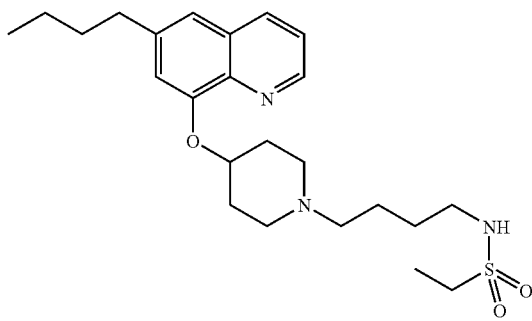

or a salt thereof.

2. A compound according to claim 1, in the form of the free base.

3. A compound according to claim 1, or a pharmaceutically acceptable salt thereof.

4. A compound according to claim 1, in the form of a dihydrochloride salt.

5. A composition which comprises a compound which is N-(4-{4-[(6-butyl-8-quinolinyl)oxy]-1-piperidinyl}butyl)ethanesulfonamide

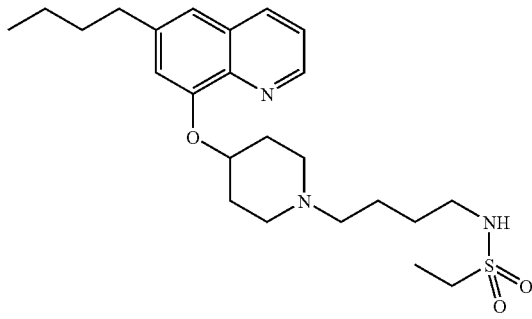

or a pharmaceutically acceptable salt thereof, and one or more pharmaceutically acceptable carriers and/or excipients.

6. A composition according to claim 5 in which the compound is in the form of the free base.

7. A composition according to claim 5 in which the compound is in the form of a dihydrochloride salt.

8. A composition according to any of claims 5 to 7, wherein said composition is suitable for intranasal delivery.

9. A combination comprising a compound which is N-(4-{4-[(6-butyl-8-quinolinyl)oxy]-1-piperidinyl}butyl)ethanesulfonamide

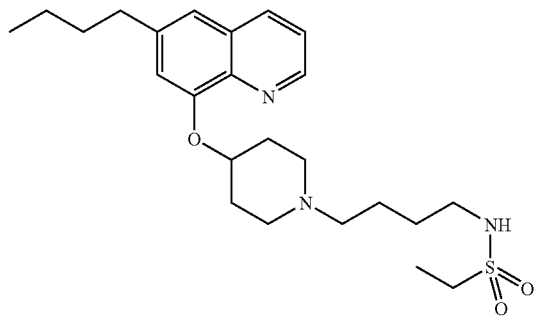

or a pharmaceutically acceptable salt thereof, and one or more other therapeutic agents.

10. A combination according to claim 9, in which the compound is in the form of the free base.

11. A combination according to claim 9 in which the compound is in the form of a dihydrochloride salt.

12. A combination according to any of claims 9 to 11, in which said one or more therapeutic agents is a corticosteroid.

13. A combination according to any of claims 9 to 11, in which said one or more therapeutic agents is fluticasone furoate (6α,9α-difluoro-17α-[(2-furanylcarbonyl)oxy]-11β-hydroxy-16α-methyl-3-oxo-androsta-1,4-diene-17β-carbothioic acid S-fluoromethyl ester).

14. A method for the treatment of inflammatory and/or allergic diseases of the respiratory tract which comprises administering to a patient in need thereof an effective amount of a compound which is N-(4-{4-[(6-butyl-8-quinolinyl)oxy]-1-piperidinyl}butyl)ethanesulfonamide

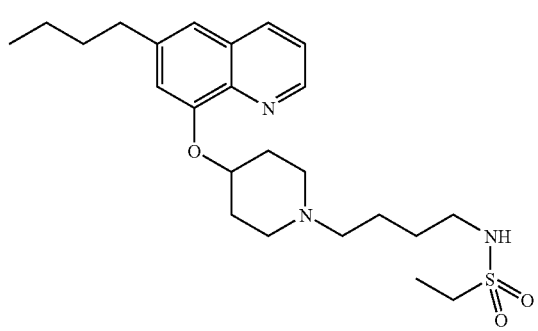

or a pharmaceutically acceptable salt thereof.

15. A method according to claim 14 in which the compound is in the form of the free base.

16. A method according to claim 14 in which the compound is in the form of a dihydrochloride salt.

17. A method according to any of claims 14 to 16, wherein the disease is allergic rhinitis.

18. A method according to any of claims 14 to 16, wherein the compound is administered intranasally.

* * * * *